US011345909B2

(12) United States Patent
Wichelecki et al.

(10) Patent No.: US 11,345,909 B2
(45) Date of Patent: May 31, 2022

(54) ENZYMATIC PRODUCTION OF HEXOSES

(71) Applicant: BONUMOSE LLC, Charlottesville, VA (US)

(72) Inventors: Daniel Joseph Wichelecki, Charlottesville, VA (US); Edwin O. Rogers, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 0 days.

(21) Appl. No.: 16/493,519

(22) PCT Filed: Mar. 13, 2018

(86) PCT No.: PCT/US2018/022185
§ 371 (c)(1),
(2) Date: Sep. 12, 2019

(87) PCT Pub. No.: WO2018/169957
PCT Pub. Date: Sep. 20, 2018

(65) Prior Publication Data
US 2020/0131547 A1    Apr. 30, 2020

Related U.S. Application Data

(60) Provisional application No. 62/482,148, filed on Apr. 5, 2017, provisional application No. 62/480,798, filed on Apr. 3, 2017, provisional application No. 62/470,620, filed on Mar. 13, 2017, provisional application No. 62/470,605, filed on Mar. 13, 2017.

(51) Int. Cl.
| | | |
|---|---|---|
| *C12N 9/90* | (2006.01) | |
| *C12N 9/10* | (2006.01) | |
| *C12N 9/16* | (2006.01) | |
| *C12N 9/92* | (2006.01) | |
| *C12P 19/24* | (2006.01) | |
| *C12P 19/02* | (2006.01) | |
| *C12P 19/14* | (2006.01) | |
| *C12P 19/18* | (2006.01) | |

(52) U.S. Cl.
CPC ............. *C12N 9/90* (2013.01); *C12N 9/1051* (2013.01); *C12N 9/16* (2013.01); *C12N 9/92* (2013.01); *C12P 19/02* (2013.01); *C12P 19/14* (2013.01); *C12P 19/18* (2013.01); *C12P 19/24* (2013.01); *C12Y 204/01001* (2013.01); *C12Y 301/03011* (2013.01); *C12Y 503/01009* (2013.01); *C12Y 504/02002* (2013.01)

(58) Field of Classification Search
CPC ................................. C12P 19/24; C12P 19/02
See application file for complete search history.

(56) References Cited

U.S. PATENT DOCUMENTS

| | | |
|---|---|---|
| 5,767,378 A | 6/1998 | Bojsen et al. |
| 7,094,582 B2 † | 8/2006 | Bao |
| 2002/0164588 A1 | 11/2002 | Eisenberg et al. |
| 2003/0135870 A1 | 7/2003 | Cheikh et al. |
| 2007/0009900 A1 | 1/2007 | Doucette-Stamm et al. |
| 2007/0039069 A1 | 2/2007 | Rogers et al. |
| 2012/0156746 A1 | 6/2012 | Caimi et al. |
| 2012/0266329 A1 | 10/2012 | Mathur et al. |
| 2016/0186162 A1 | 6/2016 | Oh et al. |
| 2016/0186168 A1 | 6/2016 | Konieczka et al. |
| 2016/0244769 A1 | 8/2016 | Xia et al. |
| 2017/0016038 A1 | 1/2017 | Maertens et al. |

FOREIGN PATENT DOCUMENTS

| | | |
|---|---|---|
| WO | 02/077183 A2 | 10/2002 |
| WO | 2015/147644 A1 | 10/2015 |
| WO | 2016/201110 A1 | 12/2016 |
| WO | 2017/002978 A1 | 1/2017 |
| WO | 2018/129275 A1 | 7/2018 |
| WO | 2019/144944 A1 | 8/2019 |

OTHER PUBLICATIONS

International Search Report and Written Opinion in International Application No. PCT/US2018/022185, dated Jun. 20, 2018.
Berrisford et al., "Crystal Structure of Pyrococcus furious Phosphoglucose Isomerase", Journal of Biological Chemistry, vol. 278, No. 35, 3003, pp. 33290-33297.
Tyrel Bryan "Criteria for Evolution of Successful Protein: Fold Fitness and Domain Dynamics Explored", Thesis, University of New Mexico, Sep. 12, 2014, pp. 1-99.
Chan et al., Biochemistry, 2008, vol. 47, No. 36, pp. 9608-9617.
Bruce M. Chassy and John Thompson "Regulation and Characterization of the Galactose-Phosphoenolpyruvate-Dependent Phosphotransferase System in Lactobacillus casei", J. Bacteriology, 1983, vol. 154, No. 3, pp. 1204-1214.
Fekete et al., "The alternative D-galactose degrading pathway of Aspergillus nidulans proceeds via L-sorbose", Arch. Microbiol., 2004, 181, pp. 35-44.
Jung et al., "Crystal Structre and Substrate Specificity of D-Galactose-6-Phosphate Isomerase Complexed with Substrates", PLOS One, 2013, vol. 8, Issue 8, e72902, pp. 1-10.
Kano et al., "The rare sugar D-allose acts as a triggering molecule of rice deference via ROS generation", J. Experimental Botany, vol. 64, No. 16, 2013, pp. 4939-4951.
Kemp et al., "Microbial growth on C1 compounds, Incorporation of C1 units into allulose phosphate by extracts of Pseudomonas methanica", Biochem. J., 1966, 99, 41.
Ruijter et al., "Mannitol is Required for Stress Tolerance in Aspergillus niger Conidiospores", Eukaryotic Cell, 2003, vol. 2, No. 4, pp. 690-698.

(Continued)

*Primary Examiner* — Suzanne M Noakes
(74) *Attorney, Agent, or Firm* — J.A. Lindeman & Co. PLLC

(57) ABSTRACT

Disclosed herein are methods of producing hexoses from saccharides by enzymatic processes. The methods utilize fructose 6-phosphate and at least one enzymatic step to convert it to a hexose.

12 Claims, 20 Drawing Sheets

Specification includes a Sequence Listing.

(56) References Cited

OTHER PUBLICATIONS

Solopova et al., "A specific mutation in the promoter region of the silent cel cluster accounts for the appearance of lactose-utilizing lactococcus lactis MG1363", Applied and Environmental Microbiology, 2012, vol. 78, No. 16, pp. 5612-5621.

Van Rooijen et al., "Molecular Cloning, Characterization, and Nucleotide Sequence of the Tagatose 6-Phosphate Pathway Gene Cluster of the Lactose Operon of Lactococcus lactis", J. Biological Chem., vol. 266, No. 11, 1991, pp. 7176-7181.

Li et al., Biosynthesis of rare hexoses using microorganisms and related enzymes. Beilstein Journal of Organic Chemistry, Nov. 12, 2013, vol. 9, pp. 2434-2445.

Lim, Y-R. and Oh, D-K., Microbial metabolism and biotechnological production of D-allose. Applied Microbiology and Biotechnology, Jun. 8, 2011, vol. 91, No. 2, pp. 229-235.

Fushinobu et al., Nature, 2011, 478:538-542.

Wichelecki, Daniel J., et al. "ATP-binding cassette (ABC) transport system solute-binding protein-guided identification of novel d-altritol and galactitol catabolic pathways in Agrobacterium tumefaciens C58." Journal of Biological Chemistry 290.48 (2015): 28963-28976.†

Chan et al., Structural Basis for Substrate Specificity in Phosphate Binding (B/a)8-Barrels: d-Allulose 6-Phosphate 3-Epimerase from *Escherichia coli* K-12, Biochemistry. Sep. 9, 2008; 47(36): 9608-9617.†

Zhang et al, The 2.2 A Resolution Structure of RpiB/AlsB from *Escherichia coli* Illustrates a New Approach to the Ribose-5-phosphate Isomerase Reaction, J Mol Biol. Oct. 3, 2003; 332(5): 1083-1094.†

Roos, Annette K., et al. "D-ribose-5-phosphate isomerase B from *Escherichia coli* is also a functional D-allose-6-phosphate isomerase, while the *Mycobacterium tuberculosis* enzyme is not." Journal of molecular biology 382.3 (2008): 667-679.†

Roos, Annette K., et al. "D-ribose-5-phosphate isomerase B from *Escherichia coli* is also a functional D-asslose-6-phosphate isomerase, while the *Mycobacterium tuberculosis* enzyme is not." Journal of molecular biology 382.3 (2008): 667-679.†

Zhang et al, The 2.2 A Resolution Structure of RpiB/AlsB from *Escherichia coli* Illustrates a New Approach to the Ribose-5-phosphate Isomerase Reaaction, J Mol Biol. Oct. 3, 2003; 332(5): 1083-1094.†

Huang et al., Panoramic view of a superfamily of phosphates through substrate profiling Proc Natl Acad Sci USA 2015, 21; 112(16): E1974-83.†

Moradian et al., A biomimetic biotechnological process for converting starch to fructose—thermodynamic and evolutionary considerations in applied enzymology, J. Am. Chem. Soc., 1992, 114, 6980-6987.†

† cited by third party

SEQUENCE LISTING

```
<160> NUMBER OF SEQ ID NOS: 21

<210> SEQ ID NO 1
<211> LENGTH: 149
<212> TYPE: PRT
<213> ORGANISM: Clostridium thermocellum

<400> SEQUENCE: 1

Met Lys Ile Gly Ile Gly Ser Asp His Gly Gly Tyr Asn Leu Lys Arg
1               5                   10                  15

Glu Ile Ile Asp Phe Leu Lys Lys Arg Glu Tyr Glu Val Ile Asp Phe
                20                  25                  30

Gly Thr Tyr Gly Thr Asp Ser Val Asp Tyr Pro Asp Phe Gly Leu Lys
            35                  40                  45

Val Ala Glu Ala Val Lys Gly Gly Glu Cys Asp Arg Gly Ile Val Val
        50                  55                  60

Cys Gly Thr Gly Val Gly Ile Ser Ile Ser Ala Asn Lys Val Pro Gly
65                  70                  75                  80

Ile Arg Ala Ala Val Cys Thr Asn Ser Tyr Met Ala Arg Met Ser Arg
                85                  90                  95

Glu His Asn Asp Ala Asn Ile Leu Ala Leu Gly Glu Arg Val Val Gly
                100                 105                 110

Leu Asp Leu Ala Leu Asp Ile Val Asp Thr Trp Leu Lys Ala Glu Phe
            115                 120                 125

Gln Gly Gly Arg His Ser Ala Arg Val Gly Lys Ile Gly Glu Ile Glu
        130                 135                 140

Glu Lys Tyr Ser Lys
145

<210> SEQ ID NO 2
<211> LENGTH: 154
<212> TYPE: PRT
<213> ORGANISM: Symbiobacterium thermophilum

<400> SEQUENCE: 2

Met Arg Ile Ala Ile Gly Asn Asp His Val Gly Thr Glu Met Lys Arg
1               5                   10                  15

Ala Ile Ala Ala His Leu Glu Ser Leu Gly His Glu Val Val Asn Phe
                20                  25                  30
```

```
Gly Thr Asp Ser Thr Glu Arg Thr Asp Tyr Pro Ile Tyr Gly Glu Arg
            35                  40                  45

Val Ala Arg Ala Val Ala Ala Gly Glu Val Asp Cys Gly Ile Leu Ile
 50                  55                  60

Cys Gly Thr Gly Val Gly Ile Ser Leu Ala Ala Asn Lys Val Arg Gly
 65                  70                  75                  80

Ile Arg Ala Val Val Cys Ser Glu Pro Tyr Thr Ala Arg Leu Ser Lys
                 85                  90                  95

Gln His Asn Asn Thr Asn Ile Leu Ala Phe Gly Ala Arg Val Val Gly
            100                 105                 110

Val Asp Leu Ala Lys Met Ile Val Asp Glu Trp Leu Asn Ala Ser Phe
            115                 120                 125

Glu Gly Gly Arg His Gln Arg Arg Val Asp Met Ile Ala Asp Ile Glu
            130                 135                 140

Arg Arg Glu Glu Cys Gly Pro Glu Gly Cys
145                 150
```

<210> SEQ ID NO 3
<211> LENGTH: 217
<212> TYPE: PRT
<213> ORGANISM: Rubellimicrobium thermophilum

<400> SEQUENCE: 3

```
Met Thr Ser Arg Tyr Asp Ala Val Val Phe Asp Leu Asp Gly Thr Leu
  1               5                  10                  15

Ile Asp Thr Glu Ser Leu Cys Asn Ala Ala Gly Val Glu Ala Cys Ala
                 20                  25                  30

Ala Leu Gly Leu Pro Val Ser Gly Glu Phe Phe Glu Ser Leu Ala Gly
             35                  40                  45

Ile Asp Asp Arg Thr Arg Val Gln Leu Ile Gly Glu His Val Gly Thr
 50                  55                  60

Ala Val Asp Leu Ser Ala Phe Leu Ala Ala Trp Asp Arg Leu Cys Ile
 65                  70                  75                  80

Glu Arg Phe Ala Gln Gly Ile Pro Leu Lys Pro Gly Ala Ile Glu Leu
                 85                  90                  95

Leu Glu Gln Ile Ala Ala Ala Gly Ile Pro Leu Ala Leu Ala Thr Ser
            100                 105                 110

Ser Arg Arg Gly Pro Ala Glu Asp Lys Leu Arg Met Ala Gly Leu Ala
            115                 120                 125

Arg His Phe Arg Thr Val Val Thr Phe Asp Asp Val Ala Ala Pro Lys
            130                 135                 140

Pro Ala Pro Asp Ala Tyr Leu Leu Ala Val Asp Arg Leu Gly Val Pro
145                 150                 155                 160

Pro Ala Arg Ala Leu Ala Phe Glu Asp Ser Glu Thr Gly Ala Arg Ala
                165                 170                 175

Ala His Ala Ala Gly Leu Thr Val Val Gln Val Pro Asp Leu His Pro
            180                 185                 190

Thr Gln Gly Ala His Ala His His Val Ala Ser Ser Leu Leu Glu Gly
            195                 200                 205

Ala Ala Met Ala Gly Leu Leu Pro Val
            210                 215
```

<210> SEQ ID NO 4
<211> LENGTH: 216
<212> TYPE: PRT

<213> ORGANISM: Thermotoga maritima

<400> SEQUENCE: 4

Met Glu Ala Val Ile Phe Asp Met Asp Gly Val Leu Met Asp Thr Glu
1               5                   10                  15

Pro Leu Tyr Phe Glu Ala Tyr Arg Arg Val Ala Glu Ser Tyr Gly Lys
            20                  25                  30

Pro Tyr Thr Glu Asp Leu His Arg Arg Ile Met Gly Val Pro Glu Arg
        35                  40                  45

Glu Gly Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
            85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
            165                 170                 175

Gly Ile Glu Arg Ile Tyr Gly Val Val His Ser Leu Asn Asp Gly Lys
        180                 185                 190

Ala Leu Leu Glu Ala Gly Ala Val Ala Leu Val Lys Pro Glu Glu Ile
    195                 200                 205

Leu Asn Val Leu Lys Glu Val Leu
    210                 215

<210> SEQ ID NO 5
<211> LENGTH: 218
<212> TYPE: PRT
<213> ORGANISM: Thermoanaerobacterium saccharolyticum

<400> SEQUENCE: 5

Met Phe Glu Ala Val Ile Leu Asp Met Asp Gly Val Leu Ile Asp Ser
1               5                   10                  15

Glu Pro Leu His Ile Gln Leu Glu Glu Glu Ile Phe Lys Glu Ile Gly
            20                  25                  30

Ala Asp Ile Ser Leu Glu Glu His Ile Ser Phe Val Gly Thr Thr Ser
        35                  40                  45

His Tyr Met Trp Glu Tyr Val Lys Asn Lys Cys Asn Val Ser Phe Thr
    50                  55                  60

Val Glu Glu Leu Val Glu Met Asp Arg Lys Arg Tyr Phe Asp Tyr Ile
65                  70                  75                  80

Ser Lys His Asp Gly Ala Val Lys Pro Ile Glu Gly Val Asp Glu Leu
            85                  90                  95

Val Lys Glu Leu Tyr Ser Arg Glu Val Arg Leu Ala Val Ala Ser Ser
            100                 105                 110

Ser Pro Ile Asp Val Ile Glu Leu Val Val Lys Lys Leu His Leu Asn
        115                 120                 125

Asp Tyr Phe Cys Glu Leu Val Ser Gly Asp Phe Val Lys Arg Ser Lys

```
            130                 135                 140
Pro Tyr Pro Asp Ile Phe Leu Tyr Ala Ala Glu Lys Leu Gly Val Ser
145                 150                 155                 160

Pro Glu Arg Cys Leu Val Val Glu Asp Ser Asn Lys Gly Val Leu Ala
                165                 170                 175

Ala Lys Ser Ala Gly Met Lys Val Ile Gly Phe Ile Asn Pro Asn Ser
            180                 185                 190

Gly Asp Gln Asp Ile Ser Met Ala Asp Met Val Ile Arg Ser Phe Ser
                195                 200                 205

Glu Leu Asn Tyr Glu Lys Leu Gln Asn Ile
            210                 215
```

<210> SEQ ID NO 6
<211> LENGTH: 220
<212> TYPE: PRT
<213> ORGANISM: Streptomyces thermoautotrophicus

<400> SEQUENCE: 6

```
Met Pro Ser Ser Ser Gly Gly Leu Gln Ala Val Phe Phe Asp Met Asp
1               5                   10                  15

Gly Leu Leu Val Asp Thr Glu Pro Thr Trp His Glu Val Glu Ala Glu
                20                  25                  30

Val Met Ala Glu Tyr Gly Tyr Ala Trp Thr Pro Glu Asp Arg Leu Ala
            35                  40                  45

Cys Leu Gly Gly Pro Met Glu Arg Thr Cys Arg Tyr Met Ile Glu Arg
        50                  55                  60

Cys Gly Ala Asp Ile Thr Val Glu Ala Leu Gly Ala Thr Leu Val Glu
65                  70                  75                  80

Arg Met Ala Leu Arg Val Arg Glu Glu Val Ala Val Gln Pro Gly Ala
                85                  90                  95

Lys Glu Leu Leu Ser Glu Leu Ile Glu Ala Gly Val Pro Arg Ala Leu
            100                 105                 110

Val Ser Ser Ser Phe Arg Val Leu Val Asp Ala Val Leu Asp Ala Val
        115                 120                 125

Gly His Asp Leu Phe Val Val Thr Val Ala Gly Asp Glu Val Ala Arg
    130                 135                 140

Ala Lys Pro His Pro Glu Pro Tyr Leu Thr Ala Ala Arg Leu Gly
145                 150                 155                 160

Val Asp Pro Ala Arg Cys Val Val Leu Glu Asp Ser Pro Pro Gly Val
                165                 170                 175

Ala Ala Ala Glu Ala Ala Gly Cys Leu Val Val Ala Val Pro Ser Val
            180                 185                 190

Ala Pro Leu Glu Pro Ala Pro Arg Arg Leu Val Val Arg Ser Leu Thr
        195                 200                 205

Glu Leu Ser Leu Asp Arg Leu Arg Ala Leu Ile Ala
    210                 215                 220
```

<210> SEQ ID NO 7
<211> LENGTH: 219
<212> TYPE: PRT
<213> ORGANISM: Sphaerobacter thermophilus

<400> SEQUENCE: 7

```
Met Ser Gln Gly Val Arg Gly Val Val Phe Asp Leu Asp Gly Leu Leu
1               5                   10                  15

Val Glu Ser Glu Glu Tyr Trp Glu Gln Ala Arg Arg Glu Phe Val Ser
```

```
                    20                  25                  30
Arg Tyr Gly Gly Thr Trp Gly Asp Asp Ala Gln Gln Ala Val Met Gly
                35                  40                  45
Ala Asn Thr Arg Gln Trp Ser Arg Tyr Ile Arg Glu Ala Phe Asp Ile
 50                  55                  60
Pro Leu Thr Glu Glu Ile Ala Ala Val Ile Ala Arg Met Gln
 65                  70                  75                  80
Glu Leu Tyr His Asp His Leu Pro Leu Pro Gly Ala Ile Pro Ala
                    85                  90                  95
Val Arg Ala Leu Ala Asp Arg Tyr Pro Leu Ala Val Ala Ser Ser Ser
                100                 105                 110
Pro Pro Val Leu Ile Arg Phe Val Leu Ala Glu Met Gly Val Ala Glu
                115                 120                 125
Cys Phe Gln Ser Val Thr Ser Ser Asp Glu Val Ala His Gly Lys Pro
                130                 135                 140
Ala Pro Asp Val Tyr His Leu Ala Cys Glu Arg Leu Gly Val Ala Pro
145                 150                 155                 160
Glu Gln Ala Val Ala Phe Glu Asp Ser Thr Ala Gly Ile Ala Ala Ala
                165                 170                 175
Leu Ala Ala Gly Leu Arg Val Ile Ala Val Pro Asn Arg Ser Tyr Pro
                180                 185                 190
Pro Asp Pro Asp Val Leu Arg Arg Ala Asp Leu Thr Leu Pro Ser Leu
                195                 200                 205
Glu Glu Phe Asp Pro Ala Val Leu Glu Gln Trp
                210                 215
```

<210> SEQ ID NO 8
<211> LENGTH: 400
<212> TYPE: PRT
<213> ORGANISM: Pseudonocardia thermophila

<400> SEQUENCE: 8

```
Met Glu Leu Leu Asp Asn Pro Ile Arg Pro Tyr Ala Trp Gly Ser Arg
 1               5                  10                  15
Thr Val Leu Ala Glu Leu Leu Gly His Glu Ser Pro Ser Pro His Pro
                20                  25                  30
Glu Ala Glu Met Trp Leu Gly Ala His Pro Gly Asp Pro Ser Arg Leu
                35                  40                  45
Arg Ser Gly Glu Ser Leu Leu Asp Ala Leu Cys Ala Asp Pro Glu Gly
 50                  55                  60
Leu Leu Gly Ala Asp Arg Ala Arg Lys Trp Asp Gly Lys Leu Pro Phe
 65                  70                  75                  80
Leu Leu Lys Val Leu Ala Ala Asp Glu Pro Leu Ser Leu Gln Ala His
                85                  90                  95
Pro Ser Leu Asp Gln Ala Arg Val Gly Phe Glu Arg Glu Glu Arg Ala
                100                 105                 110
Gly Ile Ala Arg Asp Ala Pro Glu Arg Asn Tyr Arg Asp Pro Asn His
                115                 120                 125
Lys Pro Glu Leu Leu Cys Ala Leu Thr Glu Phe His Ala Leu Val Gly
                130                 135                 140
Phe Arg Pro Pro Glu Lys Thr Val Glu Leu Leu Ala Ala Leu Ala Val
145                 150                 155                 160
Pro Glu Leu Asp Ala Tyr Ser Gln Leu Leu Thr Ala Gln Pro Asp Ala
                165                 170                 175
```

```
Asn Gly Leu Arg Ala Leu Phe Thr Thr Trp Ile Thr Leu Pro Gln Ser
            180                 185                 190

Val Leu Asp Thr Leu Val Pro Ala Leu Gln Ala Gly Cys Val Arg Leu
        195                 200                 205

Ala Ala Ala Asp Gly Pro Phe Lys Ala Glu Ala Arg Thr Val Leu Glu
    210                 215                 220

Leu Ser Glu Arg Tyr Pro Gly Asp Ala Gly Val Leu Ala Ala Val Leu
225                 230                 235                 240

Leu Asn Arg Val Thr Leu Gln Pro Gly Glu Ala Val Tyr Leu Pro Ala
                245                 250                 255

Gly Asn Leu His Ala Tyr Leu Glu Gly Ala Gly Ile Glu Val Met Ala
            260                 265                 270

Ser Ser Asp Asn Val Leu Arg Gly Gly Leu Thr Pro Lys His Val Asp
        275                 280                 285

Val Pro Glu Leu Leu Arg Val Leu Asp Phe His Ala Ala Val Pro Pro
    290                 295                 300

Val Leu Thr Gly Thr Pro Asp Gly Ala Trp Leu Arg Tyr Asp Thr Pro
305                 310                 315                 320

Phe Glu Glu Phe Leu Leu Arg Arg Leu Glu Gly Asp Pro Ala Ala Gly
                325                 330                 335

Leu Val Ala Val Pro Asp Gly Pro Arg Ile Val Leu Cys Thr Arg
            340                 345                 350

Gly Ala Ala Val Leu Arg Gly Arg Asp Glu Gln Leu Asp Leu His Arg
        355                 360                 365

Gly Ala Ser Ala Trp Leu Gly Ala Asp Asp Thr Gly Leu Thr Val Glu
    370                 375                 380

Ala Val Glu Gln Asn Thr Gln Leu Phe Leu Ala Gly Asp Gly Leu Asp
385                 390                 395                 400

<210> SEQ ID NO 9
<211> LENGTH: 405
<212> TYPE: PRT
<213> ORGANISM: Caldithrix abyssi

<400> SEQUENCE: 9

Met Lys Leu Lys Phe Val Ala Arg Pro Tyr Glu Leu Ile Asn Lys Ile
1               5                   10                  15

Gln Asn Tyr Ser Trp Gly Thr Arg Asn Glu Gln Ala Phe Ile Pro Arg
            20                  25                  30

Leu Leu Asn Met Ala Val Glu Pro Asp Thr Pro Tyr Ala Glu Leu Trp
        35                  40                  45

Met Gly Thr His Pro Asn Ala Pro Ser Glu Val Val Asp Gly Arg
    50                  55                  60

Arg Ile Leu Leu Ser Glu Phe Ile Lys Gln Phe Pro Gln Gln Ile Leu
65                  70                  75                  80

Gly Thr Arg Val Ile Glu Arg Phe Gly Val Gln Leu Pro Phe Leu Phe
                85                  90                  95

Lys Val Leu Ser Ala Ala Glu Ala Leu Ser Ile Gln Ala His Pro Asn
            100                 105                 110

Lys Gln Gln Ala Glu Val Leu His Gln Arg Asp Pro Glu His Tyr Pro
        115                 120                 125

Asp Asp Asn His Lys Pro Glu Ile Ala Ile Ala Leu Asp Glu Leu Thr
    130                 135                 140

Ala Leu Val Gly Phe Arg Ser Leu Lys Glu Met Asp Ala Val Leu Arg
145                 150                 155                 160
```

Thr Phe Pro Glu Ile Leu Glu Phe Thr Gly Pro Leu Glu Phe Thr Phe
            165                 170                 175

Glu Gly Ala Arg His Glu Gln Glu Asn Arg Gln Lys Phe Arg Gln
        180                 185                 190

Phe Tyr Gln Thr Leu Met Leu Lys Ser Gln Thr His Ala Thr Glu Met
        195                 200                 205

Glu Ala Thr Leu Asn Lys Ile Glu Gln Lys Leu Leu Gln Lys Lys
    210                 215                 220

Arg Thr Glu Arg Asp Glu Trp Phe Leu Lys Leu Lys Lys Tyr Gly
225                 230                 235                 240

Ala Asp Val Gly Leu Phe Ser Ile Tyr Leu Leu Asn Leu Leu His Leu
            245                 250                 255

Lys Lys Gly Gln Gly Val Phe Leu Lys Ala Gly Val Pro His Ala Tyr
            260                 265                 270

Leu Lys Gly Asn Ile Val Glu Cys Met Ala Asn Ser Asp Asn Val Val
            275                 280                 285

Arg Ala Gly Leu Thr Pro Lys Phe Lys Asp Val Lys Thr Leu Ile Glu
    290                 295                 300

Val Leu Thr Tyr Glu Thr Gly Pro Val Glu Ile Tyr Glu Gly Ala Gln
305                 310                 315                 320

Asn Ala Lys Tyr Val Tyr Lys Thr Pro Val Asp Glu Phe Ser Ile Thr
            325                 330                 335

His Val Asn Leu Asp Glu Lys Ser Lys Leu Arg Phe Phe Leu Glu Thr
            340                 345                 350

Val Ser Ile Met Met Val Val Asn Gly Lys Gly Glu Ile Val Phe Asn
            355                 360                 365

Gly Gly Arg Leu Ala Ile Gln Lys Gly Gln Ser Ile Leu Leu Pro Ala
    370                 375                 380

Glu Ile Ala Ser Phe Glu Leu Val Ser Asp Gly Ser Leu Glu Ile Phe
385                 390                 395                 400

Ser Ala Tyr Val Pro
            405

<210> SEQ ID NO 10
<211> LENGTH: 453
<212> TYPE: PRT
<213> ORGANISM: Myceliophthora thermophila

<400> SEQUENCE: 10

Met Gln Val Pro Leu Ile Arg Leu Gln Cys Gly Ala Asn Ser Tyr Glu
1               5                   10                  15

Trp Gly Lys Lys Gly Ser Ser Ser Ala Val Ala Arg Phe Ala Ala Ala
            20                  25                  30

Thr Pro Ser Ser Asp Phe Thr Ile Glu Asp Asp Arg Pro Tyr Ala Glu
        35                  40                  45

Leu Trp Met Gly Thr His Pro Ser Asn Pro Ser Lys Asp Leu Ser Thr
    50                  55                  60

Gly Arg Thr Leu Leu Asp Leu Val Gln Asp Asn Lys Ala Leu Leu Ser
65                  70                  75                  80

Pro Ser Val Ala Ala Arg Tyr Asp Asn Lys Val Pro Phe Leu Phe Lys
            85                  90                  95

Val Leu Ser Ile Asn Lys Ala Leu Ser Ile Gln Ala His Pro Asn Lys
            100                 105                 110

Lys Leu Ala Glu Glu Leu His Arg Lys Asp Pro Lys Asn Tyr Pro Asp

```
            115                 120                 125

Asp Asn His Lys Pro Glu Met Ala Ile Ala Ile Thr Pro Phe Glu Gly
        130                 135                 140

Leu Cys Gly Phe Arg Pro Leu Gly Glu Ile Ala His Phe Leu Glu Ser
145                 150                 155                 160

Val Pro Pro Leu Arg Gln Leu Val Gly Asp Asn Ala Arg Glu Phe
                165                 170                 175

Ala Gly Ile Val Arg Gln Asn Lys Asp Asn Asp Ser Lys Asp Ala Val
                180                 185                 190

Glu Gln Asn Lys Lys Ala Leu Gln Lys Ile Phe Gly Ala Leu Met Ser
            195                 200                 205

Ser Ser Glu Ala Asp Met Ala Ala Ala Lys Val Leu Val Glu Ser
210                 215                 220

Ala Ala Thr Ala Gly Ala Asp Phe Ala Ala Gly Gly Val Ala Ala Thr
225                 230                 235                 240

Ser Gly Ser Thr Leu Ala Glu Leu Val Gln Arg Leu His Gly Gln Phe
                245                 250                 255

Gly Ala Asp Tyr Gly Leu Phe Val Leu Phe Phe Leu Asn Phe Val Thr
                260                 265                 270

Leu Gln Pro Gly Glu Ala Leu Phe Leu Arg Ala Asp Asp Ile His Ala
            275                 280                 285

Tyr Val Ser Gly Asp Ile Ile Glu Cys Met Ala Ser Ser Asp Asn Val
        290                 295                 300

Val Arg Ala Gly Phe Thr Pro Lys Phe Lys Asp Val Asp Thr Leu Val
305                 310                 315                 320

Asn Met Leu Thr Tyr Ser Tyr Ala Pro Ile Asp Glu Gln Lys Met Gly
                325                 330                 335

Pro Ser Asp Tyr Pro Tyr Ala Thr Leu Asn Arg Thr Gly Tyr Ser Ser
                340                 345                 350

Gly Ser Thr Ile Ser Phe Tyr Asp Pro Pro Ile Glu Glu Phe Ser Val
            355                 360                 365

Ile Arg Thr Asn Leu Lys Glu Ser Gly Ser Lys Ala Thr Phe Asp Pro
        370                 375                 380

Val Asp Gly Pro Ser Ile Ile Ile Cys Thr Ala Gly Lys Gly Lys Ile
385                 390                 395                 400

Ser Val Gly Pro Thr Ala Gln Glu Val Lys Glu Gly Tyr Val Phe Phe
                405                 410                 415

Val Gly Ala Ser Ala Lys Cys Val Leu Glu Ser Glu Gly Ser Ser Glu
                420                 425                 430

Asp Asp Glu Phe Ile Thr Phe Lys Ala Phe Cys Asp Val Glu Glu His
            435                 440                 445

Arg Gly Ala Ser Leu
        450

<210> SEQ ID NO 11
<211> LENGTH: 410
<212> TYPE: PRT
<213> ORGANISM: Treponema caldarium

<400> SEQUENCE: 11

Met Asn Asn Lys Lys Lys Pro Asn Phe Tyr Leu Leu Lys Asn Pro Ile
1               5                   10                  15

Gln Arg Tyr Ala Trp Gly Ser Lys His Trp Ile Gln Asp Leu Leu Asp
            20                  25                  30
```

Leu Ser Glu Gln Asp Arg Gln Gly Pro Met Ala Glu Leu Trp Met Gly
         35                  40                  45

Ala His Ser Arg Ser Pro Ser Ile Ala Phe Thr Asp Glu Thr Glu Gln
 50                  55                  60

Pro Leu Asp Lys Leu Ile Gln Glu His Pro Val His Phe Leu Gly Asp
 65                  70                  75                  80

Thr Ile Ala His Asp Phe Ser Ser Leu Pro Tyr Leu Phe Lys Ile Leu
                 85                  90                  95

Ala Ala Ala Ser Pro Leu Ser Ile Gln Ala His Pro Asp Lys Gln Gln
             100                 105                 110

Ala Glu Gln Gly Phe Ala Arg Glu Ala Lys Ala Gly Ile Pro Leu Ser
         115                 120                 125

Ala Glu Asn Arg Asn Tyr Lys Asp Ser Asn His Lys Pro Glu Ile Ile
130                 135                 140

Cys Ala Ile Ser Pro Phe Thr Ala Met Cys Gly Phe Arg Thr Gln Ala
145                 150                 155                 160

Glu Ile Ala Glu Leu Leu Ser Leu Leu Asp Val Thr Glu Leu Glu Gln
                165                 170                 175

Ser Leu Val Ala Ile Gln Gln Ile Asp Arg Lys Glu Ala Tyr Arg Asp
            180                 185                 190

Phe Leu Leu Ser Leu Phe Leu Leu Pro Gln Gln Thr Arg Glu Arg Ile
        195                 200                 205

Thr Lys His Ile Gln Ala Lys Leu Pro Lys Leu Glu Gln Lys His Pro
210                 215                 220

Arg Tyr Ala Lys Glu Trp Glu Leu Ile Asn Leu Phe Cys Thr Leu Tyr
225                 230                 235                 240

Pro Gly Asp Ser Ala Ile Ile Ser Pro Leu Tyr Leu Asn Val Leu Ser
                245                 250                 255

Leu Asn Pro Gly Glu Ala Ile Phe Leu Pro Ala Gly Val Leu His Ala
            260                 265                 270

Tyr Ile His Gly Phe Gly Val Glu Leu Met Ala Asn Ser Asp Asn Val
        275                 280                 285

Leu Arg Gly Gly Leu Thr Pro Lys His Ile Asp Ile Lys Glu Leu Leu
290                 295                 300

Asn Ile Ile Arg Phe Glu Ser Phe Lys Pro Ala Val Leu Ser Ala Gln
305                 310                 315                 320

Lys Thr Gln Gln Gly Tyr His Ile Tyr Pro Ser Gln Val Arg Glu Phe
                325                 330                 335

Ser Leu Phe His Val Ala Val Thr Met Asp Lys Ala Gln Gln Leu Met
            340                 345                 350

Pro Gly Thr Pro Ile Ile Leu Ile Val Leu Asp Gly Cys Val Ser Ile
        355                 360                 365

Gly Thr Glu Gln Glu Lys Lys Thr Leu Gln Lys Gly Met Ser Val Phe
370                 375                 380

Leu Pro Ala Glu Arg Glu Gln Leu Ile Leu Glu Gly Ser Ala His Ile
385                 390                 395                 400

Phe Gly Ala Thr Thr Gly Glu Gly Thr Arg
                405                 410

<210> SEQ ID NO 12
<211> LENGTH: 223
<212> TYPE: PRT
<213> ORGANISM: Tepidimonas fonticaldi

<400> SEQUENCE: 12

Met Thr Arg Trp Arg Gly Ile Arg Ala Val Leu Phe Asp Leu Asp Gly
1               5                   10                  15

Thr Leu Val Asp Ser Ala Pro Asp Leu Gly His Ala Ala Asp Leu Met
            20                  25                  30

Arg Gln Arg Arg Gly Leu Pro Pro Leu Asp Glu Ala Tyr Tyr Arg Pro
        35                  40                  45

Arg Ala Ser Ser Gly Ala Arg Gly Met Ile Glu Ala Ala Phe Gly Leu
    50                  55                  60

Thr Pro Glu His Pro Glu Phe Glu Ala Tyr Arg Thr Glu Tyr Leu Asp
65                  70                  75                  80

Thr Tyr Gly Gln Val Leu Thr Arg Arg Thr Arg Pro Phe Asp Gly Val
                85                  90                  95

Ala Glu Leu Ile Ala Ala Leu Asp Arg Ala Gln Val Ala Trp Gly Val
                100                 105                 110

Val Thr Asn Lys Val Glu Arg Phe Ala Leu Pro Leu Thr Ala Ala Ile
            115                 120                 125

Pro Leu Phe Ala Thr Ala Ala Thr Val Ile Gly Gly Asp Thr Thr Pro
        130                 135                 140

His Pro Lys Pro His Pro Ala Pro Leu Leu Glu Ala Ala Arg Arg Leu
145                 150                 155                 160

Gln Leu Pro Pro Gln Ala Cys Leu Tyr Val Gly Asp Asp Glu Arg Asp
                165                 170                 175

Ile Val Ala Gly Arg Ala Ala Gly Met Pro Thr Val Ala Ala Arg Tyr
                180                 185                 190

Gly Tyr Leu Gly Val Ala Ala Asp Val Glu Ala Trp Ala Ala Asp Ala
            195                 200                 205

Ile Ile Glu Ser Pro Gln Ala Leu Leu Asn Phe Leu Asp Leu Ala
            210                 215                 220

<210> SEQ ID NO 13
<211> LENGTH: 221
<212> TYPE: PRT
<213> ORGANISM: Thermomonas hydrothermalis

<400> SEQUENCE: 13

Met Ser Ala Arg Arg Phe Pro Pro Leu Val Leu Phe Asp Leu Asp Gly
1               5                   10                  15

Thr Leu Leu Asp Ser Ala Pro Asp Met Leu Val Thr Val Asn Arg Met
            20                  25                  30

Arg Ala Met Arg Gly Asp Ala Pro Met Ala Leu Asp Ala Leu Arg Pro
        35                  40                  45

His Val Ser Arg Gly Ala Arg Ala Met Ile Ala Ala Ser Phe Pro Ala
    50                  55                  60

Leu Gly Gly Glu Val Pro Ala Glu Met Val Arg Glu Phe Leu Asp Ile
65                  70                  75                  80

Tyr Ala Gln Val Leu Gly Gln His Gly Ala Pro Phe Asp Gly Val Val
                85                  90                  95

Glu Leu Leu Ala Ala Leu Glu Ala Ala Gly Ser Arg Trp Gly Ile Val
                100                 105                 110

Thr Asn Lys Pro Glu Ser Leu Ala Arg Gln Leu Leu Pro Gly Leu Gly
            115                 120                 125

Trp Asp Ala Arg Cys Ala Ile Leu Val Gly Gly Asp Ser Leu Pro Glu
        130                 135                 140

Arg Lys Pro His Pro Leu Pro Leu Leu His Ala Ala Gly Gln Leu Gly

```
                145                 150                 155                 160
Val Ser Cys Gln Asp Cys Ala Tyr Val Gly Asp Asp Arg Arg Asp Ile
                    165                 170                 175

Glu Ala Ala Arg Ala Ala Gly Met Arg Ser Val Val Ala Leu Trp Gly
                180                 185                 190

Tyr Arg Leu Pro Asp Glu Asn Pro Gln Asp Trp Gly Asp Ala Leu
                    195                 200                 205

Ser Pro Thr Pro Gln Ala Leu Leu Asp Trp Pro Leu Pro
    210                 215                 220

<210> SEQ ID NO 14
<211> LENGTH: 221
<212> TYPE: PRT
<213> ORGANISM: Sulfurivirga caldicuralii

<400> SEQUENCE: 14

Met Arg Glu Phe Asp Cys Val Leu Phe Asp Leu Asp Gly Thr Leu Leu
1               5                   10                  15

Asp Thr Ser Tyr Asp Phe Ala Trp Ala Leu Asn Thr Leu Gln Lys Gln
                20                  25                  30

Glu Ser Val Pro Leu Thr Pro Tyr Trp Arg Ile Arg Gln Thr Ile Ser
            35                  40                  45

Ser Gly Gly Arg Ala Val Val Lys Leu Gly Phe Pro Asp Ala Asp Asp
50                  55                  60

Ala Thr Ile Glu Ala Leu Arg Glu Arg Phe Leu Ala Leu Tyr His Glu
65                  70                  75                  80

Asn Ile Ser Val His Thr Asp Leu Phe Pro Gly Leu Glu Lys Val Leu
                85                  90                  95

Thr His Leu Gln Glu Lys Ala Val Pro Trp Gly Ile Val Thr Asn Lys
            100                 105                 110

Pro Ala Trp Leu Thr Asp Lys Leu Leu Gly Glu Leu Asp Leu Pro Ala
        115                 120                 125

Gln Pro Gln Thr Val Val Ser Gly Asp Thr Leu Ala Val Arg Lys Pro
    130                 135                 140

His Pro Glu Pro Met Trp Leu Ala Ala Glu Gln Cys Gly Val Ala Pro
145                 150                 155                 160

Glu Arg Cys Leu Tyr Ile Gly Asp His Pro Arg Asp Ile Glu Ala Pro
                165                 170                 175

Arg Asn Ala Gly Met Gln Ser Ala Ala Ala Leu Tyr Gly Phe Leu Pro
            180                 185                 190

Leu Asp Ala Glu Pro Asp Ser Trp Pro Ala Asp Tyr Arg Tyr His Ala
        195                 200                 205

Pro Ala Asp Ile Leu His His Met Gln Lys Val Phe Pro
    210                 215                 220

<210> SEQ ID NO 15
<211> LENGTH: 344
<212> TYPE: PRT
<213> ORGANISM: Syntrophothermus lipocalidus

<400> SEQUENCE: 15

Met Ala Val Glu Met Gly Pro Glu Met Met Phe Glu Phe Leu Tyr Asn
1               5                   10                  15

Leu Pro Ala Gln Phe Glu Gly Cys Leu Lys Met Asp Phe Ser Lys Ala
                20                  25                  30

Ser Gly Leu Lys Lys Glu Tyr Ala Asn Ile Val Val Thr Gly Leu Gly
```

```
                35                  40                  45
Gly Ser Ala Ile Gly Gly Asp Ile Leu Arg Cys Tyr Cys Gln Ser Arg
 50                  55                  60

Leu Pro Ile Pro Val Val Asn Arg Asp Tyr Met Leu Pro Arg Phe
 65                  70                  75                  80

Val Gly Pro Asp Ser Leu Val Leu Ala Val Ser Tyr Ser Gly Asn Thr
                 85                  90                  95

Glu Glu Thr Leu Ser Ala Tyr Glu Asp Ala Arg Glu Lys Gly Ala Ser
                100                 105                 110

Ile Ile Ala Phe Thr Thr Gly Gly Lys Leu Ala Glu Met Ala Ala Leu
                115                 120                 125

Asp Gly Asn Pro Val Ile Thr Ile Thr Gly Gly Leu Val Pro Arg Ala
                130                 135                 140

Ala Thr Gly Tyr Leu Phe Ala Pro Leu Val Leu Val Leu Glu Arg Leu
145                 150                 155                 160

Gly Leu Val Ser Gly Ala Ser Glu Asp Val Lys Glu Thr Val Thr Val
                165                 170                 175

Leu Thr Gln Leu Arg Glu Glu Ile Glu Pro Gly Arg Glu Glu Asp Ser
                180                 185                 190

Asn Arg Ala Arg Phe Ile Ala Gly Gln Leu Tyr Gln Arg Ile Pro Val
                195                 200                 205

Ile Trp Gly Cys Ser Ser Thr Ser Glu Val Ala Ala Met Arg Trp Lys
210                 215                 220

Gly Gln Ile Asn Glu Asn Ala Lys Ala Pro Ala Tyr Phe Asn Val Phe
225                 230                 235                 240

Pro Glu Leu Asn His Asn Glu Ile Val Gly Phe Glu Val Pro Glu Asp
                245                 250                 255

Leu Val Lys Lys Leu Ala Val Ile Ile Leu Arg Asp Pro Asp Asp His
                260                 265                 270

Gly Arg Ile Thr Lys Arg Ile Glu Ile Thr Lys Asp Ile Leu Gln Gly
                275                 280                 285

Lys Val Ser Ser Val Ala Glu Val Glu Ala Arg Gly Asn Ser Phe Leu
                290                 295                 300

Ala Lys Thr Tyr Ser Leu Ile Tyr Val Gly Asp Tyr Ala Ser Val Tyr
305                 310                 315                 320

Leu Ala Glu Leu Tyr Gly Ile Asn Pro Thr Pro Val Gln Val Ile Asp
                325                 330                 335

Tyr Leu Lys Ala Arg Met Ala Glu
                340

<210> SEQ ID NO 16
<211> LENGTH: 328
<212> TYPE: PRT
<213> ORGANISM: Schleiferia thermophila

<400> SEQUENCE: 16

Met Leu Thr Leu Ile Glu Asn Phe Pro Lys His Leu Val Asp Ala Met
1               5                  10                  15

Ile Thr Ala Lys Lys Ala Ser Phe Lys Gln Ser Asn Arg Ala Ile Lys
                20                  25                  30

Asn Val Ile Ile Thr Gly Leu Gly Gly Ser Gly Ile Gly Ala Ser Met
                35                  40                  45

Val Gln Asp Leu Leu Ser Pro His Ala Glu Ile Pro Ile Ile Val Asn
 50                  55                  60
```

Lys Asp Tyr His Leu Pro Ala Phe Ala Asp Glu Asn Thr Leu Val Ile
65                  70                  75                  80

Ala Cys Ser Tyr Ser Gly Glu Thr Glu Thr Leu Ala Ala Leu Ala
            85                  90                  95

Glu Ala Glu Glu His Ser Cys Glu Ile Ala Ile Ile Thr Ser Gly Gly
                100                 105                 110

Thr Leu Leu Gln Met Ala Lys Ser Lys Asn Tyr Asn Tyr Leu Gln Met
            115                 120                 125

Pro Glu Gly Asn Pro Pro Arg Ser Met Ile Gly Tyr Ser Leu Val Tyr
            130                 135                 140

Gln Leu Tyr Met Leu Ala Tyr Tyr Gly Ile Ser Arg Leu Ala Leu Asp
145                 150                 155                 160

Asn Asp Ile Ile Leu Ser Ser Asn Tyr Leu Leu Glu Phe Arg Glu Lys
                165                 170                 175

Ile Gln Ser Gln Ala Arg Tyr Ile Ala Val Arg Leu His Lys Lys Ile
            180                 185                 190

Pro Ala Val Tyr Ala Cys Ser Gly Phe Gly Ser Leu Ala Glu Arg Phe
            195                 200                 205

Arg Gln Gln Leu Asn Glu Asn Ser Lys Met Leu Ala Trp Asn Gly Thr
210                 215                 220

Val Pro Glu Met Asn His Asn Glu Leu Val Gly Trp Lys Gly Gly Asp
225                 230                 235                 240

Glu His Phe Ala Ala Ile Phe Ile His Thr Pro Phe Asp Asp Asn Arg
                245                 250                 255

Asn Ala Lys Arg Thr Glu Ile Ser Ser Asn Ile Ile Gln Asn Phe Thr
            260                 265                 270

Ser Gly Val Phe His Ile His Ser Glu Gly Glu Thr Pro Leu Arg Ala
            275                 280                 285

Phe Phe Tyr Leu Ile His Ile Thr Asp Trp Ile Ser Tyr Tyr Leu Ser
            290                 295                 300

Glu Leu Asn Gly Val Asp Val Met Asp Ile Ser Ala Ile Asn Gln Leu
305                 310                 315                 320

Lys Gly Glu Leu Ala Asn Phe Asn
                325

<210> SEQ ID NO 17
<211> LENGTH: 349
<212> TYPE: PRT
<213> ORGANISM: Thermodesulfobium narugense

<400> SEQUENCE: 17

Met Asp Lys Asn Val Met Asn Ser Tyr Val Ser Asp Ile Ala Tyr His
1               5                   10                  15

Met Lys Asp Phe Tyr Lys Asp Leu Thr Phe Tyr Lys Asp Gly Lys Ile
            20                  25                  30

Asp Leu Asn Glu Ile Glu Asn Leu Ile Phe Leu Gly Ile Gly Gly Ser
            35                  40                  45

Ala Ile Ser Pro Lys Ile Phe Thr Glu Ile Met Asn Ile Asn Lys Lys
50                  55                  60

Val Tyr Phe Phe Ser Thr Leu Asn Gly Phe Glu Ala Leu Pro Asp Pro
65                  70                  75                  80

Ser Thr Ser Phe Val Ile Ala Phe Ser Tyr Ser Gly Asn Thr Val Glu
            85                  90                  95

Thr Leu Arg Ser Ile Glu Leu Ile Ala Lys Asp Arg Phe Arg Gly Ile
            100                 105                 110

Gly Ile Ser Ser Gly Gly Lys Ile Val Asp Leu Cys Lys Ser Leu Asn
            115                 120                 125

Trp Gln His Ile Ala Val Pro Lys Gly Arg Ala Pro Arg Ala Ala Met
    130                 135                 140

Pro Phe Thr Leu Ser Ile Leu Phe Lys Leu Ala Leu Ser Lys Gly Trp
145                 150                 155                 160

Thr Glu Tyr Asn Glu Asp Asp Phe Trp Asn Asp Ile Ile Glu Leu Ser
                165                 170                 175

Asn Ser Lys Asn Asn Phe Leu Pro Glu Val Asp Phe Glu Asp Asn Val
            180                 185                 190

Ser Lys Arg Ile Ala Tyr Lys Leu Ala Thr Lys Lys Asn Val Ile Ile
        195                 200                 205

Trp Gly Val Glu Ser Ile Ser Lys Asn Ile Ala Tyr Arg Phe Lys Ser
    210                 215                 220

Gln Leu Glu Glu Asn Ala Lys Gln Leu Ser Tyr Tyr Ser Tyr Leu Pro
225                 230                 235                 240

Glu Ala Ser His Asn Gln Ile Val Pro Ile Ser Leu Val Asp Asn Lys
                245                 250                 255

Glu Glu Tyr Ile Val Leu Ile Phe Arg Ile Pro Gln Leu Glu Ser Val
            260                 265                 270

Leu Val Ser Asn Ile Ile Ser Thr Val Lys Thr Phe Leu Asn Ser Glu
        275                 280                 285

Gly Ile Glu Val Leu Glu Val Phe Gly Ser Gly Lys Asn His Val Leu
    290                 295                 300

Ala Gly Leu Asp Leu Ile Tyr Ser Thr Asp Phe Val Ser Tyr Tyr Leu
305                 310                 315                 320

Ala Leu Leu Lys Gly Ile Glu Pro Glu Pro Ile Glu Pro Ile Ser Arg
                325                 330                 335

Met Lys Val Ile Leu Asn Asp Asn Leu Arg Lys Ala Leu
            340                 345

<210> SEQ ID NO 18
<211> LENGTH: 141
<212> TYPE: PRT
<213> ORGANISM: Lactococcus lactis

<400> SEQUENCE: 18

Met Ala Ile Val Val Gly Ala Asp Leu Lys Gly Thr Arg Leu Lys Asp
1               5                   10                  15

Val Val Lys Asn Phe Leu Val Glu Glu Gly Phe Glu Val Ile Asp Val
            20                  25                  30

Thr Lys Asp Gly Gln Asp Phe Val Asp Val Thr Leu Ala Val Ala Ser
        35                  40                  45

Glu Val Asn Lys Asp Glu Gln Asn Leu Gly Ile Val Ile Asp Ala Tyr
    50                  55                  60

Gly Ala Gly Pro Phe Met Val Thr Lys Ile Lys Gly Met Val Ala
65                  70                  75                  80

Ala Glu Val Ser Asp Glu Arg Ser Ala Tyr Met Thr Arg Gly His Asn
                85                  90                  95

Asn Ala Arg Met Ile Thr Val Gly Ala Glu Ile Val Gly Asp Glu Leu
            100                 105                 110

Ala Lys Asn Ile Ala Lys Ala Phe Val Asn Gly Lys Tyr Asp Gly Gly
        115                 120                 125

Arg His Gln Val Arg Val Asp Met Leu Asn Lys Met Cys

<210> SEQ ID NO 19
<211> LENGTH: 312
<212> TYPE: PRT
<213> ORGANISM: Lactococcus lactis

<400> SEQUENCE: 19

Met Arg Ile Ala Ile Gly Cys Asp His Ile Val Thr Asp Val Lys Met
1               5                   10                  15

Ala Val Ser Glu Phe Leu Lys Ser Lys Gly Tyr Glu Val Leu Asp Phe
            20                  25                  30

Gly Thr Tyr Asp His Val Arg His Tyr Pro Ile Tyr Gly Lys Lys
        35                  40                  45

Val Gly Glu Ala Val Val Ser Gly Gln Ala Asp Leu Gly Val Cys Ile
    50                  55                  60

Cys Gly Thr Gly Val Gly Ile Asn Asn Ala Val Asn Lys Val Pro Gly
65                  70                  75                  80

Val Arg Ser Ala Leu Val Arg Asp Met Thr Ser Ala Leu Tyr Ala Lys
                85                  90                  95

Glu Glu Leu Asn Ala Asn Val Ile Gly Phe Gly Gly Met Ile Thr Gly
            100                 105                 110

Gly Leu Leu Met Asn Asp Ile Ile Glu Ala Phe Ile Glu Ala Glu Tyr
        115                 120                 125

Lys Pro Thr Glu Glu Asn Lys Lys Leu Ile Ala Lys Ile Glu His Val
    130                 135                 140

Glu Thr His Asn Ala His Gln Ala Asp Glu Glu Phe Phe Thr Glu Phe
145                 150                 155                 160

Leu Glu Lys Trp Asp Arg Gly Glu Tyr His Asp Met Ala Ile Val Val
                165                 170                 175

Gly Ala Asp Leu Lys Gly Thr Arg Leu Lys Asp Val Val Lys Asn Phe
            180                 185                 190

Leu Val Glu Glu Gly Phe Glu Val Ile Asp Val Thr Lys Asp Gly Gln
        195                 200                 205

Asp Phe Val Asp Val Thr Leu Ala Val Ala Ser Glu Val Asn Lys Asp
    210                 215                 220

Glu Gln Asn Leu Gly Ile Val Ile Asp Ala Tyr Gly Ala Gly Pro Phe
225                 230                 235                 240

Met Val Ala Thr Lys Ile Lys Gly Met Val Ala Ala Glu Val Ser Asp
                245                 250                 255

Glu Arg Ser Ala Tyr Met Thr Arg Gly His Asn Asn Ala Arg Met Ile
            260                 265                 270

Thr Val Gly Ala Glu Ile Val Gly Asp Glu Leu Ala Lys Asn Ile Ala
        275                 280                 285

Lys Ala Phe Val Asn Gly Lys Tyr Asp Gly Gly Arg His Gln Val Arg
    290                 295                 300

Val Asp Met Leu Asn Lys Met Cys
305                 310

<210> SEQ ID NO 20
<211> LENGTH: 270
<212> TYPE: PRT
<213> ORGANISM: Bacteroides thetaiotaomicron

<400> SEQUENCE: 20

Met Lys Tyr Lys Leu Ile Val Leu Asp Leu Asp Gly Thr Leu Thr Asn

-continued

```
              1               5              10              15
            Ser Lys Lys Glu Ile Ser Ser Arg Asn Arg Glu Thr Leu Ile Arg Ile
                            20                  25                  30

Gln Glu Gln Gly Ile Arg Leu Val Leu Ala Ser Gly Arg Pro Thr Tyr
                            35                  40                  45

Gly Ile Val Pro Leu Ala Asn Glu Leu Arg Met Asn Glu Phe Gly Gly
                            50                  55                  60

Phe Ile Leu Ser Tyr Asn Gly Gly Ile Ile Asn Trp Glu Ser Lys
             65                  70                  75                  80

Glu Met Met Tyr Glu Asn Val Leu Pro Asn Glu Val Val Pro Val Leu
                            85                  90                  95

Tyr Glu Cys Ala Arg Thr Asn His Leu Ser Ile Leu Thr Tyr Asp Gly
                            100                 105                 110

Ala Glu Ile Val Thr Glu Asn Ser Leu Asp Pro Tyr Val Gln Lys Glu
                            115                 120                 125

Ala Phe Leu Asn Lys Met Ala Ile Arg Glu Thr Asn Asp Phe Leu Thr
                            130                 135                 140

Asp Ile Thr Leu Pro Val Ala Lys Cys Leu Ile Val Gly Asp Ala Gly
            145                 150                 155                 160

Lys Leu Ile Pro Val Glu Ser Glu Leu Cys Ile Arg Leu Gln Gly Lys
                            165                 170                 175

Ile Asn Val Phe Arg Ser Glu Pro Tyr Phe Leu Glu Leu Val Pro Gln
                            180                 185                 190

Gly Ile Asp Lys Ala Leu Ser Leu Ser Val Leu Leu Glu Asn Ile Gly
                            195                 200                 205

Met Thr Arg Glu Glu Val Ile Ala Ile Gly Asp Gly Tyr Asn Asp Leu
                            210                 215                 220

Ser Met Ile Lys Phe Ala Gly Met Gly Val Ala Met Gly Asn Ala Gln
            225                 230                 235                 240

Glu Pro Val Lys Lys Ala Ala Asp Tyr Ile Thr Leu Thr Asn Asp Glu
                            245                 250                 255

Asp Gly Val Ala Glu Ala Ile Glu Arg Ile Phe Asn Val Pro
                            260                 265                 270
```

<210> SEQ ID NO 21
<211> LENGTH: 217
<212> TYPE: PRT
<213> ORGANISM: Halothermothrix orenii

<400> SEQUENCE: 21

```
            Met Ile Glu Ala Val Ile Phe Asp Met Asp Gly Val Ile Ile Asn Ser
             1               5              10                      15

Glu Pro Ile His Tyr Lys Val Asn Gln Ile Ile Tyr Glu Lys Leu Gly
                            20                  25                  30

Ile Lys Val Pro Arg Ser Glu Tyr Asn Thr Phe Ile Gly Lys Ser Asn
                            35                  40                  45

Thr Asp Ile Trp Ser Phe Leu Lys Arg Lys Tyr Asn Leu Lys Glu Ser
             50                  55                  60

Val Ser Ser Leu Ile Glu Lys Gln Ile Ser Gly Asn Ile Lys Tyr Leu
             65                  70                  75                  80

Lys Ser His Glu Val Asn Pro Ile Pro Gly Val Lys Pro Leu Leu Asp
                            85                  90                  95

Glu Leu Ser Glu Lys Gln Ile Thr Thr Gly Leu Ala Ser Ser Pro
                            100                 105                 110
```

```
Glu Ile Tyr Ile Glu Thr Val Leu Glu Glu Leu Gly Leu Lys Ser Tyr
        115             120                 125

Phe Lys Val Thr Val Ser Gly Glu Thr Val Ala Arg Gly Lys Pro Glu
    130             135                 140

Pro Asp Ile Phe Glu Lys Ala Ala Arg Ile Leu Gly Val Glu Pro Pro
145             150                 155                 160

His Cys Val Val Ile Glu Asp Ser Lys Asn Gly Val Asn Ala Ala Lys
            165                 170                 175

Ala Ala Gly Met Ile Cys Ile Gly Tyr Arg Asn Glu Glu Ser Gly Asp
            180             185                 190

Gln Asp Leu Ser Ala Ala Asp Val Val Val Asp Ser Leu Glu Lys Val
        195             200                 205

Asn Tyr Gln Phe Ile Lys Asp Leu Ile
        210             215
```

ENZYMATIC PRODUCTION OF HEXOSES

CROSS REFERENCE TO RELATED APPLICATIONS

This application claims priority to U.S. Application No. 62/470,605, filed on Mar. 13, 2017, U.S. Application No. 62/470,620, filed on Mar. 13, 2017, U.S. Application No. 62/482,148, filed on Apr. 5, 2017, and U.S. Application No. 62/480,798, filed on Apr. 3, 2017, which are hereby incorporated by reference in their entirety.

REFERENCE TO AN ELECTRONIC SEQUENCE LISTING

The contents of the electronic sequence listing created on Sep. 12, 2019, named 2019-09-12 Sequence Listing.txt and 50,531 bytes in size, is hereby incorporated by reference in its entirety.

FIELD OF THE INVENTION

The invention relates to preparation of hexose monosaccharides. More specifically, the invention relates to methods of preparing a D-hexose (or hexose) from saccharides (e.g., polysaccharides, oligosaccharides, disaccharides, sucrose, D-glucose, and D-fructose) including a step in which fructose 6-phosphate is converted to the hexose by one or more enzymatic steps.

BACKGROUND

Hexoses are monosaccharides with six carbon atoms. Hexoses can be classified by functional group, with aldohexoses having an aldehyde at position 1, and ketohexoses having that ketone at position 2. Aldohexoses (or aldoses) include allose, altrose, glucose, gulose, galactose, idose, talose, and mannose. Ketohexoses (or ketoses) include psicose (allulose), fructose, tagatose, and sorbose. Various aspects of these aldohexoses and ketohexoses are mentioned in the following paragraphs.

For example, D-allose (allose hereafter) is a low-calorie, natural sweetener that has ~80% the sweetness of sucrose and is described as a noncaloric sweetening and bulking agent. It is a naturally occurring monosaccharide hexose that is present in only small amounts in specific shrubs and algae. Allose boasts several potential medical and agriculture benefits including cryoprotective, anti-oxidative, anti-hypertensive, immunosuppressive, anti-inflammatory, anti-tumor, and anti-cancer activities. It also has similar functionality in foods and beverages to sucrose. As such, allose clearly has a variety of applications in the food and beverage industries. However, due to allose's high selling prices, its use as a sweetener has been limited.

Currently allose is produced predominantly through the enzymatic isomerization of D-psicose (WO 2014069537). Overall, the method suffers because of higher feedstock cost, the costly separation of allose from D-psicose, and relatively low product yields (~23%).

Altrose is another unnatural aldohexose and C-3 epimer of mannose. D-Altrose ((2S,3R,4R,5R)-2,3,4,5,6-Pentahydroxyhexanal) can be used as a substrate to identify, differentiate and characterize aldose isomerases such as L-fucose isomerase from *Caldicellulosiruptor saccharolyticus* and d-Arabinose isomerase (d-AI) from *Bacillus pallidus* (*B. pallidus*) and *Klebsiella pneumoniae*. Recently, sugar chains such as oligosaccharides and polysaccharides, which perform functions useful as a physiologically active substance, have attracted attention in the field of fine chemicals such as medicines and agricultural chemicals. Presently, the objects of researches on the sugar chain are restricted to those consisting of monosaccharides present in nature in large amounts and readily available to researchers, such as D-glucose, D-mannose and D-galactose. However, it is expected that various monosaccharides other than those present in nature will be required in the future in research on the synthesis of sugar chains performing more useful functions. Under the circumstances, it is highly significant and necessary to develop a method which permits preparing D-altrose, which is a rare sugar difficult to obtain, in high yield while diminishing the number of treating steps. U.S. Pat. No. 5,410,038.

D-Gulose is useful, for example, as an excipient, a chelating agent, a pharmaceutical intermediate, a cleaning agent for glass and metals, a food additive, and as an additive for detergents. U.S. Pat. No. 5,215,591.

D-galactose (galactose hereafter) is a natural sweetener that has ~33% the sweetness of sucrose and is described as a nutritive sweetener. It is a naturally occurring monosaccharide hexose that is present in dairy products, legumes, grains, nuts, tubers and vegetables. Galactose is used by the baking industry to limit tartness and acidity in foods. Also, it is used as an energy source to increase endurance in the exercise supplement industry. In the pharmaceutical industry it is an intermediate for several medicines and is also used as a cell metabolism modulator in the optimization of protein therapeutics bioproduction. Additionally, galactose has been shown to be effective as a control agent against plant disease caused by certain plant pathogens, such as those affecting cucumber, carrot, potato and tomato plants. Due to dietary concerns (e.g. veganism) and health concerns (e.g. BSE disease) non-animal sources of galactose are of interest to industry. As such, galactose clearly has a variety of applications in the food, beverage, exercise, agriculture, and pharmaceutical industries. However, due to galactose's high selling prices, its use has been limited.

Galactose is produced predominantly through the hydrolysis of lactose (WO 2005039299A3). This method is less desirable due to a more costly feed stock and the expensive separation of glucose from galactose. Alternatively, galactose can be produced via the hydrolysis of plant-based biomass (WO 2005001145A1). This method suffers from the costly separation of galactose from the multiple other sugars released during biomass hydrolysis (e.g. xylose, arabinose, mannose, glucose, and rhamnose) and low yields (~4.6% of the dry mass of common biomass sources is galactose).

Idose is not found in nature, but its uronic acid, iduronic acid, is important. It is a component of dermatan sulfate and heparan sulfate, which are glycosaminoglycans. (en.wikipedia.org/wiki/Idose-accessed 3/7/18).

Talose is an unnatural aldohexose that is soluble in water and slightly soluble in methanol. It is a C-2 epimer of galactose and C-4 epimer of mannose. Talose can be used as a substrate to identify, differentiate, and characterize ribose-5-phosphate isomerase(s) of Clostridia.

D-mannose (mannose hereafter) is a mildly sweet, naturally-occurring monosaccharide that is found in many fruits, vegetables, plant materials, and even the human body. Mannose boasts multiple health benefits and pharmaceutical applications. For example, mannose can be used to treat carbohydrate-deficient glycoprotein syndrome type 1b and, more commonly, urinary tract infections. Furthermore, mannose is a verified prebiotic, does not raise blood glucose levels, and shows anti-inflammatory properties. Additionally, it has been shown to enhance carcass yields in pigs and is a widely used auxiliary moisturizing agent for skin-care products. As such, mannose has a variety of applications in the pharmaceutical, cosmetic, beverage, food product, dairy, confectionery, and livestock industries. However, due to mannose's high selling prices, its use in everyday products has been limited.

Mannose is primarily produced through extraction from plants. Common methods include acid hydrolysis, thermal hydrolysis, enzymatic hydrolysis, microbial fermentation hydrolysis, and mixtures thereof. Less common methods include chemical and biological transformations. Overall, these methods are problematic due to harsh conditions, high capital expenditures, higher feedstock cost, costly separation of mannose from isomerization reactions, and relatively low product yields (15-35%).

D-allulose (also known as D-psicose) (psicose hereafter) is a low-calorie, natural sweetener that has 70% the sweetness of sucrose, but only 10% of the calories. It is a naturally occurring monosaccharide hexose that is present in only small amounts in wheat and other plants. Psicose was approved as a food additive by the Food and Drug Administration (FDA) in 2012, which designated it as generally recognized as safe (GRAS). However, due to psicose's high selling prices, its use as a sweetener has been limited. Psicose boasts a myriad of health benefits: it is low-calorie (10% of sucrose); it has a very low glycemic index of 1; it is fully absorbed in the small intestine but not metabolized and instead secreted in urine and feces; it helps regulate blood sugar by inhibiting alpha-amylase, sucrase and maltase; and it has similar functionality in foods and beverages as sucrose. As such, psicose clearly has a variety of applications in the food and beverage industries.

Currently psicose is produced predominantly through the enzymatic isomerization of fructose (WO 2014049373). Overall, the method exhibits higher feedstock cost, the costly separation of psicose from fructose, and relatively low product yields.

Fructose is a simple ketonic monosaccharide found in many plants, where it is often bonded to glucose to form the disaccharide, sucrose. Commercially, fructose is derived from sugar cane, sugar beets, and maize. The primary reason that fructose is used commercially in foods and beverages, besides its low cost, is its high relative sweetness. It is the sweetest of all naturally occurring carbohydrates. Fructose is also found in the manufactured sweetener, high-fructose corn syrup (HFCS), which is produced by treating corn syrup with enzymes, converting glucose into fructose. (en.wikipedia.org/wiki/Fructose#Physical_and_functional_properties--accessed 3/7/18).

D-tagatose (tagatose hereafter) is a low-calorie, natural sweetener that has 92% the sweetness of sucrose, but only 38% of the calories. It is a naturally occurring monosaccharide hexose that is present in only small amounts in fruits, cacao, and dairy products. Tagatose was approved as a food additive by the Food and Drug Administration (FDA) in 2003, which designated it as generally recognized as safe (GRAS). However, due to tagatose's high selling prices, its use as a sweetener has been limited. Tagatose boasts a myriad of health benefits: it is non-cariogenic; it is low-calorie; it has a very low glycemic index of 3; it attenuates the glycemic index of glucose by 20%; it can lower average blood glucose levels; it helps prevent cardiovascular disease, strokes, and other vascular diseases by raising high-density lipoprotein (HDL) cholesterol; and it is a verified prebiotic and antioxidant. Lu et al., Tagatose, a New Antidiabetic and Obesity Control Drug, Diabetes Obes. Metab. 10(2): 109-34 (2008). As such, tagatose clearly has a variety of applications in the pharmaceutical, biotechnological, academic, food, beverage, dietary supplement, and grocer industries.

Tagatose is produced predominantly through the hydrolysis of lactose by lactase or acid hydrolysis to form D-glucose and D-galactose (WO 2011150556, CN 103025894, U.S. Pat. Nos. 5,002,612, 6,057,135, and 8,802,843). The D-galactose is then isomerized to D-tagatose either chemically by calcium hydroxide under alkaline conditions or enzymatically by L-arabinose isomerase under pH neutral conditions. The final product is isolated by a combination of filtration and ion exchange chromatography. This process is performed in several tanks or bioreactors. Overall, the method is disadvantageous because of the costly separation of other sugars (e.g., D-glucose, D-galactose, and unhydrolyzed lactose) and low product yields. Several methods via microbial cell fermentation are being developed, but none have been proven to be a practical alternative due to their dependence on costly feedstock (e.g., galactitol and D-psicose), low product yields, and costly separation.

Sorbose ((3R,4S,5R)-1,3,4,5,6-pentahydroxyhexan-2-one) is a ketohexose that has a sweetness equivalent to sucrose (table sugar), and it is a plant metabolite that has been found to naturally occur in grapes in small quantities. D-sorbose has been determined to be effective as a control agent of plant diseases caused by: *Pseudomonas syringae* pv. *lachrymans* and *Ralstonia solanacearum*. United States Patent Application Publication No. 2016/0037768.

There is a need to develop cost-effective synthetic pathways for high-yield production of the hexoses such as the aldohexoses and aldoketoses discussed above where at least one step of the processes involves an energetically favorable chemical reaction. Furthermore, there is a need for production processes where the process steps can be conducted in one tank or bioreactor and/or where costly separation steps are avoided or eliminated. There is also a need for processes of hexose production that can be conducted at a relatively low concentration of phosphate, where phosphate can be recycled, and/or the process does not require using adenosine triphosphate (ATP) as an added source of phosphate. There is also a need for hexose production pathways that do not require the use of the costly nicotinamide adenosine dinucleotide (NAD(P)(H)) coenzyme in any of the reaction steps.

SUMMARY OF THE INVENTION

The inventions described herein generally relate to processes for preparing hexoses from saccharides by enzymatic conversion. The inventions also relate to hexoses prepared by any of the processes described herein.

More specifically, the invention relates to processes for preparing a hexose, selected from allose, mannose, galactose, fructose, altrose, talose, sorbose, gulose and idose, from a saccharide, the process comprising: converting fructose 6-phosphate (F6P) to the hexose catalyzed by one or more enzymes selected from an isomerase, an epimerase, and a hexose-specific phosphatase and mixtures thereof.

A process of the invention for the production of allose comprises converting the F6P to psicose 6-phosphate (P6P) catalyzed by psicose 6-phosphate 3-epimerase (P6PE); converting the P6P to allose 6-phosphate (A6P) catalyzed by allose 6-phosphate isomerase (A6PI); and converting the A6P to allose catalyzed by allose 6-phosphate phosphatase (A6PP).

A process of the invention for the production of mannose comprises converting the F6P to mannose 6-phosphate (M6P) catalyzed by mannose 6-phosphate isomerase (M6PI) or phosphoglucose/phosphomannose isomerase (PGPMI); and converting the M6P to mannose catalyzed by mannose 6-phosphate phosphatase (MEPP).

A process of the invention for the production of galactose comprises converting the F6P to tagaose 6-phosphate (T6P) catalyzed by fructose 6-phosphate 4-epimerase (F6PE); converting the T6P to galactose 6-phosphate (Gal6P) catalyzed by galactose 6-phosphate isomerase (Gal6PI); and converting the Gal6P to galactose catalyzed by galactose 6-phosphate phosphatase (Gal6PP).

A process of the invention for the production of fructose comprises converting the F6P to fructose catalyzed by fructose 6-phosphate phosphatase (F6PP).

A process of the invention for the production of altrose comprises converting the F6P to converting the F6P to P6P catalyzed by P6PE; converting the P6P to altrose 6-phosphate (Alt6P) catalyzed by altrose 6-phosphate isomerase (Alt6PI); and converting the Alt6P produced to altrose catalyzed by altrose 6-phosphate phosphatase (Alt6PP).

A process of the invention for the production of talose comprises converting the F6P to T6P catalyzed by F6PE; converting the T6P to talose 6-phosphate (Tal6P) catalyzed by talose 6-phosphate isomerase (Tal6PI); and converting the Tal6P to talose catalyzed by talose 6-phosphate phosphatase (Tal6PP).

A process of the invention for the production of sorbose comprises converting the F6P to T6P catalyzed by F6PE; converting the T6P to sorbose 6-phosphate (S6P) catalyzed by sorbose 6-phosphate epimerase (S6PE); and converting the S6P to sorbose catalyzed by sorbose 6-phosphate phosphatase (S6PP).

A process of the invention for the production of gulose comprises converting the F6P to T6P catalyzed by F6PE; converting the S6P to gulose 6-phosphate (Gul6P) catalyzed by gulose 6-phosphate isomerase (Gul6PI); and converting the Gul6P to gulose catalyzed by gulose 6-phosphate phosphatase (Gul6PP).

A process of the invention for the production of gulose comprises converting the F6P to T6P catalyzed by F6PE; converting the T6P to sorbose 6-phosphate (S6P) catalyzed by sorbose 6-phosphate epimerase (S6PE); converting the S6P to idose 6-phosphate (I6P) catalyzed by idose 6-phosphate isomerase (I6PI); and converting the I6P to idose catalyzed by idose 6-phosphate phosphatase (I6PP).

The processes of hexose production according to the invention can involve a step of converting glucose 6-phosphate (G6P) to the F6P, wherein the step is catalyzed by phosphoglucose isomerase (PGI). The processes can also comprise the step of converting glucose 1-phosphate (G1P) to the G6P, wherein the step is catalyzed by phosphoglucomutase (PGM). Additionally, the processes according to the invention may further comprise the step of converting a saccharide to the G1P, where the step is catalyzed by at least one enzyme, and the saccharide is selected from the group consisting of a starch or derivative thereof, cellulose or a derivative thereof, and sucrose.

The enzyme or enzymes used in the step of converting a saccharide to the G1P in the processes according to the invention can be alpha-glucan phosphorylase (αGP), maltose phosphorylase, sucrose phosphorylase, cellodextrin phosphorylase, cellobiose phosphorylase, and/or cellulose phosphorylase, and mixtures thereof. When the saccharide is starch or a starch derivative, the derivative may be selected from the group consisting of amylose, amylopectin, soluble starch, amylodextrin, maltodextrin, maltose, and glucose, and mixtures thereof.

Some processes according to the invention, may further comprise the step of converting starch to a starch derivative, where the starch derivative is prepared by enzymatic hydrolysis of starch or by acid hydrolysis of starch. Also, 4-glucan transferase (4GT) can be added to the processes. 4GT can be used to increase hexose yields by recycling the degradation products glucose, maltose, and maltotriose into longer maltooligosaccharides; which can be phosphorolytically cleaved by αGP to yield G1P.

Where the processes use a starch derivative, the starch derivative can be prepared by enzymatic hydrolysis of starch catalyzed by isoamylase, pullulanase, alpha-amylase, or their combination.

The process according to the inventions can also comprise the step of converting fructose to the F6P, wherein the step is catalyzed by at least one enzyme and, optionally, the step of converting sucrose to the fructose, wherein the step is catalyzed by at least one enzyme.

Furthermore, the processes of producing a hexose according to the inventions can comprise the step of converting glucose to the G6P, where the step is catalyzed by at least one enzyme, and, optionally, the step of converting sucrose to the glucose that is catalyzed by at least one enzyme.

The steps in each of the processes of hexose synthesis according to the invention can be conducted at a temperature ranging from about 40° C. to about 90° C. and at a pH ranging from about 5.0 to about 8.0. They may be conducted for about 8 hours to about 48 hours.

The steps of the processes according to the inventions can be conducted in a single bioreactor. The steps can also be conducted in a plurality of bioreactors arranged in series.

The enzymatic process steps of the inventions may be conducted ATP-free and/or NAD(P)(H)-free. The steps can be carried out at a phosphate concentration ranging from about 0.1 mM to about 150 mM. The phosphate used in the phosphorylation and dephosphorylation steps of the processes according to the inventions can be recycled. At least one step of the processes may involve an energetically favorable chemical reaction.

The invention also relates to allose, mannose, galactose, fructose, altrose, talose, sorbose, gulose and idose produced by these processes.

DESCRIPTION OF THE INVENTION

Figure 1:
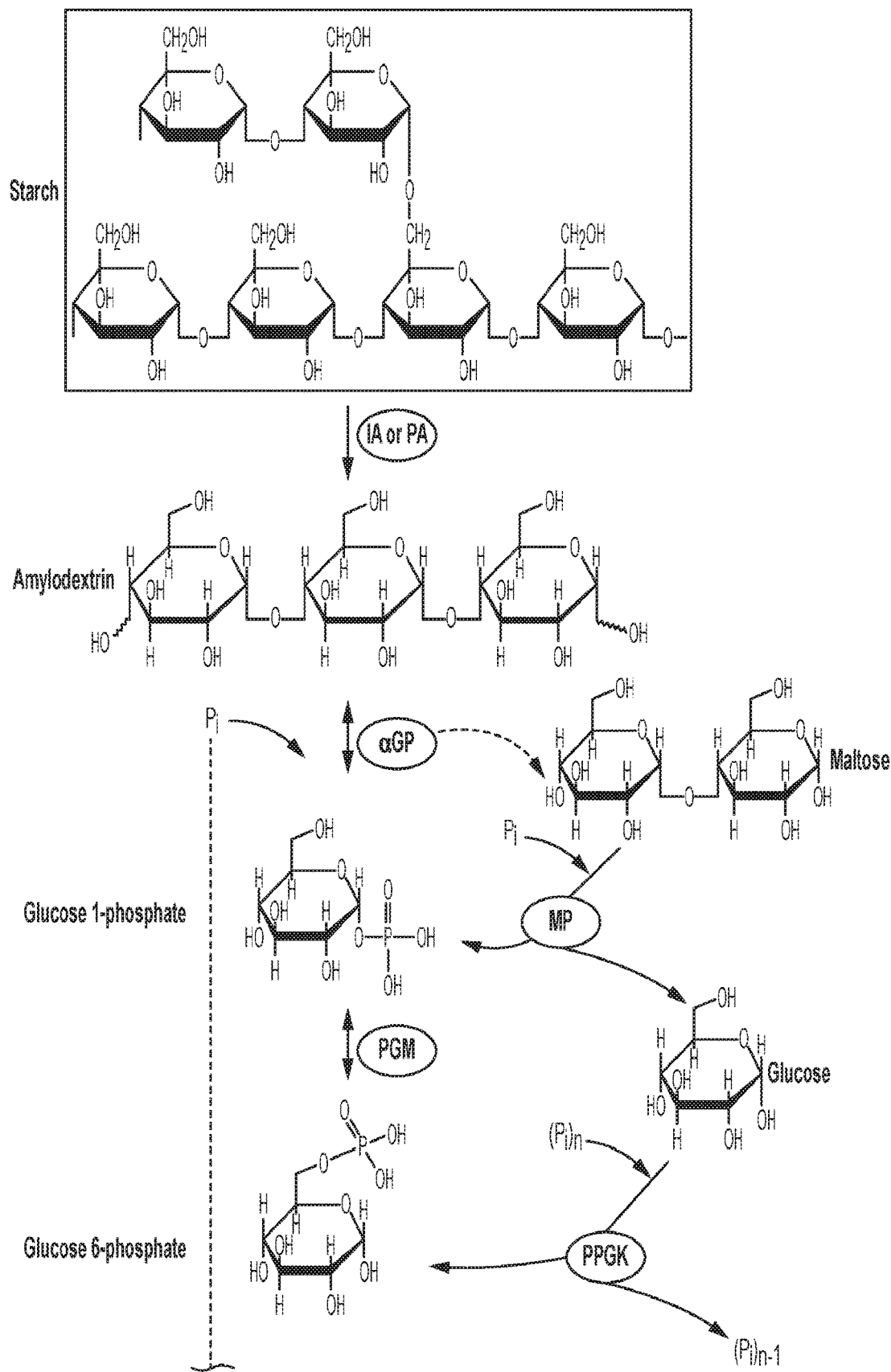
FIG. 1 is a schematic diagram showing an enzymatic pathway converting starch or its derived products to allose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; P6PE, psicose 6-phosphate 3-epimerase; A6PI, allose 6-phosphate isomerase; A6PP, allose 6-phosphate phosphatase.
Figure 1:
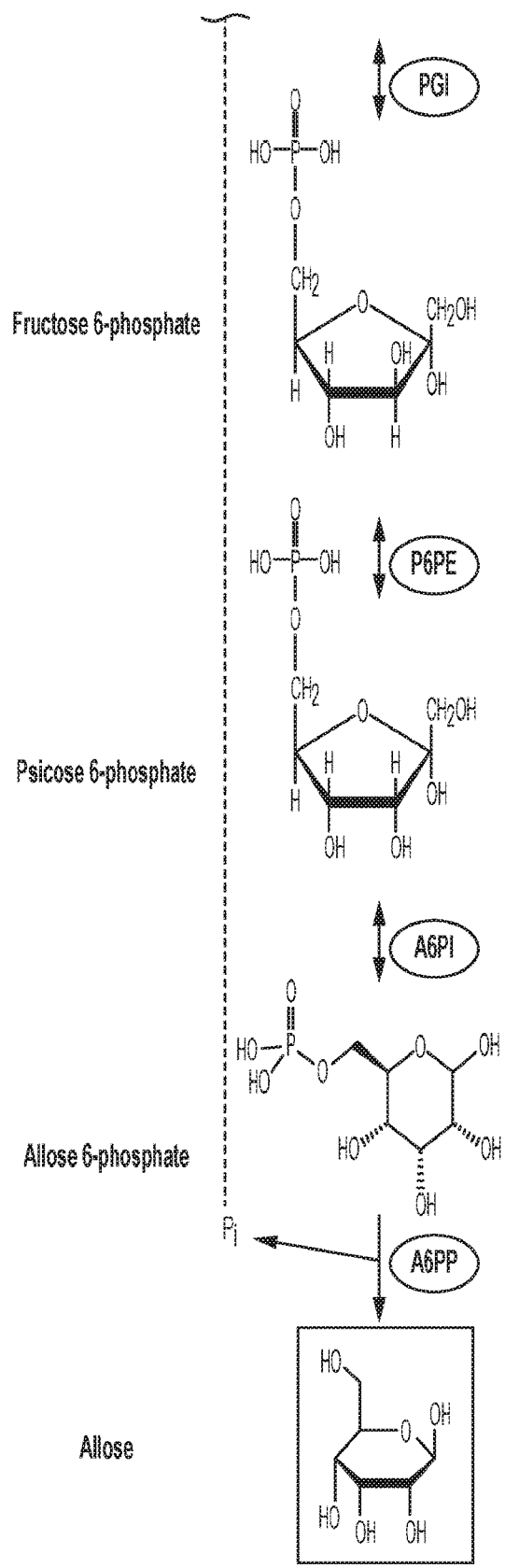

The inventions described herein provide enzymatic pathways, or processes, for synthesizing hexoses with a high product yield, while greatly decreasing the product separation costs and hexose production costs. Also described herein are hexoses produced by these process.

Processes according to the invention for preparing a hexose from a saccharide, comprise: converting fructose 6-phosphate (F6P) to the hexose, catalyzed by one or more enzymes, wherein the hexose is selected from the group consisting of allose, mannose, galactose, fructose, altrose, talose, sorbose, gulose and idose; and wherein the enzymes are selected from the group consisting of an isomerase, an epimerase, and a hexose-specific phosphatase, and mixtures thereof.

One of the important advantages of the processes of the invention is that the process steps can be conducted in a single bioreactor or reaction vessel. Alternatively, the steps can also be conducted in a plurality of bioreactors, or reaction vessels, that are arranged in series.

Phosphate ions produced during the dephosphorylation step can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the hexose making processes.

For example, reaction phosphate concentrations in each of the processes can range from about 0.1 mM to about 300 mM, from about 0 mM to about 150 mM, from about 1 mM to about 50 mM, preferably from about 5 mM to about 50 mM, or more preferably from about 10 mM to about 50 mM. For instance, the reaction phosphate concentration in each of the processes can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Low phosphate concentration results in decreased production costs due to low total phosphate and thus lowered cost of phosphate removal. It also prevents inhibition of phosphatases by high concentrations of free phosphate and decreases the potential for phosphate pollution.

Furthermore, each of the processes disclosed herein can be conducted without added ATP as a source of phosphate, i.e., ATP-free. Each of the processes can also be conducted without having to add NAD(P)(H), i.e., NAD(P)(H)-free. Other advantages also include the fact that at least one step of the disclosed processes for making a hexose involves an energetically favorable chemical reaction.

Examples of the enzymes used to convert a saccharide to G1P include alpha-glucan phosphorylase (αGP, EC 2.4.1.1), maltose phosphorylase (MP, EC 2.4.1.8), cellodextrin phosphorylase (CDP, EC 2.4.1.49), cellobiose phosphorylase (CBP, EC 2.4.1.20), cellulose phosphorylase, sucrose phosphorylase (SP, EC 2.4.1.7), and a combination thereof. The choice of the enzyme or enzyme combination depends on the saccharide used in the process.

The saccharides used for generating G1P can be polysaccharides, oligosaccharides, and/or disaccharides. For example, the saccharide can be starch, one or more derivatives of starch, cellulose, one or more derivatives of cellulose, sucrose, one or more derivatives of sucrose, or a combination thereof.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

Methods of preparing F6P from starch and its derivatives, cellulose and its derivatives, and sucrose and its derivatives can be found, for example in International Patent Application Publication No. WO 2017/059278.

The derivatives of starch can be prepared by enzymatic hydrolysis of starch or by acid hydrolysis of starch. Specifically, the enzymatic hydrolysis of starch can be catalyzed or enhanced by isoamylase (IA, EC. 3.2.1.68), which hydrolyzes α-1,6-glucosidic bonds; pullulanase (PA, EC. 3.2.1.41), which hydrolyzes α-1,6-glucosidic bonds; 4-α-glucanotransferase (4GT, EC. 2.4.1.25), which catalyzes the transglycosylation of short maltooligosaccharides, yielding longer maltooligosaccharides; or alpha-amylase (EC 3.2.1.1), which cleaves α-1,4-glucosidic bonds.

Furthermore, derivatives of cellulose can be prepared by enzymatic hydrolysis of cellulose catalyzed by cellulase mixtures, by acids, or by pretreatment of biomass.

Enzymes used to convert a saccharide to G1P may contain αGP. In this step, when the saccharides include starch, the G1P is generated from starch by αGP; when the saccharides contain soluble starch, amylodextrin, or maltodextrin, the G1P is produced from soluble starch, amylodextrin, or maltodextrin by αGP.

When the saccharides include maltose and the enzymes contain maltose phosphorylase, the G1P is generated from maltose by maltose phosphorylase. If the saccharides include sucrose, and enzymes contain sucrose phosphorylase, the G1P is generated from sucrose by sucrose phosphorylase.

When the saccharides include cellobiose, and the enzymes contain cellobiose phosphorylase, the G1P may be produced from cellobiose by cellobiose phosphorylase.

When the saccharides contain cellodextrins and the enzymes include cellodextrin phosphorylase, the G1P can be generated from cellodextrins by cellodextrin phosphorylase.

In converting a saccharide to G1P, when the saccharides include cellulose, and enzymes contain cellulose phosphorylase, the G1P may be generated from cellulose by cellulose phosphorylase.

According to the invention, a hexose can also be produced from fructose. For example, the process involves generating F6P from fructose and polyphosphate catalyzed by polyphosphate fructokinase (PPFK); converting F6P to T6P catalyzed by F6PE; and converting T6P to tagatose catalyzed by T6PP. The fructose can be produced, for example, by an enzymatic conversion of sucrose.

A hexose can be produced from sucrose. The process, for example, provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; and converting T6P to tagatose catalyzed by T6PP.

The phosphatase used in the processes of the invention is specific for the hexose. For example, allose 6-phosphate is converted to allose by allose 6-phosphate phosphatase; mannose 6-phosphate is converted to mannose by mannose 6-phosphate phosphatase; galactose 6-phosphate is converted to galactose by galactose 6-phosphate phosphatase; fructose 6-phosphate is converted to fructose by fructose 6-phosphate phosphatase; altrose 6-phosphate is converted to altrose by altrose 6-phosphate phosphatase; talose 6-phosphate is converted to talose by talose 6-phosphate phosphatase; sorbose 6-phosphate is converted to sorbose by sorbose 6-phosphate phosphatase; gulose 6-phosphate is converted to gulose by gulose 6-phosphate phosphatase; and idose 6-phosphate is converted to idose by idose 6-phosphate phosphatase. As used herein, specific means having a higher specific activity for the indicated hexose over other hexoses. For instance, allose 6-phosphate phosphatase has a higher specific activity on allose 6-phosphate than, for example, sorbose 6-phosphate or talose 6-phosphate.

The phosphate ions generated during the hexose dephosphorylation step can then be recycled in the step of converting sucrose to G1P. Additionally, PPFK and polyphosphate can be used to increase hexose yields by producing F6P from fructose generated by the phosphorolytic cleavage of sucrose by SP.

A process for preparing a hexose can include the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above. G6P may be produced from glucose and sodium polyphosphate by polyphosphate glucokinase.

The invention provides processes for converting saccharides, such as polysaccharides and oligosaccharides in starch, cellulose, sucrose and their derived products, to a hexose. Artificial (non-natural) ATP-free enzymatic pathways may be provided to convert starch, cellulose, sucrose, and their derived products to a hexose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to a hexose and enhanced solubility.

Maltose phosphorylase (MP) can be used to increase hexose yields by phosphorolytically cleaving the degradation product maltose into G1P and glucose. Alternatively, 4-glucan transferase (4GT) can be used to increase hexose yields by recycling the degradation products glucose, maltose, and maltotriose into longer maltooligosaccharides; which can be phosphorolytically cleaved by αGP to yield G1P.

Additionally, cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

Cellulose and its derived products can be converted to a hexose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partially hydrolyzed by using concentrated acids, including hydrochloric acid, sulfuric acid, phosphoric acid and their combinations.

Polyphosphate and polyphosphate glucokinase (PPGK) can be added to the processes according to the invention, thus increasing yields of a hexose by phosphorylating the degradation product glucose to G6P.

A hexose can be generated from glucose. The processes for hexose production may involve the steps of generating G6P from glucose and polyphosphate catalyzed by polyphosphate glucokinase (PPGK) and converting G6P to F6P catalyzed by PGI.

Any suitable biologically compatible buffering agent known in the art can be used in each of the processes of the invention, such as HEPES, PBS, BIS-TRIS, MOPS, DIPSO, Trizma, etc. The reaction buffer for the processes according to the invention can have a pH ranging from 5.0-8.0. More preferably, the reaction buffer pH can range from about 6.0 to about 7.3. For example, the reaction buffer pH can be 6.0, 6.2, 6.4, 6.6, 6.8, 7.0, 7.2, or 7.3.

The reaction buffer can also contain metal cations. Examples of the metal ions include $Mg^{2+}$ and $Zn^{2+}$. As known in the art, suitable salts may be used to introduce the desired metal cation.

In each of the processes of the invention the reaction temperature at which the process steps are conducted can range from 37-95° C. More preferably, the steps can be conducted at a temperature ranging from about 40° C. to about 90° C. The temperature can be, for example, about 40° C., about 45° C., about 50° C., about 55° C., about 60° C., about 65° C., about 70° C., about 75° C., about 80° C., about 85° C., or about 90° C. Preferably, the reaction temperature is about 50° C.

The reaction time of each of the disclosed processes can be adjusted as necessary, and can range from about 8 hours to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

Typically, the ratios of enzyme units used in each of the disclosed processes are 1:1 to 1:1:1:1:1 (depending on the number of catalyzed steps in the process). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1, 4-glycosidic bonds. A ratio of enzymes, for example, 3:1:1:1:3 can be used to further increase the reaction rate. Therefore, the enzyme ratios, including other optional enzymes discussed below, can be varied to increase the efficiency of hexose production. For example, a particular enzyme may be present in an amount about 2×, 3×, 4×, 5×, etc. relative to the amount of other enzymes.

Figure 11:
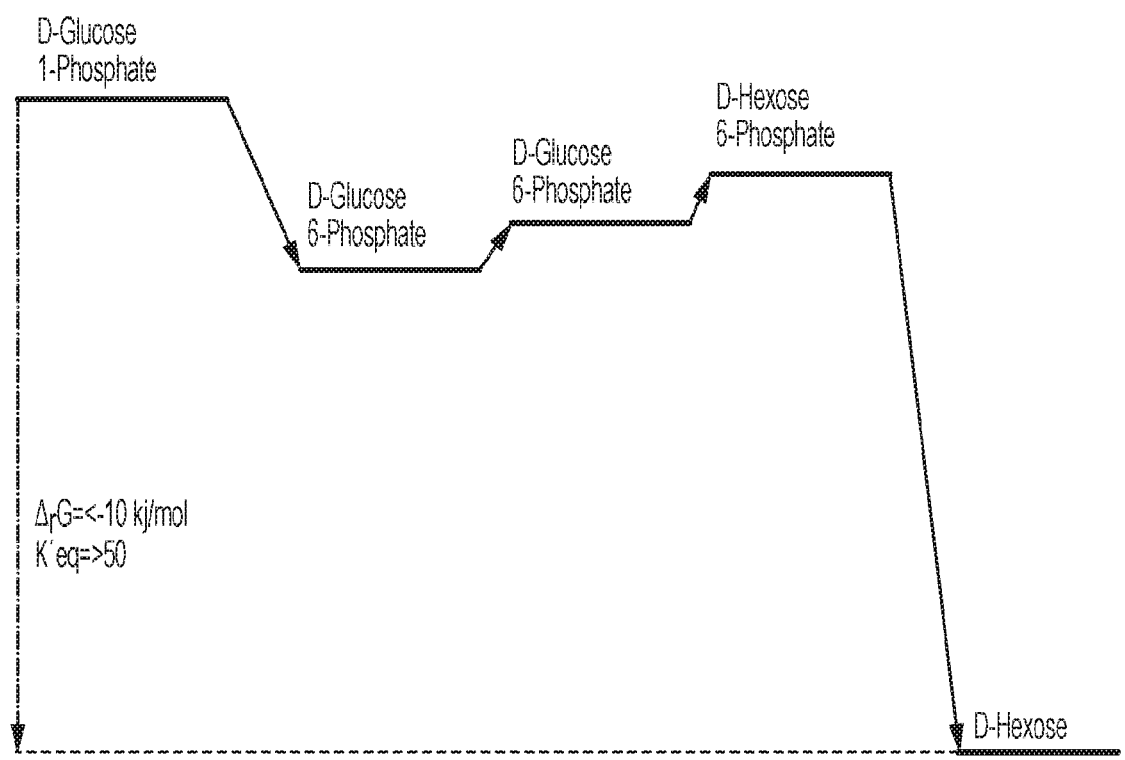
FIG. 11 shows the Reaction Gibbs Energy between intermediates based on formation Gibbs energy for the conversion of glucose 1-phosphate to another hexose.

Each of the processes according to the invention can achieve high yields due to the very favorable equilibrium constant for the overall reaction. For example, FIG. 11 shows the Reaction Gibbs Energy between intermediates based on formation Gibbs energy for the conversion of glucose 1-phosphate to a hexose. Reaction Gibbs Energies were generated using equilibrator.weizmann.ac.il/. Theoretically, up to 99% yields can be achieved if the starting material is completely converted to an intermediate.

Processes of the invention use low-cost starting materials and reduce production costs by decreasing costs associated with the feedstock and product separation. Starch, cellulose, sucrose and their derivatives are less expensive feedstocks than, for example, lactose. When a hexose is produced from lactose, glucose and other hexose(s) are separated via chromatography, which leads to higher production costs.

Also, the step of hexose dephosphorylation by a phosphatase according to the invention is an irreversible phosphatase reaction, regardless of the feedstock. Therefore, hexose is produced with a very high yield while effectively minimizing the subsequent product separation costs.

In some aspects of the invention, phosphatases to convert A6P, M6P, F6P, or Gal6P to their respective non-phosphorylated forms utilize a divalent metal cofactor: preferably magnesium. In further aspects of the invention the phosphatase contains but is not limited to containing a Rossmanoid fold domain for catalysis; additionally but not limited to containing a C1 or C2 capping domain for substrate specificity; additionally but not limited to containing a DxD signature in the 1st β-strand of the Rossmanoid fold for coordinating magnesium where the second Asp is a general acid/base catalyst; additionally but not limited to containing a Thr or Ser at the end of the 2nd β-strand of the Rossmanoid fold that helps stability of reaction intermediates; additionally but not limited to containing a Lys at the N-terminus of the α-helix C-terminal to the 3rd β-strand of the Rossmanoid fold that helps stability of reaction intermediates; and additionally but not limited to containing a GDxxxD, GDxxxxD, DD, or ED signature at the end of the 4th β-strand of the Rossmanoid fold for coordinating magnesium. These features are known in the art and are referenced in, for example, Burroughs et al., Evolutionary Genomics of the HAD Superfamily: Understanding the Structural Adaptations and Catalytic Diversity in a Superfamily of Phosphoesterases and Allied Enzymes. J. Mol. Biol. 2006; 361; 1003-1034.

In contrast to cell-based manufacturing methods, the invention involves a cell-free preparation of a hexose, has relatively high reaction rates due to the elimination of the cell membrane, which often slows down the transport of substrate/product into and out of the cell. It also has a final product free of nutrient-rich fermentation media/cellular metabolites.

Allose

One embodiment of the invention is a process for preparing allose which includes converting fructose 6-phosphate (F6P) to psicose 6-phosphate (P6P) catalyzed by psicose 6-phosphate 3-epimerase (P6PE), converting P6P to allose 6-phosphate (A6P) catalyzed by allose 6-phosphate isomerase (A6PI), and converting the A6P produced to allose catalyzed by allose 6-phosphate phosphatase.

Examples of P6PEs include, but are not limited to the following proteins, identified by UNIPROT ID numbers: D9TQJ4, A0A0901X28, and P32719. Of these, D9TQJ4 and A0A0901X28 are obtained from thermophilic organisms. P32719 is obtained from a mesophilic organism. P32719 is 53% identical to A0A0901X28 and 55% identical to D9TQJ4, and each protein catalyzes the epimerization of F6P to A6P. Furthermore, A0A0901X28 is 45% identical to D9TQJ4. Conversely, other epimerase proteins identified by UNIPROT ID numbers: A0A101D823, R1AXD6, A0A150LBU8, A0A023CQG9, and H1XWY2, which have a degree of identity to D9TQJ4 of 45% or less do not catalyze the epimerization of F6P to A6P. Examples of P6PEs also include any homologues having at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

Examples of A6PIs include, but are not limited to Uniprot ID W4V2C8, with the amino acid sequence set forth in SEQ ID NO: 1; and Uniprot ID Q67LX4, with the amino acid sequence set forth in SEQ ID NO: 2. Uniprot IDs W4V2C8 and Q67LX4 both catalyze the A6PI reaction and share 56% amino acid sequence identity. Therefore, examples of A6PIs also include any homologues having at least 55%, preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

A6PIs suitable for use in the process to convert P6P to A6P contain a Rossmanoid fold. A mesophilic A6PI described in the art (Mowbray et al., D-Ribose-5-Phosphate Isomerase B from *Escherichia coli* is Also a Functional D-Allose-6-phosphate Isomerase, While the *Mycobacterium tuberculosis* Enzyme is Not. J. Mol. Biol. 2008; 382; 667-679) shares conserved residues with the thermophilic A6PI disclosed in the invention. In some aspects of the invention the isomerase contains but is not limited to containing a His (mesophilic residue 10) C-terminal to the 1st β-strand of the Rossmanoid fold for phosphate binding; additionally but not limited to containing an Arg (mesophilic residue 133) C-terminal to the α-helix C-terminal to the 5th β-strand of the Rossmanoid fold also for phosphate binding; additionally but not limited to containing a His (mesophilic residue 99) in the active site to ring open the lactone; additionally but not limited to containing a Cys (mesophilic reside 66) in the active site to act as the catalytic base; additionally but not limited to containing a Thr (mesophilic residue 68) in the active site to act as the catalytic acid; additionally but not limited to containing a GTG-hydrophobic-G motif near the active site (mesophilic residues 67-71) to stabilize high energy intermediates, and additionally but not limited to containing a Asn (mesophilic residue 100) near the active site to also stabilize high energy intermediates. An A6PI preferably contains all of these conserved residues.

Examples of A6PPs include, but are not limited to the following proteins: Uniprot ID S9SDA3, with the amino acid sequence set forth in SEQ ID NO: 3; Q9X0Y1, with the amino acid sequence set forth in SEQ ID NO: 4; 13VT81, with the amino acid sequence set forth in SEQ ID NO: 5; A0A132NF06, with the amino acid sequence set forth in SEQ ID NO: 6; and D1C7G9, with the amino acid sequence set forth in SEQ ID NO: 7. Uniprot IDs S9SDA3 and 13VT81 both catalyze the A6PP reaction and share 30% amino acid sequence identity. Therefore, examples of A6PPs also include any homologues having at least 30%, preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

Preferably, an A6PP to convert A6P to allose, contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd β-strand of the Rossmanoid fold, and a ED signature at the end of the 4th β-strand of the Rossmanoid fold.

A process for preparing allose according to the invention also includes the step of enzymatically converting glucose 6-phosphate (G6P) to the F6P, and this step is catalyzed by phosphoglucoisomerase (PGI). In other embodiments, the process for preparing allose additionally includes the step of converting glucose 1-phosphate (G1P) to the G6P, where the step is catalyzed by phosphoglucomutase (PGM). In yet further embodiments, allose production process also includes the step of converting a saccharide to the G1P that is catalyzed at least one enzyme.

Therefore, a process for preparing allose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to P6P via P6PE, (v) converting P6P to A6P via A6PI, and (vi) converting A6P to allose via A6PP. An example of the enzymatic process where the saccharide is starch is shown in FIG. 1.

Typically, the ratios of enzyme units used in the disclosed process are 1:1:1:1:1:1 (αGP:PGM:PGI:P6PE:A6PI:A6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of allose production. For example, a particular enzyme may be present in an amount about 2×, 3×, 4×, 5×, etc. relative to the amount of other enzymes.

Phosphate ions produced by dephosphorylation of A6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the allose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Low phosphate concentration results in decreased production costs due to low total phosphate and thus lowered cost of phosphate removal. It also prevents inhibition of the A6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for for making allose involves an energetically favorable reaction.

Allose can also be produced from fructose. For example, the process involves generating F6P from fructose and polyphosphate catalyzed by polyphosphate fructokinase (PPFK); converting F6P to P6P catalyzed by P6PE; converting P6P to A6P catalyzed by A6PI, and converting A6P to allose catalyzed by A6PP. The fructose can be produced, for example, by an enzymatic conversion of sucrose.

Allose can also be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to P6P catalyzed by P6PE; converting P6P to A6P catalyzed by A6PI, and converting A6P to allose catalyzed by A6PP.

The phosphate ions generated when A6P is converted to allose can then be recycled in the step of converting sucrose to G1P. Additionally, PPFK and polyphosphate can be used to increase allose yields by producing F6P from fructose generated by the phosphorolytic cleavage of sucrose by SP.

In certain embodiments, a process for preparing allose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

Several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to allose and increased solubility.

Maltose phosphorylase (MP) can be used to increase allose yields by phosphorolytically cleaving the degradation product maltose into G1P and glucose. Alternatively, 4-glucan transferase (4GT) can be used to increase allose yields by recycling the degradation products glucose, maltose, and maltotriose into longer maltooligosaccharides; which can be phosphorolytically cleaved by αGP to yield G1P.

In certain embodiments, cellulose and its derived products can be converted to allose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to P6P catalyzed by P6PE; converting P6P to A6P catalyzed by A6PI, and converting A6P to allose catalyzed by A6PP. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

In some embodiments, polyphosphate and polyphosphate glucokinase (PPGK) can be added to the process, thus increasing yields of allose by phosphorylating the degradation product glucose to G6P.

Allose can be produced from glucose. The process involves the steps of generating G6P from glucose and polyphosphate catalyzed by polyphosphate glucokinase (PPGK); converting G6P to F6P catalyzed by PGI; converting F6P to P6P catalyzed by P6PE; converting P6P to A6P catalyzed by A6PI; and converting A6P to allose catalyzed by A6PP.

Processes of the invention for making allose use low-cost starting materials and reduce production costs by decreasing costs associated with the feedstock and product separation. Starch, cellulose, sucrose and some of their derivatives are less expensive feedstocks than, for example, fructose. When allose is produced from psiose, yields are lower than in the present invention, and allose must be separated from psicose via chromatography, which leads to higher production costs.

Also, the step of converting A6P to allose according to the invention is an irreversible phosphatase reaction, regardless of the feedstock. Therefore, allose is produced with a very high yield while effectively minimizing the subsequent product separation costs.

In contrast to cell-based manufacturing methods, the invention involves a cell-free preparation of allose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is allose produced by the processes described herein for producing allose.

Since allose as similar functionality to sucrose, allose prepared by processes of the invention may be added to any beverage or foodstuff to produce desired sweetness.

Allose prepared by the processes disclosed herein may also be used used to synergize the effect of potent sweeteners. When combined with one or more potent sweeteners, allose may be able to effect improvements in sensory characteristics such as mouthfeel, flavor and aftertaste of a sweetened product. The use of low calorie sweeteners, such as potent sweeteners, in a variety of food products is common place in food and beverage formulations. For many consumers, however, products marketed as diet or light versions of products that are artificially sweetened are not preferred. Attempts have been made over the years to improve the taste delivery of these diet or light products through the addition of small quantities of carbohydrates. Allose prepared the processes of the invention would not only able to effect improvements in the quality of food and beverage formulations, particularly in diet/light beverages, but that its use may be synergistic with potent sweeteners such that it is able to replace significant quantities of potent sweeteners, even when it is added at concentrations well below its measured sweet taste threshold.

Allose produced by processes disclosed herein may be combined with other sweeteners, such as extracts from the Stevia rebaudiana bertoni plant for the preparation of low calorie versions of foods such as ice cream.

Allose produced by processes disclosed herein may be used in presweetened ready to eat (RTE) breakfast cereals and other foods wherein D allose partially or totally replaces sucrose or other commonly used sugars, as a frosting.

Allose produced by processes disclosed herein may be used as part of a sweetener for foods and beverages in combination with sugar alcohols, such as erythritol, and nutritive sweeteners with significant caloric content, such as fructose, sucrose, dextrose, maltose, trehalose, rhamnose, corn syrups and fructo-oligosaccharides.

Allose produced by the processes disclosed herein may also be used as part of a composition that enhances the plant disease control.

Mannose

One embodiment of the invention is a process for preparing mannose which includes converting F6P to mannose 6-phosphate (M6P) catalyzed by mannose 6-phosphate isomerase (M6PI); and converting the M6P to mannose catalyzed by mannose 6-phosphate phosphatase (MEPP).

Examples of M6PIs include, but are not limited to the following proteins: Uniprot ID A0A1M6TLY7, with the amino acid sequence set forth in SEQ ID NO: 8; H1XQS6, with the amino acid sequence set forth in SEQ ID NO: 9; G2Q982, with the amino acid sequence set forth in SEQ ID NO: 10; and F8F1Z8, with the amino acid sequence set forth in SEQ ID NO: 11. Uniprot IDs G2Q982 and F8F1Z8 both perform the M6PI reaction and share 28% amino acid sequence identity. Therefore, examples of M6PIs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

M6PIs suitable for use in the process to convert F6P to M6P contain two domains with a core of antiparallel β-strands resembling the cupin fold and a third domain consisting of only α-helixes. A M6PI was structurally characterized in the art (Sagurthi et al. Structures of mannose-6-phosphate isomerase from *Salmonella typhimurium* bound to metal atoms and substrate: implications for catalytic mechanism. Acta Cryst. 2009; D65; 724-732) and shares conserved residues with the thermophilic M6PIs described in the invention. In some aspects of the invention the isomerase contains but is not limited to containing a divalent metal cation, preferably $Mg^{2+}$ or $Zn^{2+}$; additionally but not limited to containing a Glu and two His residues proposed for use in metal binding (PDB 3H1M residues 134, 99, and 255 respectively); additionally but not limited to containing an Asp and Lys residue proposed for acid/base catalysis (PDB 3H1M residues 270 and 132 respectively); and additionally but not limited to containing a Lys, Pro, and Ala residue proposed for phosphate binding (PDB 3H1M residues 132, 133, and 267 respectively). An M6PI preferably contains all of these conserved residues.

Examples of M6PPs include, but are not limited to the following proteins: Uniprot ID A0A1A6DS13, with the amino acid sequence set forth in SEQ ID NO: 12; A0A1M4UN08, with the amino acid sequence set forth in SEQ ID NO: 13; and A0A1N6FCW3, with the amino acid sequence set forth in SEQ ID NO: 14 Uniprot IDs A0A1A6DS13 and A0A1N6FCW3 both catalyze the M6PP reaction and share 35% amino acid sequence identity. Therefore, examples of M6PPs also include any homologues having at least 35%, more preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

Preferably, an M6PP to convert M6P to mannose contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd β-strand of the Rossmanoid fold, and a GDxxxD signature at the end of the 4th β-strand of the Rossmanoid fold.

A process for preparing mannose according to the invention also includes the step of enzymatically converting glucose 6-phosphate (G6P) to the F6P, and this step is catalyzed by phosphoglucoisomerase (PGI). In other embodiments, the process for preparing mannose additionally includes the step of converting glucose 1-phosphate (G1P) to the G6P, where the step is catalyzed by phosphoglucomutase (PGM). In further embodiments, the process for preparing mannose includes the conversion of G6P to F6P to M6P, where this step is catalyzed by bifunctional phosphoglucose/phosphomannose isomerase (PGPMI). In yet further embodiments, mannose production process also includes the step of converting a saccharide to the G1P that is catalyzed at least one enzyme.

Processes of the invention for the production of mannose use PGPMIs that convert G6P or F6P to M6P. Examples of PGPMIs include, but are not limited to the following proteins: Uniprot ID D7CPH7, with the amino acid sequence set forth in SEQ ID NO: 15; A0A085L170, with the amino acid sequence set forth in SEQ ID NO: 16; and M1E6Z3, with the amino acid sequence set forth in SEQ ID NO: 17. Uniprot IDs A0A085L170 and M1E6Z3 both catalyze the PGPMI reaction and share 28% amino acid sequence identity. Therefore, examples of PGPMIs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

PGPMI suitable for use in the process to convert G6P or F6P to M6P contain two Rossmanoid folds. A PGPMI was structurally characterized in the art (Swan et al. A Novel Phosphoglucose Isomerase (PGI)/Phosphomannose Isomerase from the Crenarchaeon *Pyrobaculum aerophilum* Is a Member of the PGI Superfamily. J. Biol. Chem. 2004: 279; 39838-39845) and shares conserved residues with the thermophilic PGPMIs described in the invention. In some aspects of the invention the isomerase contains but is not limited to containing a GGS motif (PDB 1TZB residues 46-48) where the Gly residues assist in substrate binding and the Ser residue binds phosphate; additionally but not limited to containing a SYSG-X-T-X-ET-Hydrophobic motif (PDB 1TZB residues 87-96) that binds phosphate; additionally but not limited to containing an Arg residue (PDB 1TZB residue 135) that stabilizes high energy intermediates during catalysis; additionally but not limited to containing an EN signature (PDB 1TZB residues 203-204) where the Glu is essential for active-site base proton transfer; additionally but not limited to containing an HN signature (PDB 1TZB residues 219-220) where the His is important for ring opening/closure of the substrate during catalysis; and additionally but not limited to containing a conserved Lys residue (PDB 1TZB residue 298) that is important for ring opening/closure of the substrate during catalysis. The conserved residues' functions are verified in a separate publication (Hansen et al. Bifunctional Phosphoglucose/Phosphomannose Isomerases from the Archaea *Aeropyrum pernix* and *Thermoplasma acidophilum* Constitute a Novel Enzyme Family within the Phosphoglucose Isomerase Superfamily. J Biol. Chem. 2004; 279; 2262-2272). An PGPMI preferably contains all of these conserved residues.

Figure 2:
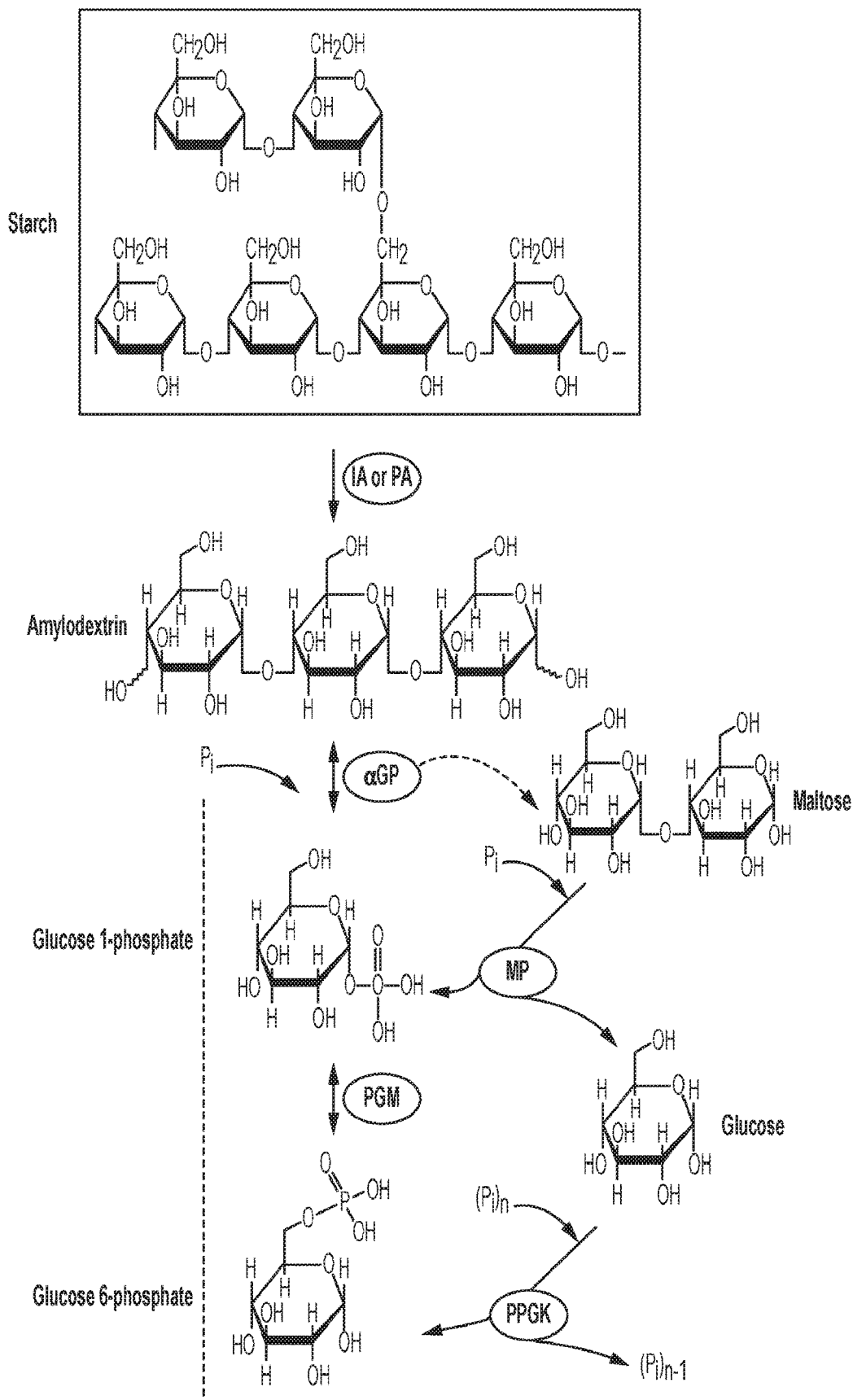
FIG. 2 is a schematic diagram showing an enzymatic pathway converting starch or its derived products to mannose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; PGPMI, bifunctional phosphoglucose/phosphomannose isomerase; M6PI, mannose 6-phosphate isomerase; M6PP, mannose 6-phosphate phosphatase.
Figure 2:
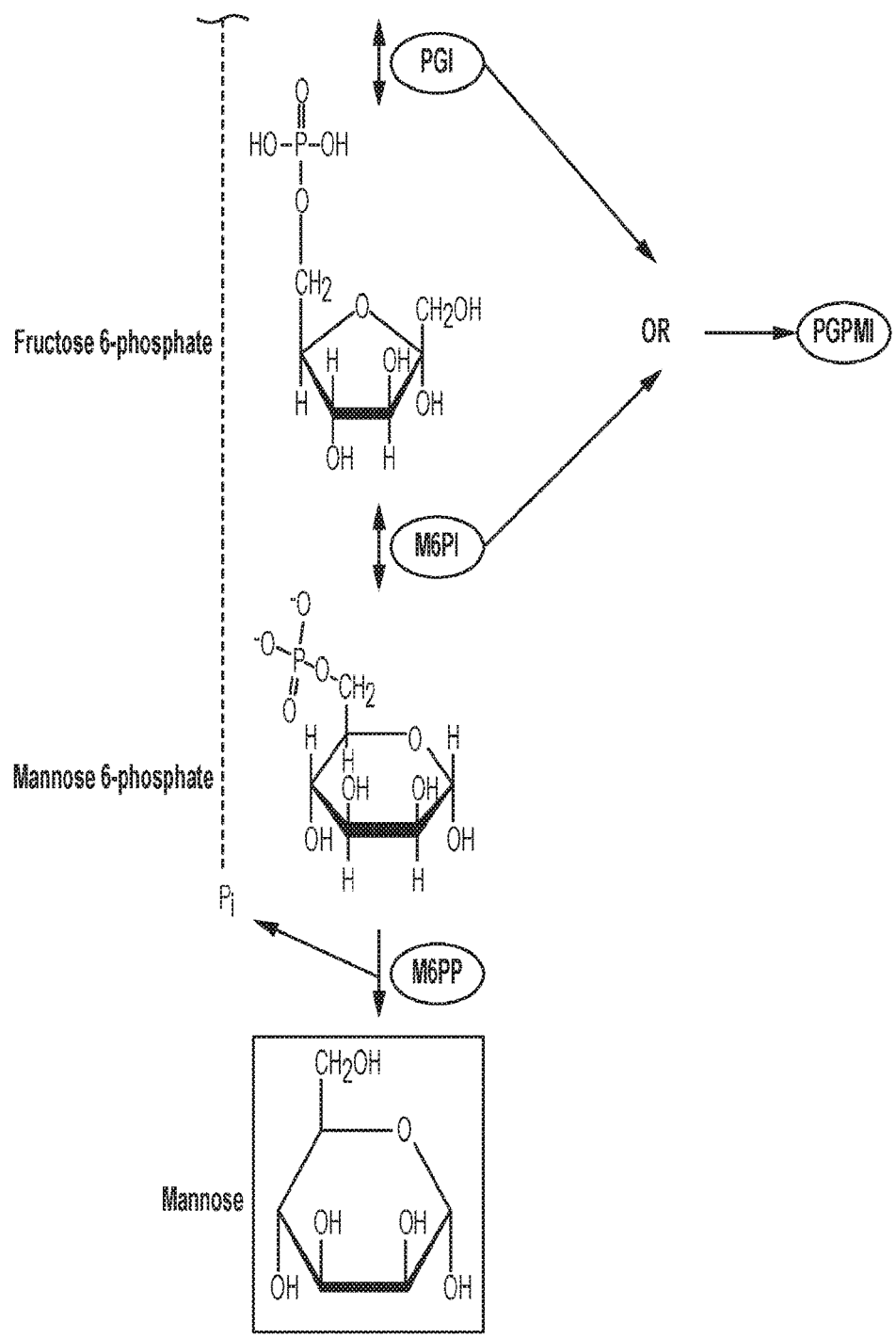

Therefore, a process for preparing mannose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to M6P via mannose 6-phosphate isomerase (M6PI, EC 5.3.1.8), (v) converting G6P to M6P via bifunctional phosphoglucose/phosphomannose isomerase (PGPMI, EC 5.3.1.8 and 5.3.1.9), and (vi) converting M6P to mannose via M6PP. An example of the process where the saccharide is starch is shown in FIG. 2.

Typically, the ratios of enzyme units used in the disclosed process are 1:1:1:1:1 (αGP:PGM:PGI:M6PI:M6PP) or 1:1:1:1 (αGP:PGM:PGPMI:M6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:3 can be used to further increase the reaction rate. Therefore, the enzyme ratios, including other optional enzymes discussed below, can be varied to increase the efficiency of mannose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of M6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the mannose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the M6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making mannose involves an energetically favorable reaction.

Mannose can also be produced from fructose. For example, the process involves generating F6P from fructose and polyphosphate catalyzed by polyphosphate fructokinase (PPFK); converting F6P to M6P catalyzed by M6PI; and converting M6P to mannose catalyzed by M6PP. The fructose can be produced, for example, by an enzymatic conversion of sucrose.

Mannose can also be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to M6P catalyzed by M6PI; and converting M6P to mannose catalyzed by M6PP. In the above steps, the conversion of G6P to F6P to M6P can alternatively be catalyzed by PGPMI.

The phosphate ions generated when M6P is converted to mannose can then be recycled in the step of converting sucrose to G1P. Additionally, PPFK and polyphosphate can be used to increase mannose yields by producing F6P from fructose generated by the phosphorolytic cleavage of sucrose by SP.

In some embodiments, a process for preparing mannose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to mannose. In certain embodiments, artificial (non-natural) ATP-free enzymatic pathways are provided to convert starch, cellulose, sucrose, and their derived products to mannose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to mannose and increased solubility.

Maltose phosphorylase (MP) can be used to increase mannose yields by phosphorolytically cleaving the degradation product maltose into G1P and glucose. Alternatively, 4-glucan transferase (4GT) can be used to increase mannose yields by recycling the degradation products glucose, maltose, and maltotriose into longer maltooligosaccharides; which can be phosphorolytically cleaved by αGP to yield G1P.

In certain embodiments, cellulose and its derived products can be converted to mannose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to M6P catalyzed by M6PI; and converting M6P to mannose catalyzed by M6PP. Alternatively, in the previous pathway the conversion of G6P to F6P to M6P can be catalyzed by PGPMI. In this process, the phosphate ions can be recycled by the step of converting cellodextrin and cellobiose to G1P.

In some embodiments, polyphosphate and polyphosphate glucokinase (PPGK) can be added to the process, thus increasing yields of mannose by phosphorylating the degradation product glucose to G6P.

In other embodiments, mannose can be generated from glucose. The process involves the steps of generating G6P from glucose and polyphosphate catalyzed by polyphosphate glucokinase (PPGK); converting G6P to F6P catalyzed by PGI; converting F6P to M6P catalyzed by M6PI; and converting M6P to mannose catalyzed by M6PP. Alternatively, the conversion of G6P to F6P to M6P can be catalyzed by PGPMI.

Processes of the invention use low-cost starting materials and reduce production costs by decreasing costs associated with the feedstock and product separation. Starch, cellulose, sucrose and some of their derivatives are less expensive feedstocks than, for example, fructose. When mannose is produced from fructose, yields are lower than in the present invention, and mannose must be separated from fructose via chromatography, which leads to higher production costs.

Also, the step of converting M6P to mannose according to the invention is an irreversible phosphatase reaction, regardless of the feedstock. Therefore, mannose is produced with a very high yield while effectively minimizing the subsequent product separation costs.

In contrast to cell-based manufacturing methods, the invention involves a cell-free preparation of mannose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is mannose produced by the processes described herein for producing mannose.

Mannose produced by processes described herein may be used, as discussed above, in a variety of applications in the pharmaceutical, cosmetic, beverage, food product, dairy, confectionery, and livestock industries.

Additionally, mannose produced by the processes disclosed herein may be converted to mannitol through hydrogenation. The catalytic hydrogenation of mannose occurs with a stoichiometric yield and gives mannitol. U.S. Pat. No. 5,466,795. Mannitol is widely used in the manufacture of sugar-free chewing gum, sweets and pharmaceutical excipients. However, the production of high-purity mannose is extremely difficult to achieve and is costly. Id. Accordingly, mannose produced by the aforementioned processes can be converted to mannitol via catalytic hydrogenation.

Galactose

One embodiment of the invention is a process for preparing galactose which includes converting fructose 6-phosphate (F6P) to tagatose 6-phosphate (T6P) catalyzed by fructose 6-phosphate 4-epimerase (F6PE), converting T6P to galactose 6-phosphate (Gal6P) catalyzed by galactose 6-phosphate isomerase (Gal6PI), and converting the Gal6P produced to galactose catalyzed by galactose 6-phosphate phosphatase (Gal6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

Gal6PI exists as a multimer of two subunits, LacA and LacB. Examples of Gal6PIs include, but are not limited to the following protein (LacA/LacB) subunit pair: Uniprot ID P23494/P23495, with the amino acid sequences set forth in SEQ ID NO: 18/SEQ ID NO: 19. Examples of Gal6PIs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID for LacA subunit and homologues having at least 25%, at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID for LacB subunit.

Gal6PIs suitable for use in the process to convert T6P to Gal6P contain a heterodimer ('A' and 'B') consisting of subunits with Rossmann-like αβα sandwich folds. Conserved residues are discussed in the art (Jung et al. Crystal Structure and Substrate Specificity of D-Galactose-6-Phosphate Isomerase Complexed with Substrates. PLOS ONE. 2013; 8; e72902). In some aspects of the invention the isomerase heterodimer contains but is not limited to containing Arg130 and Arg134 in 'A' and His9 and Arg39 in 'B' to bind the substrate's phosphate group; additionally but not limited to containing His96 in 'A' for ring opening of substrate; additionally but not limited to containing Asn97 in 'A' to stabilize high energy intermediates; and additionally but limited to containing Cys65 and Thr67 of 'B' to participate in proton transfer.

Examples of Gal6PPs include, but are not limited to Uniprot ID Q8A2F3 with the amino acid sequence set forth in SEQ ID NO: 20. Examples of Gal6PPs also include any homologues having at least 25%, at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID.

Preferably, a Gal6PP to convert Gal6P to galactose contains a Rossmanoid fold domain for catalysis, a C2 capping domain, DxD signature in the 1st β-strand of the Rossmanoid fold, a Thr or Ser at the end of the 2nd β-strand of the Rossmanoid fold, and a GDxxxD signature at the end of the 4th β-strand of the Rossmanoid fold.

A process for preparing galactose according to the invention also includes the step of enzymatically converting glucose 6-phosphate (G6P) to the F6P, and this step is catalyzed by phosphoglucoisomerase (PGI). In other embodiments, the process for preparing galactose additionally includes the step of converting glucose 1-phosphate (G1P) to the G6P, where the step is catalyzed by phosphoglucomutase (PGM). In yet further embodiments, galactose production process also includes the step of converting a saccharide to the G1P that is catalyzed at least one enzyme.

Figure 3:
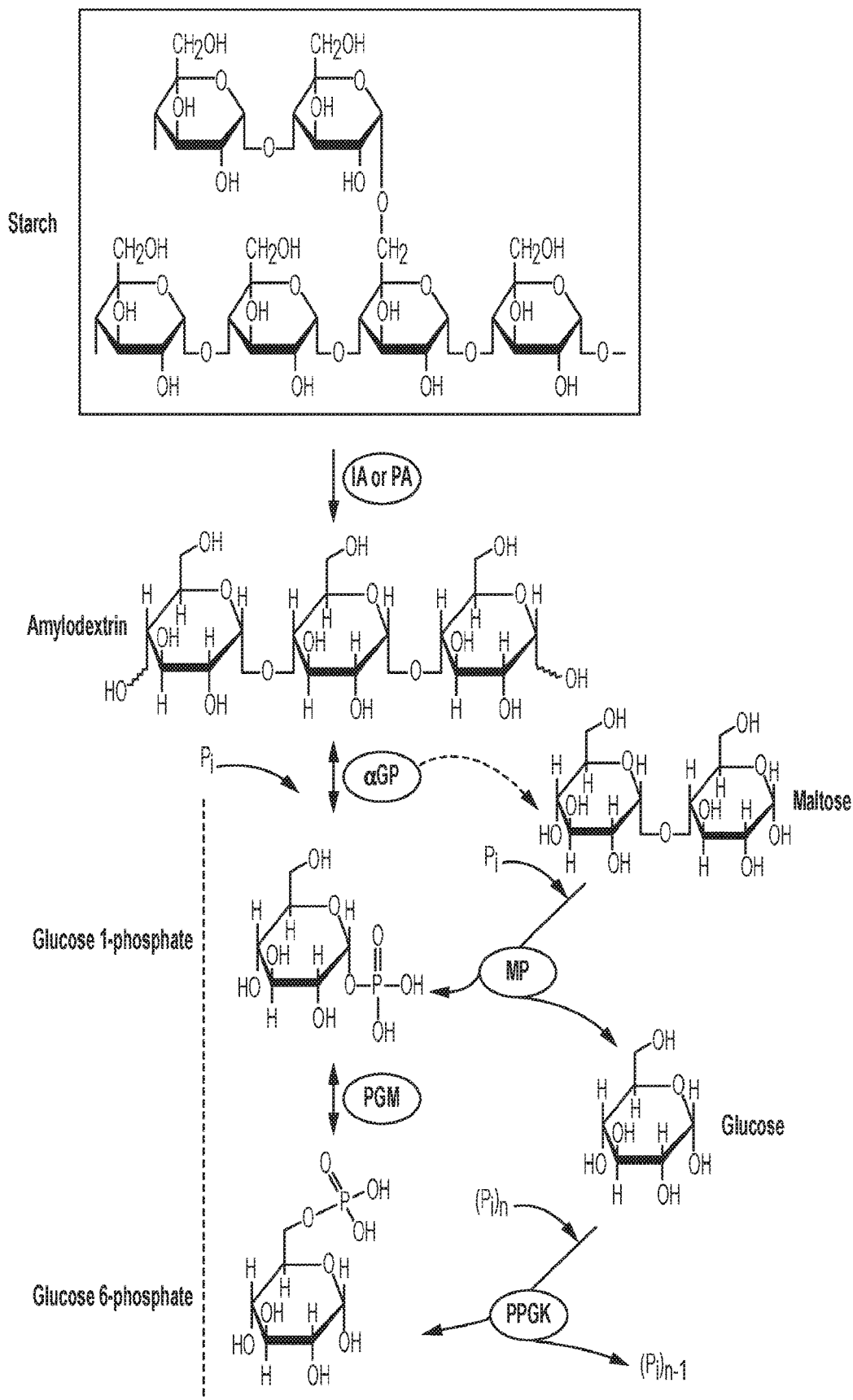
FIG. 3 is a schematic diagram showing an enzymatic pathway converting starch or its derived products to galactose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate isomerase; Gal6PI, galactose 6-phosphate isomerase; Gal6PP, galactose 6-phosphate phosphatase.
Figure 3:
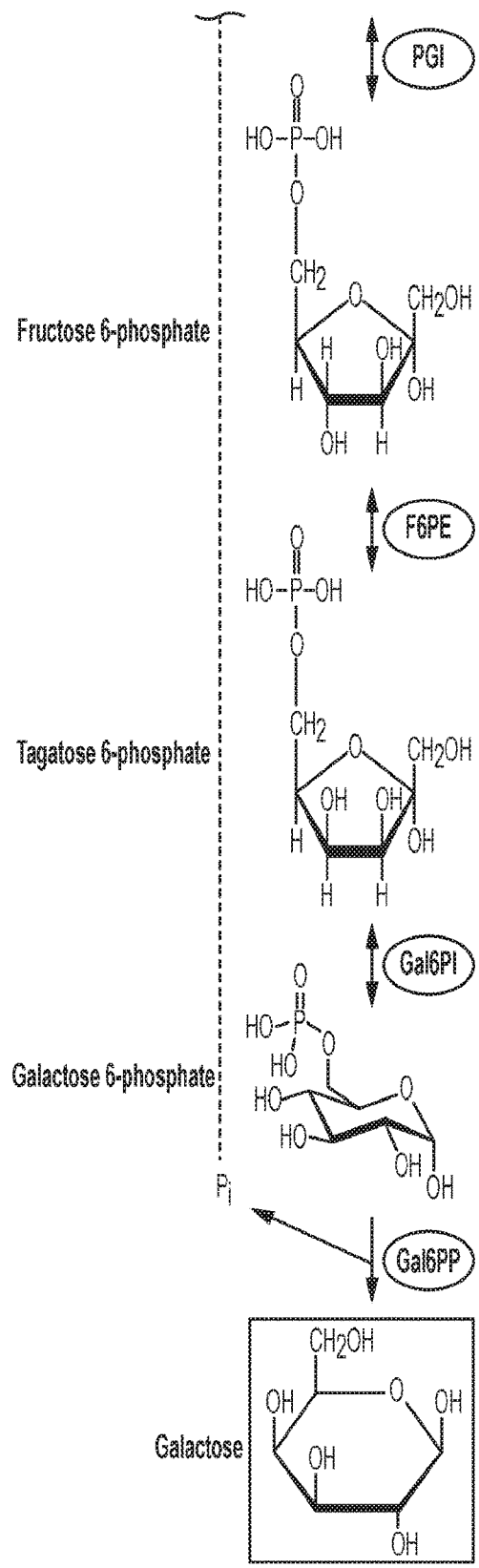
Figure 4:
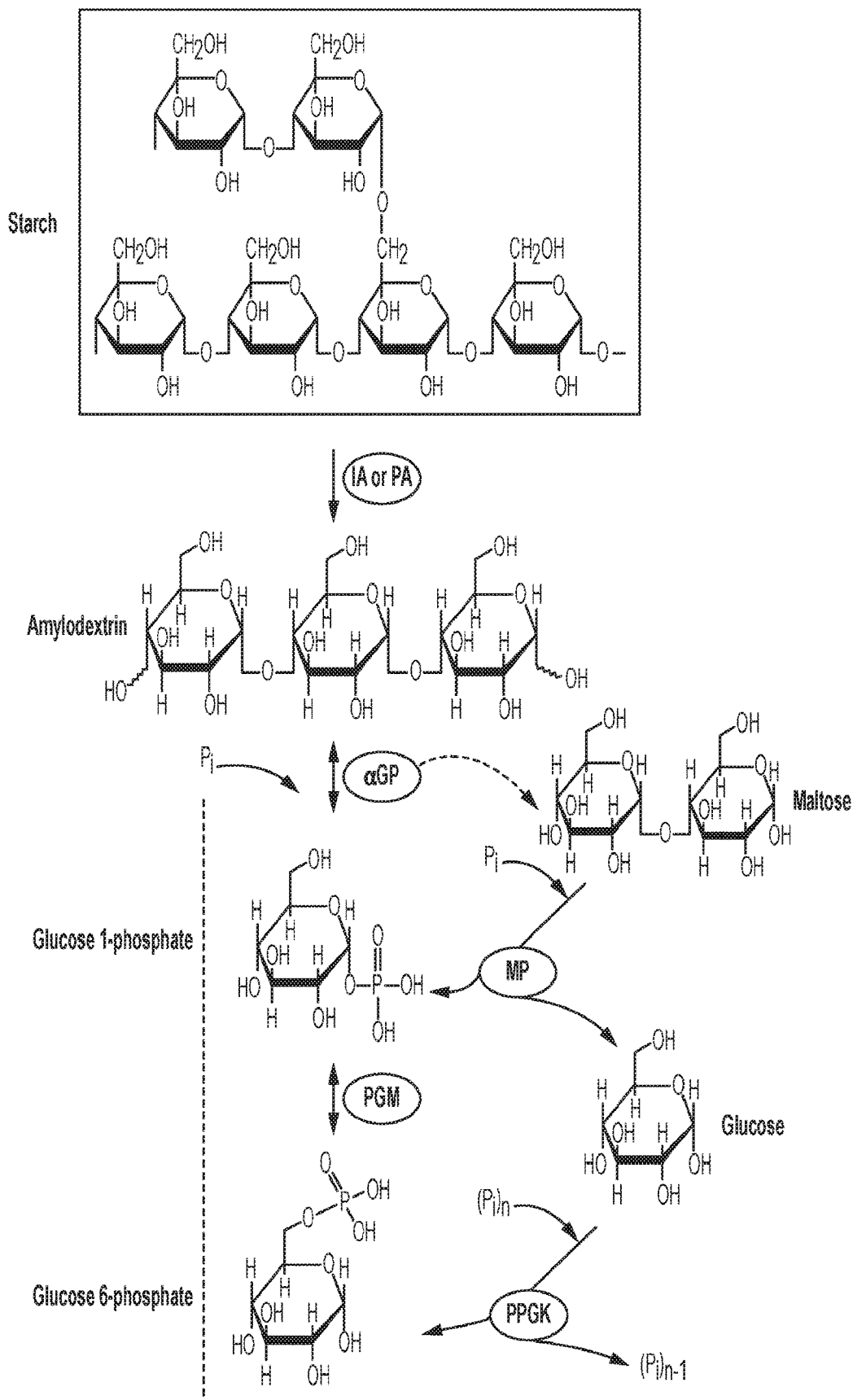
FIG. 4 is a schematic diagram showing an enzymatic pathway converting starch or its derived products to galactose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PP, fructose 6-phosphate phosphatase.
Figure 4:
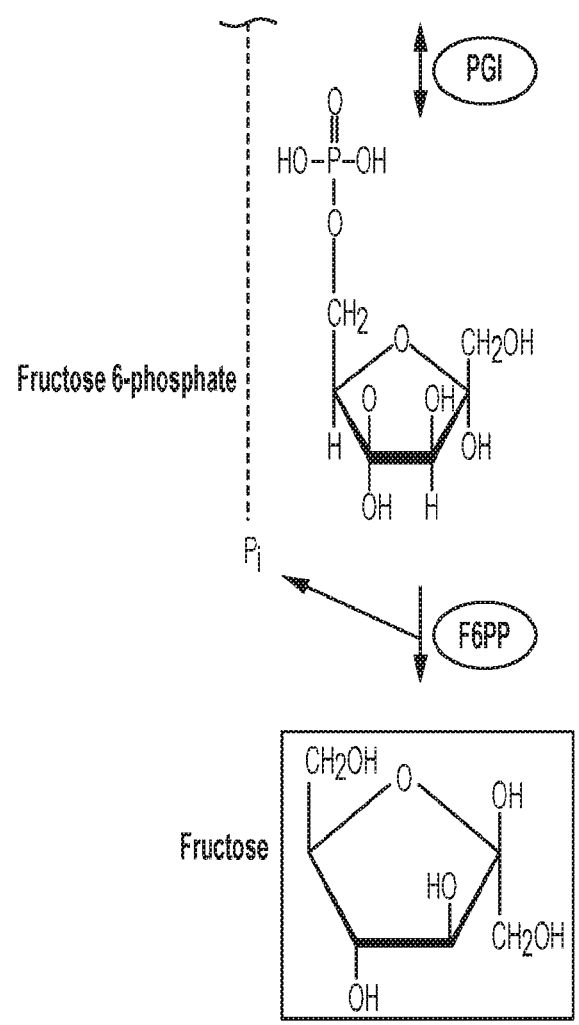

Therefore, a process for preparing galactose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to Gal6P via Gal6PI (EC 5.3.1.26), and (vi) converting Gal6P to galactose via Gal6PP. An example of the process where the saccharide is starch is shown in FIG. 3.

Typically, the ratios of enzyme units used in the disclosed process are 1:1:1:1:1:1 (αGP:PGM:PGI:F6PE:Gal6PI:Gal6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of galactose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of Gal6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the galactose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the Gal6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making galactose involves an energetically favorable reaction.

Galactose can also be produced from fructose. For example, the process involves generating F6P from fructose and polyphosphate catalyzed by polyphosphate fructokinase (PPFK); converting F6P to T6P catalyzed by F6PE; converting T6P to Gal6P catalyzed by Gal6PI, and converting Gal6P to galactose catalyzed by Gal6PP. The fructose can be produced, for example, by an enzymatic conversion of sucrose.

Galactose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to Gal6P catalyzed by Gal6PI, and converting Gal6P to galactose catalyzed by Gal6PP.

The phosphate ions generated when Gal6P is converted to galactose can then be recycled in the step of converting sucrose to G1P. Additionally, PPFK and polyphosphate can be used to increase galactose yields by producing F6P from fructose generated by the phosphorolytic cleavage of sucrose by SP.

In some embodiments, a process for preparing galactose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to galactose. In certain embodiments, artificial (non-natural) ATP-free enzymatic pathways are provided to convert starch, cellulose, sucrose, and their derived products to galactose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to galactose and increased solubility.

Maltose phosphorylase (MP) can be used to increase galactose yields by phosphorolytically cleaving the degradation product maltose into G1P and glucose. Alternatively, 4-glucan transferase (4GT) can be used to increase galactose yields by recycling the degradation products glucose, maltose, and maltotriose into longer maltooligosaccharides; which can be phosphorolytically cleaved by αGP to yield G1P.

In certain embodiments, cellulose and its derived products can be converted to galactose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to Gal6P catalyzed by Gal6PI, and converting Gal6P to galactose catalyzed by Gal6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of galactose by phosphorylating the degradation product glucose to G6P.

In other embodiments, galactose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to Gal6P catalyzed by Gal6PI; and converting Gal6P to galactose catalyzed by Gal6PP.

Processes of the invention use low-cost starting materials and reduce production costs by decreasing costs associated with the feedstock and product separation. Starch, cellulose, sucrose and some of their derivatives are less expensive feedstocks than, for example, lactose. When galactose is produced from biomass or lactose, yields are lower than in the present invention, and galactose must be separated from other sugars via chromatography, which leads to higher production costs. Furthermore, our process is animal-free.

The step of converting Gal6P to galactose according to the invention is an irreversible phosphatase reaction, regardless of the feedstock. Therefore, galactose is produced with a very high yield while effectively minimizing the subsequent product separation costs.

In contrast to cell-based manufacturing methods, the invention involves a cell-free preparation of galactose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is galactose produced by the processes described herein for producing galactose.

Fructose

One embodiment of the invention is a process for preparing fructose which includes converting fructose 6-phosphate (F6P) to fructose catalyzed by fructose 6-phosphate phosphatase (F6PP).

A non-limiting example of an F6PP is Uniprot ID B8CWV3, with the amino acid sequence set forth in SEQ ID NO: 21. Examples of F6PPs also include any homologues having at least 25%, at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID.

Preferably, a F6PP to convert F6P to fructose contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd β-strand of the Rossmanoid fold, and a ED signature at the end of the 4th β-strand of the Rossmanoid fold.

A process for preparing fructose according to the invention also includes the step of enzymatically converting glucose 6-phosphate (G6P) to the F6P, and this step is catalyzed by phosphoglucoisomerase (PGI). In other embodiments, the process for preparing fructose additionally includes the step of converting glucose 1-phosphate (G1P) to the G6P, where the step is catalyzed by phosphoglucomutase (PGM). In yet further embodiments, fructose production process also includes the step of converting a saccharide to the G1P that is catalyzed at least one enzyme.

Therefore, a process for preparing fructose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to fructose using F6PP.

Typically, the ratios of enzyme units used in the disclosed process are 1:1:1:1 (αGP:PGM:PGI:F6PP). To optimize product yields, these ratios can be adjusted in any number of combinations. For example, a ratio of 3:1:1:1 can be used to maximize the concentration of phosphorylated intermediates, which will result in increased activity of the downstream reactions. Conversely, a ratio of 1:1:1:3 can be used to maintain a robust supply of phosphate for αGP, which will result in more efficient phosphorolytic cleavage of alpha-1, 4-glycosidic bonds. A ratio of enzymes, for example, 3:1:1:3 can be used to further increase the reaction rate. Therefore, the enzyme ratios, including other optional enzymes discussed below, can be varied to increase the efficiency of fructose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of F6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the fructose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the F6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making fructose involves an energetically favorable reaction.

Figure 5:
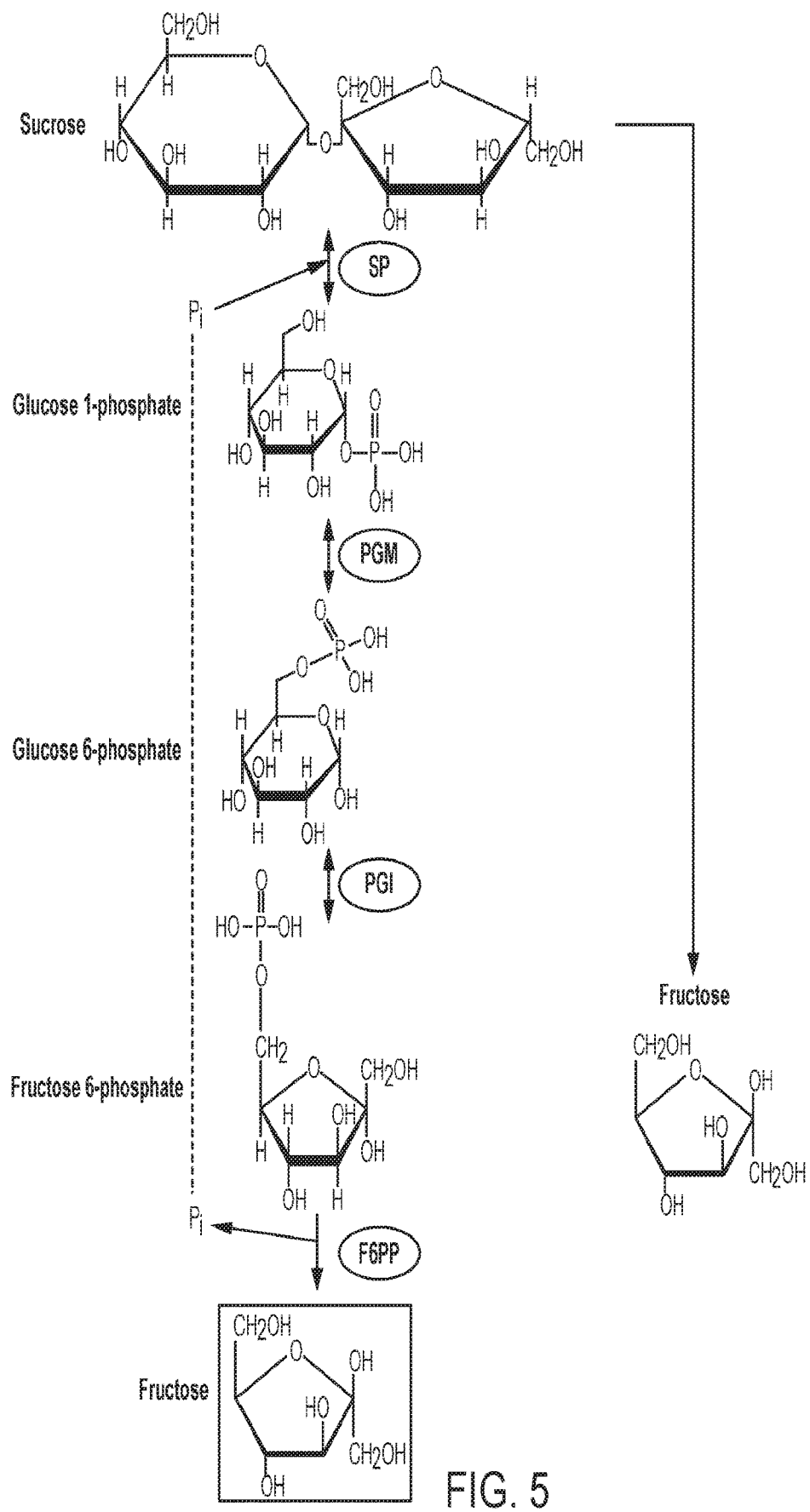
FIG. 5 is a schematic diagram showing an enzymatic pathway converting sucrose to fructose. The following abbreviations are used: SP, sucrose phosphorylase; PGM, phosphoglucomutase; PGI, phosphoglucoisomerase; F6PP, fructose 6-phosphate phosphatase.
Figure 6:
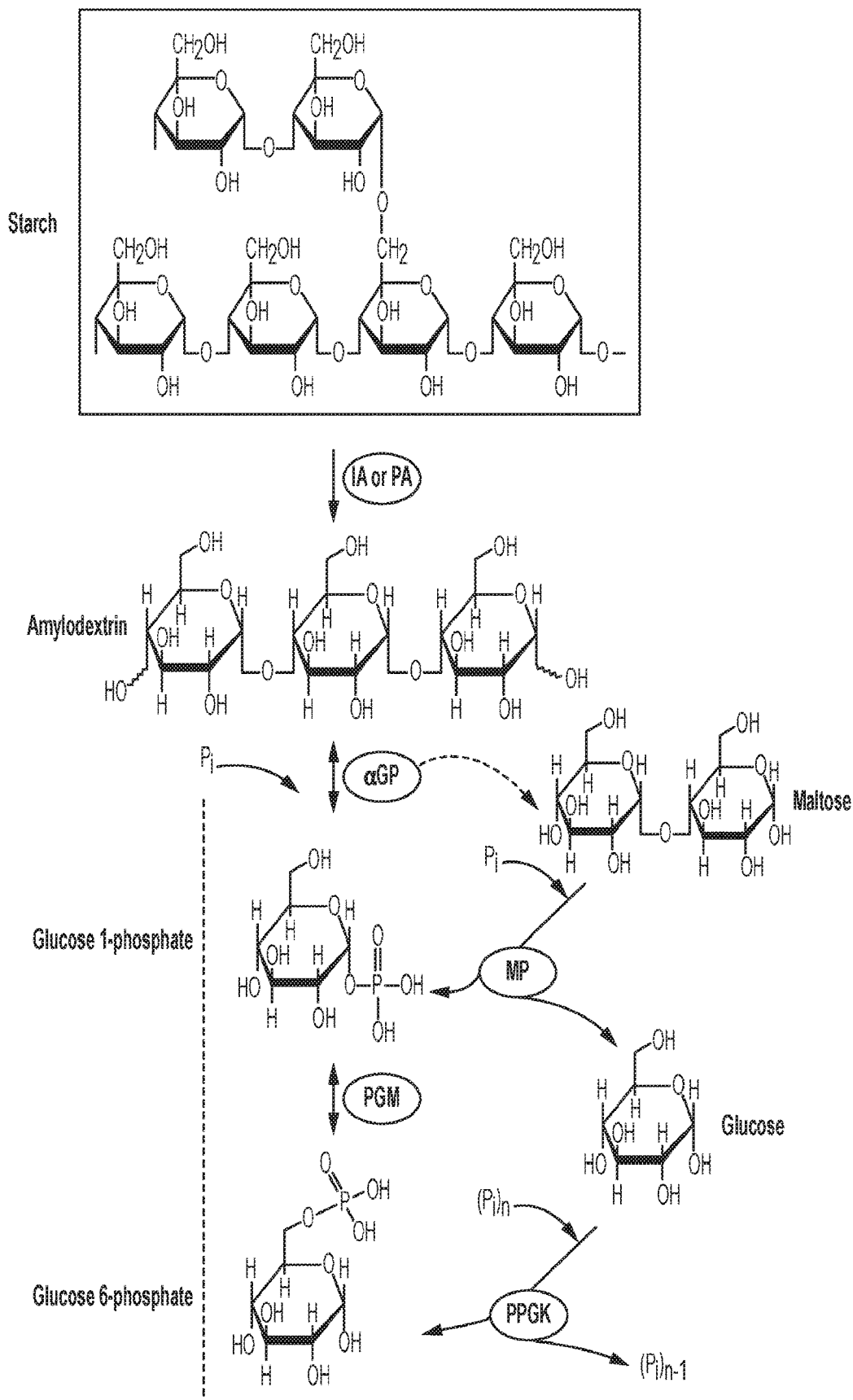
FIG. 6 is a schematic diagram showing an enzymatic pathway converting starch or its derived products to altrose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; P6PE, psicose 6-phosphate epimerase; Alt6PI, altrose 6-phosphate isomerase; Alt6PP, altrose 6-phosphate phosphatase.
Figure 6:
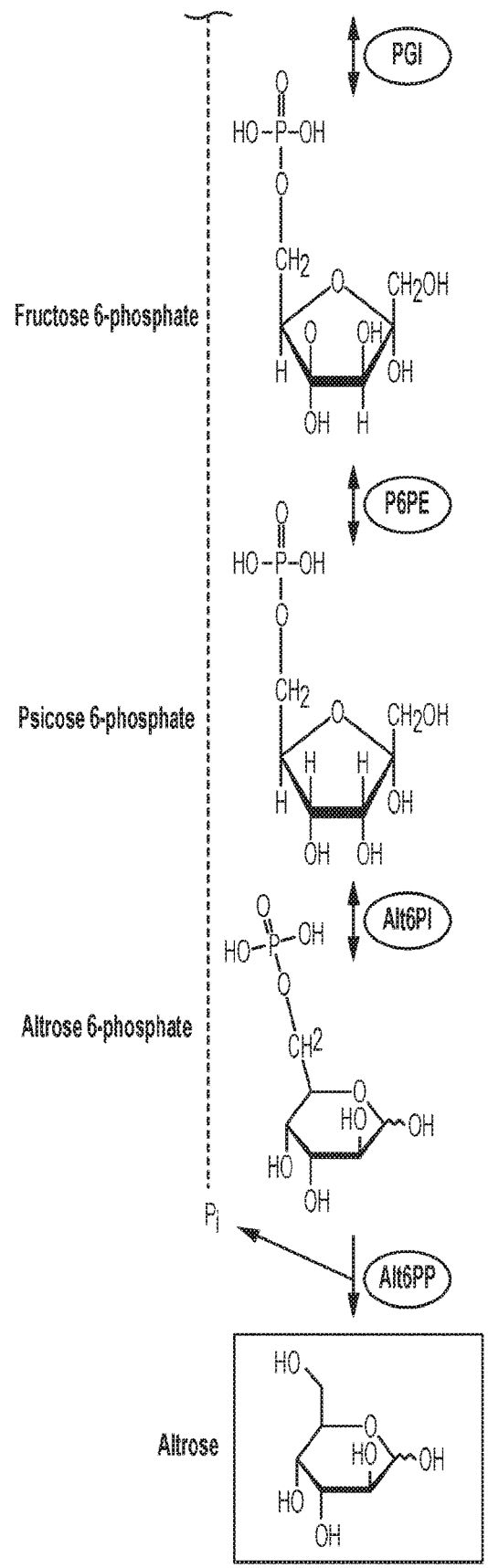
Figure 7:
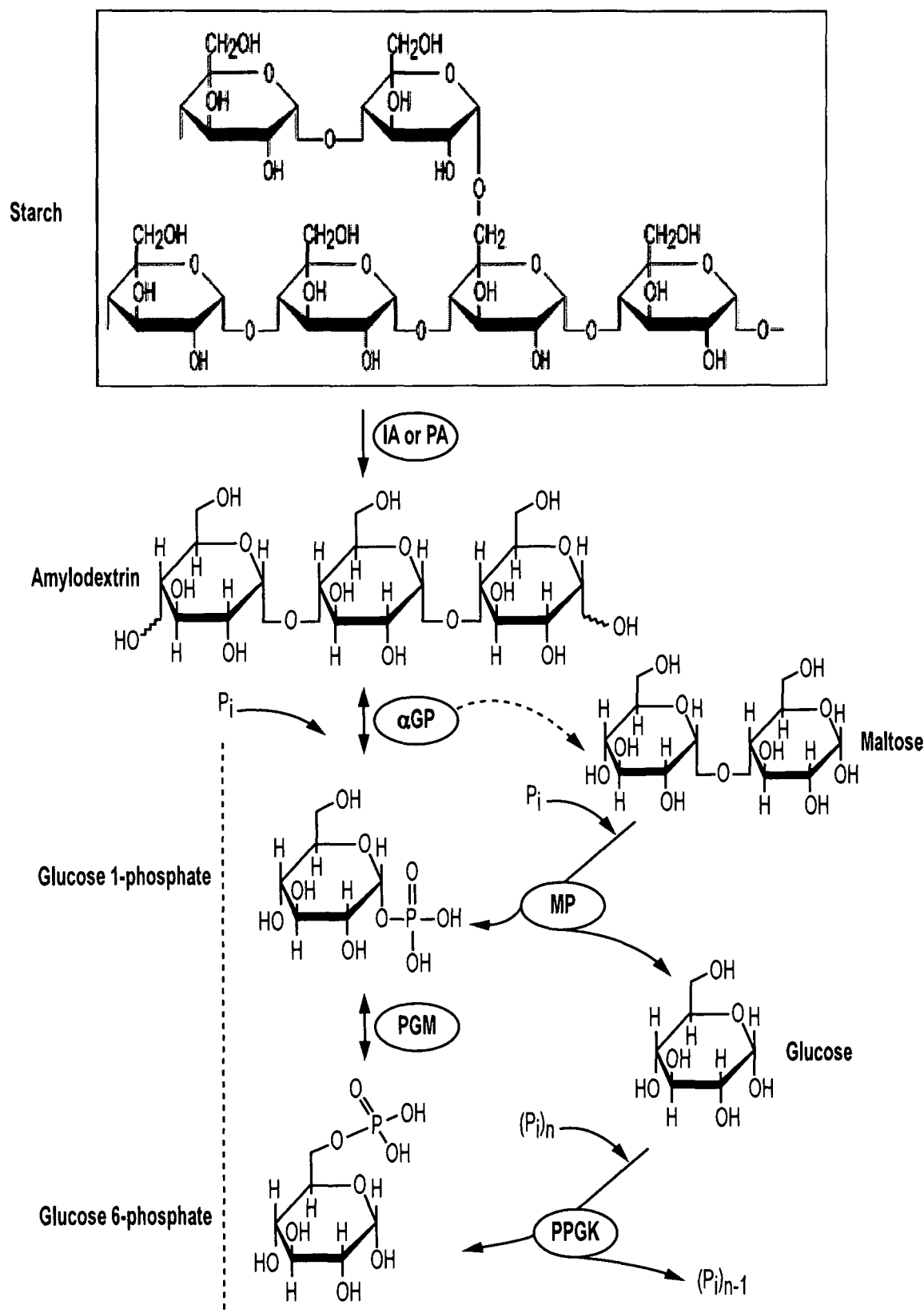
FIG. 7 is a schematic diagram showing an enzymatic pathway converting starch or its derived products to talose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; Tal6PI, talose 6-phosphate isomerase; Tal6PP, talose 6-phosphate phosphatase.
Figure 7:
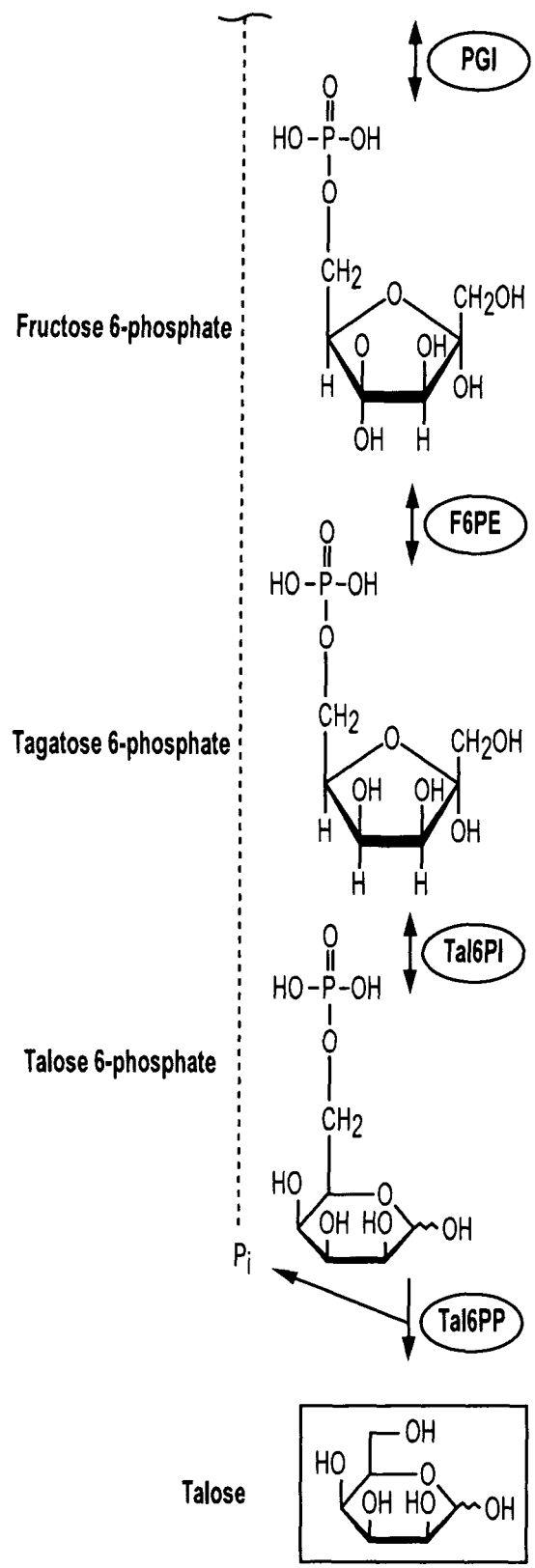
Figure 8:
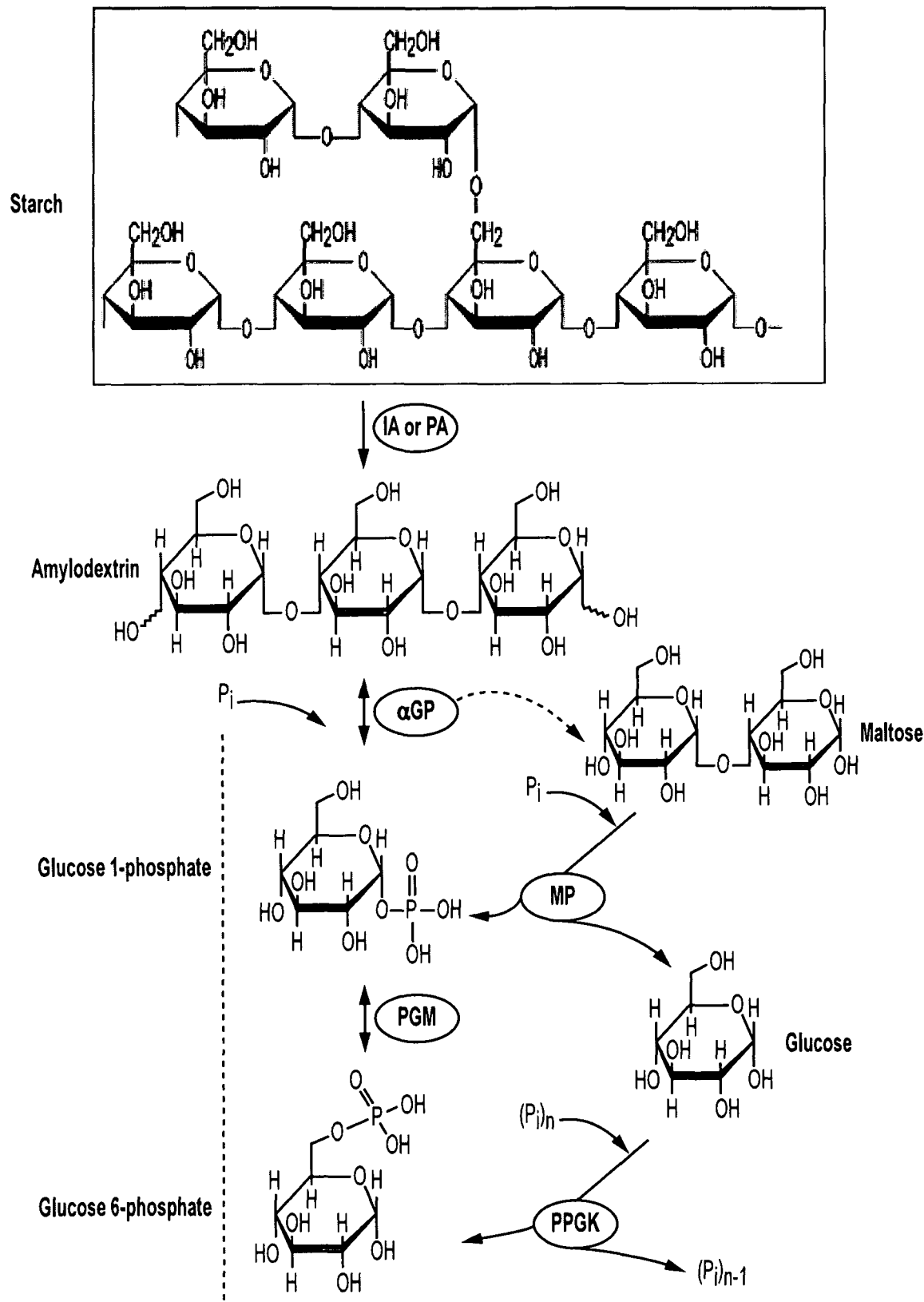
FIG. 8 is a schematic diagram showing an enzymatic pathway converting starch or its derived products to sorbose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; S6PE, sorbose 6-phosphate epimerase; S6PP, sorbose 6-phosphate phosphatase.
Figure 8:
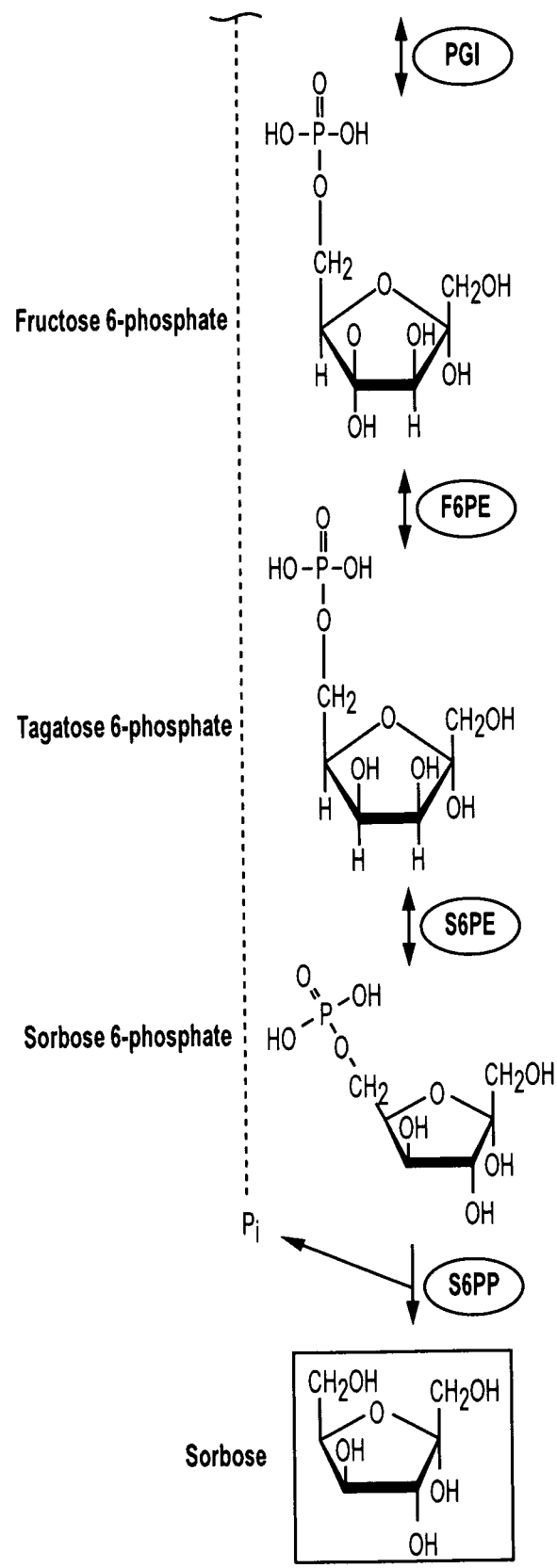
Figure 9:
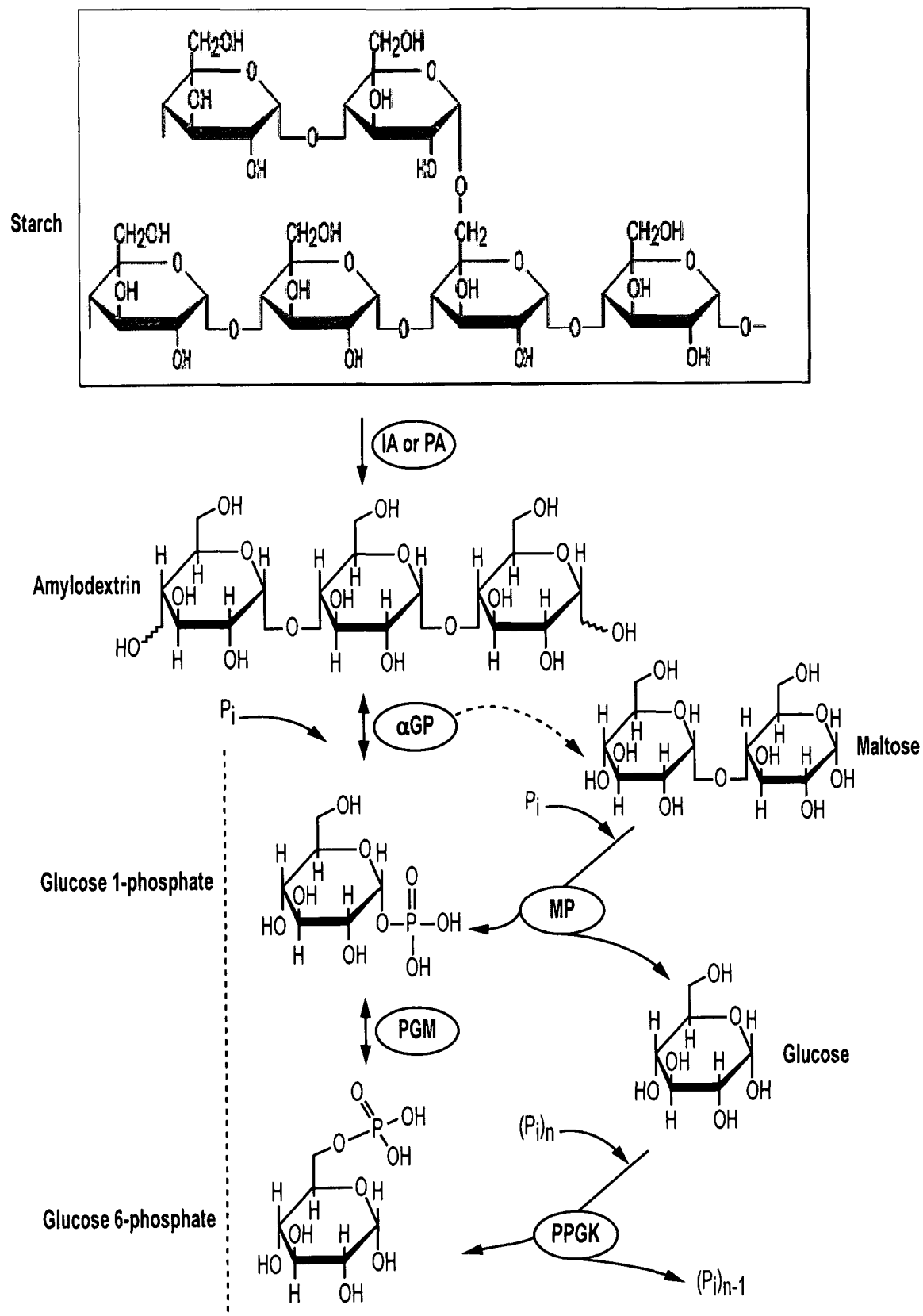
FIG. 9 is a schematic diagram showing an enzymatic pathway converting starch or its derived products to gulose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; S6PE, sorbose 6-phosphate epimerase; Gul6PI, gulose 6-phosphate isomerase; Gul6PP, gulose 6-phosphate phosphatase.
Figure 9:
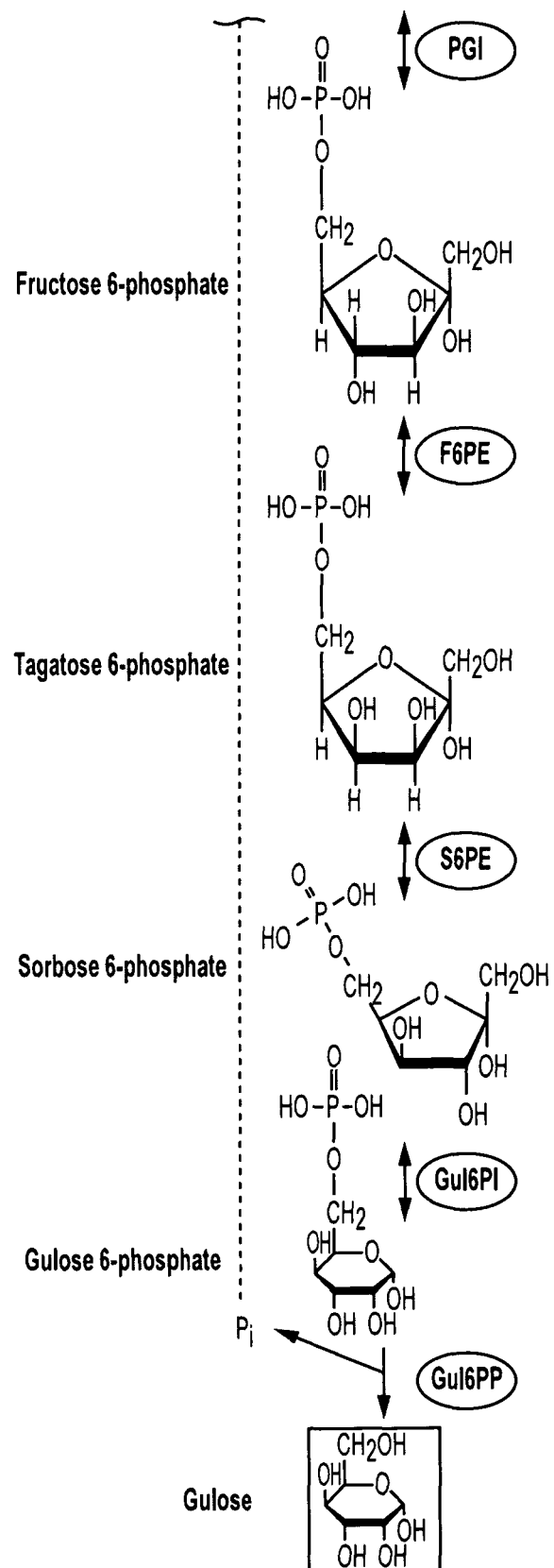
Figure 10:
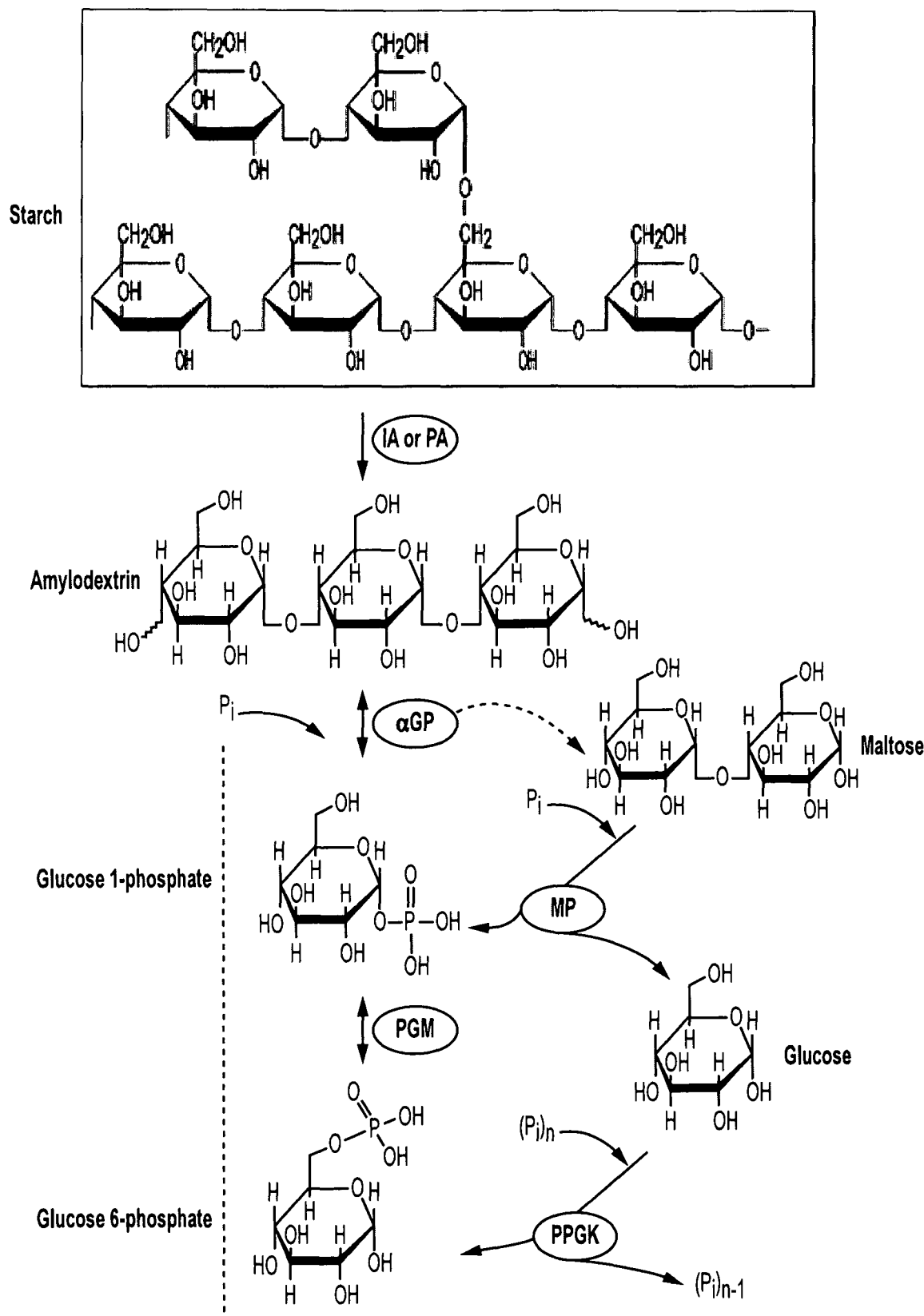
FIG. 10 is a schematic diagram showing an enzymatic pathway converting starch or its derived products to idose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; S6PE, sorbose 6-phosphate epimerase; I6PI, idose 6-phosphate isomerase; I6PP, idose 6-phosphate phosphatase.
Figure 10:
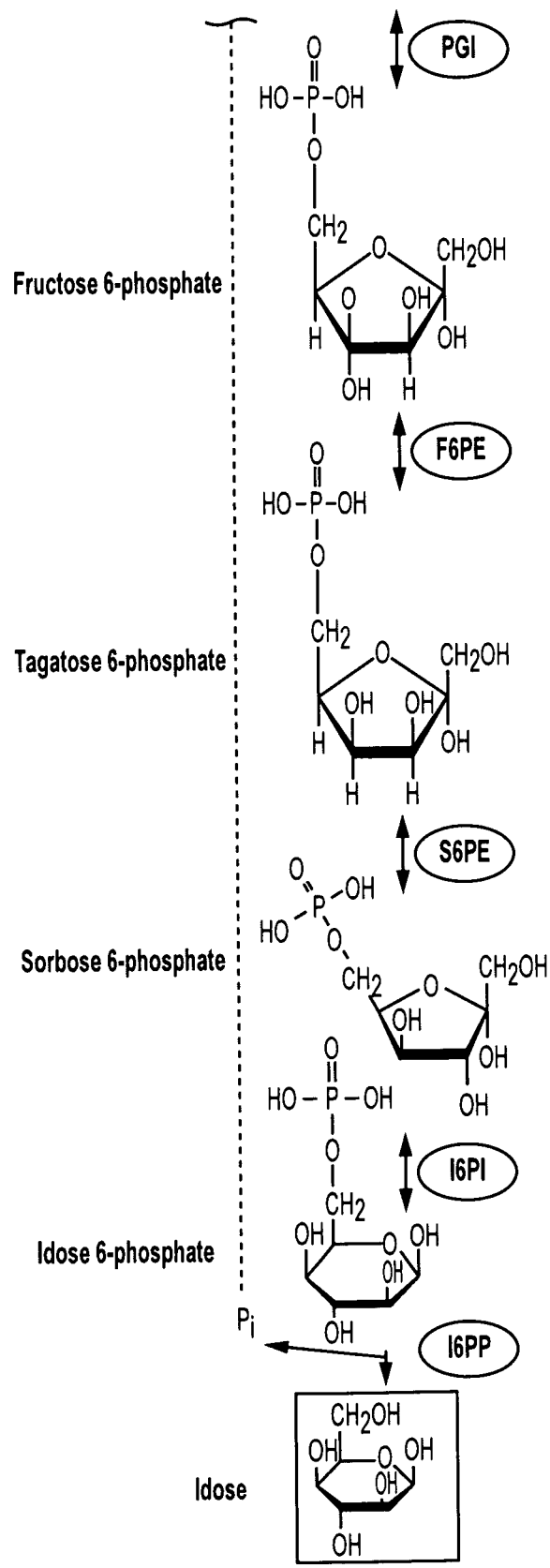

Fructose can also be produced from sucrose via an F6P intermediate. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; F6P to fructose catalyzed by F6PP. An example enzymatic pathway is provided in FIG. 5

The phosphate ions generated when F6P is converted to fructose can then be recycled in the step of converting sucrose to G1P. Additionally, PPFK and polyphosphate can be used to increase fructose yields by producing F6P from fructose generated by the phosphorolytic cleavage of sucrose by SP.

In some embodiments, a process for preparing fructose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to fructose. In certain embodiments, artificial (non-natural) ATP-free enzymatic pathways are provided to convert starch, cellulose, sucrose, and their derived products to fructose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to fructose and increased solubility.

Maltose phosphorylase (MP) can be used to increase fructose yields by phosphorolytically cleaving the degradation product maltose into G1P and glucose. Alternatively, 4-glucan transferase (4GT) can be used to increase fructose yields by recycling the degradation products glucose, maltose, and maltotriose into longer maltooligosaccharides; which can be phosphorolytically cleaved by αGP to yield G1P.

In certain embodiments, cellulose and its derived products can be converted to fructose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to fructose catalyzed by F6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of fructose by phosphorylating the degradation product glucose to G6P.

In other embodiments, fructose can be generated from glucose. The process involves the steps of generating G6P from glucose and polyphosphate catalyzed by polyphosphate glucokinase (PPGK); converting G6P to F6P catalyzed by PGI; converting F6P to fructose catalyzed by F6PP.

Processes of the invention use low-cost starting materials and reduce production costs by decreasing costs associated with the feedstock and product separation. Starch, cellulose, sucrose and some of their derivatives are less expensive feedstocks than, for example, lactose. When fructose is produced from biomass or lactose, yields are lower than in the present invention, and fructose must be separated from other sugars via chromatography, which leads to higher production costs. Furthermore, our process is animal-free.

The step of converting F6P to fructose according to the invention is an irreversible phosphatase reaction, regardless of the feedstock. Therefore, fructose is produced with a very high yield while effectively minimizing the subsequent product separation costs.

In contrast to cell-based manufacturing methods, the invention involves a cell-free preparation of fructose, has relatively high reaction rates due to the elimination of the cell membrane, which often slows down the transport of substrate/product into and out of the cell. It also has a final product free of nutrient-rich fermentation media/cellular metabolites.

Ar particular embodiment of the invention is fructose produced by the processes described herein for producing fructose.

Altrose

One embodiment of the invention is a process for preparing altrose which includes converting fructose 6-phosphate (F6P) to psicose 6-phosphate (P6P) catalyzed by psicose 6-phosphate 3-epimerase (P6PE), converting P6P to altrose 6-phosphate (Alt6P) catalyzed by altrose 6-phosphate isomerase (Alt6PI), and converting the Alt6P produced to altrose catalyzed by altrose 6-phosphate phosphatase.

A process for preparing altrose according to the invention also includes the step of enzymatically converting glucose 6-phosphate (G6P) to the F6P, and this step is catalyzed by phosphoglucoisomerase (PGI). In other embodiments, the process for preparing altrose additionally includes the step of converting glucose 1-phosphate (G1P) to the G6P, where the step is catalyzed by phosphoglucomutase (PGM). In yet further embodiments, altrose production process also includes the step of converting a saccharide to the G1P that is catalyzed at least one enzyme.

Therefore, a process for preparing altrose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to P6P via P6PE, (v) converting P6P to Alt6P via Alt6PI, and (vi) converting Alt6P to altrose via Alt6PP. An example of the enzymatic process where the saccharide is starch is shown in FIG. 1.

Typically, the ratios of enzyme units used in the disclosed process are 1:1:1:1:1:1 (αGP:PGM:PGI:P6PE:Alt6PI:Alt6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of altrose production. For example, a particular enzyme may be present in an amount about 2×, 3×, 4×, 5×, etc. relative to the amount of other enzymes.

Phosphate ions produced by dephosphorylation of Alt6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the altrose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the Alt6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making altrose involves an energetically favorable reaction.

Altrose can also be produced from fructose. For example, the process involves generating F6P from fructose and polyphosphate catalyzed by polyphosphate fructokinase (PPFK); converting F6P to P6P catalyzed by P6PE; converting P6P to Alt6P catalyzed by Alt6PI, and converting Alt6P to altrose catalyzed by Alt6PP. The fructose can be produced, for example, by an enzymatic conversion of sucrose.

Altrose can also be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to P6P catalyzed by P6PE; converting P6P to Alt6P catalyzed by Alt6PI, and converting Alt6P to altrose catalyzed by Alt6PP.

The phosphate ions generated when Alt6P is converted to altrose can then be recycled in the step of converting sucrose to G1P. Additionally, PPFK and polyphosphate can be used to increase altrose yields by producing F6P from fructose generated by the phosphorolytic cleavage of sucrose by SP.

In certain embodiments, a process for preparing altrose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

Several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to altrose and increased solubility.

Maltose phosphorylase (MP) can be used to increase altrose yields by phosphorolytically cleaving the degradation product maltose into G1P and glucose. Alternatively, 4-glucan transferase (4GT) can be used to increase altrose yields by recycling the degradation products glucose, maltose, and maltotriose into longer maltooligosaccharides; which can be phosphorolytically cleaved by αGP to yield G1P.

In certain embodiments, cellulose and its derived products can be converted to altrose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to P6P catalyzed by P6PE; converting P6P to Alt6P catalyzed by Alt6PI, and converting Alt6P to altrose catalyzed by Alt6PP. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

In some embodiments, polyphosphate and polyphosphate glucokinase (PPGK) can be added to the process, thus increasing yields of altrose by phosphorylating the degradation product glucose to G6P.

Altrose can be produced from glucose. The process involves the steps of generating G6P from glucose and polyphosphate catalyzed by polyphosphate glucokinase (PPGK); converting G6P to F6P catalyzed by PGI; converting F6P to P6P catalyzed by P6PE; converting P6P to Alt6P catalyzed by A6PI; and converting Alt6P to altrose catalyzed by Alt6PP.

Processes of the invention for making altrose use low-cost starting materials and reduce production costs by decreasing costs associated with the feedstock and product separation. Starch, cellulose, sucrose and some of their derivatives are less expensive feedstocks than, for example, fructose. When altrose is produced from psiose, yields are lower than in the present invention, and altrose must be separated from psicose via chromatography, which leads to higher production costs.

Also, the step of converting Alt6P to altrose according to the invention is an irreversible phosphatase reaction, regardless of the feedstock. Therefore, altrose is produced with a very high yield while effectively minimizing the subsequent product separation costs.

In contrast to cell-based manufacturing methods, the invention involves a cell-free preparation of altrose, has relatively high reaction rates due to the elimination of the cell membrane, which often slows down the transport of substrate/product into and out of the cell. It also has a final product free of nutrient-rich fermentation media/cellular metabolites.

Ar particular embodiment of the invention is altrose produced by the processes described herein for producing altrose.

Talose

One embodiment of the invention is a process for preparing talose which includes converting fructose 6-phosphate (F6P) to tagatose 6-phosphate (T6P) catalyzed by fructose 6-phosphate 4-epimerase (F6PE), converting T6P to talose 6-phosphate (Tal6P) catalyzed by talose 6-phosphate isomerase (Tal6PI), and converting the Tal6P produced to talose catalyzed by talose 6-phosphate phosphatase (Tal6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing talose according to the invention also includes the step of enzymatically converting glucose 6-phosphate (G6P) to the F6P, and this step is catalyzed by phosphoglucoisomerase (PGI). In other embodiments, the process for preparing talose additionally includes the step of converting glucose 1-phosphate (G1P) to the G6P, where the step is catalyzed by phosphoglucomutase (PGM). In yet further embodiments, talose production process also includes the step of converting a saccharide to the G1P that is catalyzed at least one enzyme.

Therefore, a process for preparing talose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to Tal6P via Tal6PI (EC 5.3.1.26), and (vi) converting Tal6P to talose via Tal6PP. An example of the process where the saccharide is starch is shown in FIG. 3.

Typically, the ratios of enzyme units used in the disclosed process are 1:1:1:1:1:1 (αGP:PGM:PGI:F6PE:Tal6PI:Tal6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of talose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of Tal6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the talose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the Tal6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making talose involves an energetically favorable reaction.

Talose can also be produced from fructose. For example, the process involves generating F6P from fructose and polyphosphate catalyzed by polyphosphate fructokinase (PPFK); converting F6P to T6P catalyzed by F6PE; converting T6P to Tal6P catalyzed by Tal6PI, and converting Tal6P to talose catalyzed by Tal6PP. The fructose can be produced, for example, by an enzymatic conversion of sucrose.

Talose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to Tal6P catalyzed by Tal6PI, and converting Tal6P to talose catalyzed by Tal6PP.

The phosphate ions generated when Tal6P is converted to talose can then be recycled in the step of converting sucrose to G1P. Additionally, PPFK and polyphosphate can be used to increase talose yields by producing F6P from fructose generated by the phosphorolytic cleavage of sucrose by SP.

In some embodiments, a process for preparing talose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to talose. In certain embodiments, artificial (non-natural) ATP-free enzymatic pathways are provided to convert starch, cellulose, sucrose, and their derived products to talose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to talose and increased solubility.

Maltose phosphorylase (MP) can be used to increase talose yields by phosphorolytically cleaving the degradation product maltose into G1P and glucose. Alternatively, 4-glucan transferase (4GT) can be used to increase talose yields by recycling the degradation products glucose, maltose, and maltotriose into longer maltooligosaccharides; which can be phosphorolytically cleaved by αGP to yield G1P.

In certain embodiments, cellulose and its derived products can be converted to talose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to Tal6P catalyzed by Tal6PI, and converting Tal6P to talose catalyzed by Tal6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of talose by phosphorylating the degradation product glucose to G6P.

In other embodiments, talose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to Tal6P catalyzed by Tal6PI; and converting Tal6P to talose catalyzed by Tal6PP.

Processes of the invention use low-cost starting materials and reduce production costs by decreasing costs associated with the feedstock and product separation. Starch, cellulose, sucrose and some of their derivatives are less expensive feedstocks than, for example, lactose. When talose is produced from biomass or lactose, yields are lower than in the present invention, and talose must be separated from other sugars via chromatography, which leads to higher production costs. Furthermore, our process is animal-free.

The step of converting Tal6P to talose according to the invention is an irreversible phosphatase reaction, regardless of the feedstock. Therefore, talose is produced with a very high yield while effectively minimizing the subsequent product separation costs.

In contrast to cell-based manufacturing methods, the invention involves a cell-free preparation of talose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is talose produced by the processes described herein for producing talose.

Sorbose

One embodiment of the invention is a process for preparing sorbose which includes converting fructose 6-phosphate (F6P) to tagatose 6-phosphate (T6P) catalyzed by fructose 6-phosphate 4-epimerase (F6PE), converting T6P to sorbose 6-phosphate (S6P) catalyzed by sorbose 6-phosphate epimerase (S6PE), and converting the S6P produced to sorbose catalyzed by sorbose 6-phosphate phosphatase (S6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing sorbose according to the invention also includes the step of enzymatically converting glucose 6-phosphate (G6P) to the F6P, and this step is catalyzed by phosphoglucoisomerase (PGI). In other embodiments, the process for preparing sorbose additionally includes the step of converting glucose 1-phosphate (G1P) to the G6P, where the step is catalyzed by phosphoglucomutase (PGM). In yet further embodiments, sorbose production process also includes the step of converting a saccharide to the G1P that is catalyzed at least one enzyme.

Therefore, a process for preparing sorbose according to the invention can, for example, include the following steps:

(i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to S6P via S6PE (EC 5.3.1.26), and (vi) converting S6P to sorbose via S6PP. An example of the process where the saccharide is starch is shown in FIG. 3.

Typically, the ratios of enzyme units used in the disclosed process are 1:1:1:1:1:1 (αGP:PGM:PGI:F6PE:S6PE:S6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of sorbose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of S6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the sorbose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the S6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making sorbose involves an energetically favorable reaction.

Sorbose can also be produced from fructose. For example, the process involves generating F6P from fructose and polyphosphate catalyzed by polyphosphate fructokinase (PPFK); converting F6P to T6P catalyzed by F6PE; converting T6P to S6P catalyzed by S6PE, and converting S6P to sorbose catalyzed by S6PP. The fructose can be produced, for example, by an enzymatic conversion of sucrose.

Sorbose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP.

The phosphate ions generated when S6P is converted to sorbose can then be recycled in the step of converting sucrose to G1P. Additionally, PPFK and polyphosphate can be used to increase sorbose yields by producing F6P from fructose generated by the phosphorolytic cleavage of sucrose by SP.

In some embodiments, a process for preparing sorbose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to sorbose. In certain embodiments, artificial (non-natural) ATP-free enzymatic pathways are provided to convert starch, cellulose, sucrose, and their derived products to sorbose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to sorbose and increased solubility.

Maltose phosphorylase (MP) can be used to increase sorbose yields by phosphorolytically cleaving the degradation product maltose into G1P and glucose. Alternatively, 4-glucan transferase (4GT) can be used to increase sorbose yields by recycling the degradation products glucose, maltose, and maltotriose into longer maltooligosaccharides; which can be phosphorolytically cleaved by αGP to yield G1P.

In certain embodiments, cellulose and its derived products can be converted to sorbose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of sorbose by phosphorylating the degradation product glucose to G6P.

In other embodiments, sorbose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to S6P catalyzed by S6PE; and converting S6P to sorbose catalyzed by S6PP.

Processes of the invention use low-cost starting materials and reduce production costs by decreasing costs associated with the feedstock and product separation. Starch, cellulose, sucrose and some of their derivatives are less expensive feedstocks than, for example, lactose. When sorbose is produced from biomass or lactose, yields are lower than in the present invention, and sorbose must be separated from other sugars via chromatography, which leads to higher production costs. Furthermore, our process is animal-free.

The step of converting S6P to sorbose according to the invention is an irreversible phosphatase reaction, regardless of the feedstock. Therefore, sorbose is produced with a very high yield while effectively minimizing the subsequent product separation costs.

In contrast to cell-based manufacturing methods, the invention involves a cell-free preparation of sorbose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is sorbose produced by the processes described herein for producing sorbose.

Gulose

One embodiment of the invention is a process for preparing gulose which includes converting fructose 6-phosphate (F6P) to tagatose 6-phosphate (T6P) catalyzed by fructose 6-phosphate 4-epimerase (F6PE), converting T6P to sorbose 6-phosphate (S6P) catalyzed by sorbose 6-phosphate epimerase (S6PE), converting the S6P produced to gulose 6-phosphate (Gul6P) catalyzed by gulose 6-phosphate isomerase and converting the Gul6P to gulose by gulose 6-phosphate phosphatase (Gul6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing gulose according to the invention also includes the step of enzymatically converting glucose 6-phosphate (G6P) to the F6P, and this step is catalyzed by phosphoglucoisomerase (PGI). In other embodiments, the process for preparing gulose additionally includes the step of converting glucose 1-phosphate (G1P) to the G6P, where the step is catalyzed by phosphoglucomutase (PGM). In yet further embodiments, gulose production process also includes the step of converting a saccharide to the G1P that is catalyzed at least one enzyme.

Therefore, a process for preparing gulose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to S6P via S6PE (EC 5.3.1.26), (vi) converting S6P to Gul6P via Gul6PI, and (vii) converting GuIP to gulose via Gul6PP.

Typically, the ratios of enzyme units used in the disclosed process are 1:1:1:1:1:1:1 (αGP:PGM:PGI:F6PE:S6PE:Gul6PI:GuIPP). To optimize product yields, these ratios can be adjusted in any number of combinations. For example, a ratio of 3:1:1:1:1:1:1 can be used to maximize the concentration of phosphorylated intermediates, which will result in increased activity of the downstream reactions. Conversely, a ratio of 1:1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:1:3 can be used to further increase the reaction rate. Therefore, the enzyme ratios, including other optional enzymes discussed below, can be varied to increase the efficiency of gulose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of S6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the gulose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the S6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making gulose involves an energetically favorable reaction.

Gulose can also be produced from fructose. For example, the process involves generating F6P from fructose and polyphosphate catalyzed by polyphosphate fructokinase (PPFK); converting F6P to T6P catalyzed by F6PE; converting T6P to S6P catalyzed by S6PE, S6P to Gul6P by Gul6PI, and Gul6P to gulose by Gul6PP. The fructose can be produced, for example, by an enzymatic conversion of sucrose.

Gulose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to S6P catalyzed by S6PE, S6P to Gul6P by Gul6PI, and Gul6P to gulose by Gul6PP.

The phosphate ions generated when S6P is converted to sorbose can then be recycled in the step of converting sucrose to G1P. Additionally, PPFK and polyphosphate can be used to increase gulose yields by producing F6P from fructose generated by the phosphorolytic cleavage of sucrose by SP.

In some embodiments, a process for preparing gulose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to gulose. In certain embodiments, artificial (non-natural) ATP-free enzymatic pathways are provided to convert starch, cellulose, sucrose, and their derived products to gulose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to gulose and increased solubility.

Maltose phosphorylase (MP) can be used to increase gulose yields by phosphorolytically cleaving the degradation product maltose into G1P and glucose. Alternatively, 4-glucan transferase (4GT) can be used to increase gulose yields by recycling the degradation products glucose, maltose, and maltotriose into longer maltooligosaccharides; which can be phosphorolytically cleaved by αGP to yield G1P.

In certain embodiments, cellulose and its derived products can be converted to gulose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of gulose by phosphorylating the degradation product glucose to G6P.

In other embodiments, gulose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to S6P catalyzed by S6PE; S6P to Gul6P by Gul6PI, and Gul6P to gulose by Gul6PP.

Processes of the invention use low-cost starting materials and reduce production costs by decreasing costs associated with the feedstock and product separation. Starch, cellulose, sucrose and some of their derivatives are less expensive feedstocks than, for example, lactose. When gulose is produced from biomass or lactose, yields are lower than in the present invention, and gulose must be separated from other sugars via chromatography, which leads to higher production costs. Furthermore, our process is animal-free.

The step of converting S6P to gulose according to the invention is an irreversible phosphatase reaction, regardless of the feedstock. Therefore, gulose is produced with a very high yield while effectively minimizing the subsequent product separation costs.

In contrast to cell-based manufacturing methods, the invention involves a cell-free preparation of gulose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is gulose produced by the processes described herein for producing gulose.

Idose

One embodiment of the invention is a process for preparing idose which includes converting fructose 6-phosphate (F6P) to tagatose 6-phosphate (T6P) catalyzed by fructose 6-phosphate 4-epimerase (F6PE), converting T6P to sorbose 6-phosphate (S6P) catalyzed by sorbose 6-phosphate epimerase (S6PE), converting the S6P produced to idose 6-phosphate (I6P) catalyzed by idose 6-phosphate isomerase and converting the I6P to idose by idose 6-phosphate phosphatase (I6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing idose according to the invention also includes the step of enzymatically converting glucose 6-phosphate (G6P) to the F6P, and this step is catalyzed by phosphoglucoisomerase (PGI). In other embodiments, the process for preparing idose additionally includes the step of converting glucose 1-phosphate (G1P) to the G6P, where the step is catalyzed by phosphoglucomutase (PGM). In yet further embodiments, idose production process also includes the step of converting a saccharide to the G1P that is catalyzed at least one enzyme.

Therefore, a process for preparing idose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to S6P via S6PE (EC 5.3.1.26), (vi) converting S6P to I6P via I6PI, and (vii) converting I6P to idose via I6PP.

Typically, the ratios of enzyme units used in the disclosed process are 1:1:1:1:1:1:1 (αGP:PGM:PGI:F6PE:S6PE:I6PI:I6PP). To optimize product yields, these ratios can be adjusted in any number of combinations. For example, a ratio of 3:1:1:1:1:1:1 can be used to maximize the concentration of phosphorylated intermediates, which will result in increased activity of the downstream reactions. Conversely, a ratio of 1:1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:1:3 can be used to further increase the reaction rate. Therefore, the enzyme ratios, including other optional enzymes discussed below, can be varied to increase the efficiency of idose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of S6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the idose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the S6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making idose involves an energetically favorable reaction.

Idose can also be produced from fructose. For example, the process involves generating F6P from fructose and polyphosphate catalyzed by polyphosphate fructokinase (PPFK); converting F6P to T6P catalyzed by F6PE; converting T6P to S6P catalyzed by S6PE, S6P to I6P by I6PI, and I6P to idose by I6PP. The fructose can be produced, for example, by an enzymatic conversion of sucrose.

Idose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to S6P catalyzed by S6PE, S6P to I6P by I6PI, and I6P to idose by I6PP.

The phosphate ions generated when S6P is converted to sorbose can then be recycled in the step of converting sucrose to G1P. Additionally, PPFK and polyphosphate can be used to increase idose yields by producing F6P from fructose generated by the phosphorolytic cleavage of sucrose by SP.

In some embodiments, a process for preparing idose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to idose. In certain embodiments, artificial (non-natural) ATP-free enzymatic pathways are provided to convert starch, cellulose, sucrose, and their derived products to idose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to idose and increased solubility.

Maltose phosphorylase (MP) can be used to increase idose yields by phosphorolytically cleaving the degradation product maltose into G1P and glucose. Alternatively, 4-glucan transferase (4GT) can be used to increase idose yields by recycling the degradation products glucose, maltose, and maltotriose into longer maltooligosaccharides; which can be phosphorolytically cleaved by αGP to yield G1P.

In certain embodiments, cellulose and its derived products can be converted to idose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of idose by phosphorylating the degradation product glucose to G6P.

In other embodiments, idose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to S6P catalyzed by S6PE; S6P to I6P by I6PI, and I6P to idose by I6PP.

Processes of the invention use low-cost starting materials and reduce production costs by decreasing costs associated with the feedstock and product separation. Starch, cellulose, sucrose and some of their derivatives are less expensive feedstocks than, for example, lactose. When idose is produced from biomass or lactose, yields are lower than in the present invention, and idose must be separated from other sugars via chromatography, which leads to higher production costs. Furthermore, our process is animal-free.

The step of converting S6P to idose according to the invention is an irreversible phosphatase reaction, regardless of the feedstock. Therefore, idose is produced with a very high yield while effectively minimizing the subsequent product separation costs.

In contrast to cell-based manufacturing methods, the invention involves a cell-free preparation of idose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is idose produced by the processes described herein for producing idose.

Tagatose

Processes for making tagatose include converting F6P to T6P, catalyzed by an epimerase; and converting the T6P to tagatose, catalyzed by a phosphatase.

Epimerases suitable for use in the processes to convert F6P to T6P include F6PEs. Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

Phosphatases that convert T6P to tagatose (D-tagatose), T6PPs may be used in a process. Examples of T6PPs include, but are not limited to the following proteins: Uniprot ID O29805, D2RHV2 and F2KMK2. Uniprot IDs O29805 and F2KMK2 both catalyze the F6PE reaction and share 67% amino acid sequence identity. Therefore, examples of T6PPs also include any homologues having at least 65%, preferably at least 70%, more preferably at least 75%, more preferably at least 80%, more preferably at least 85%, even more preferably at least 90%, most preferably at least 95%, and even most preferably at least 96%, 97%, 98%, 99%, or 100% amino acid sequence identity to any of the aforementioned Uniprot IDs.

A process for preparing tagatose also includes the step of enzymatically converting glucose 6-phosphate (G6P) to the F6P, and this step is catalyzed by phosphoglucose isomerase (PGI). The process for preparing tagatose additionally includes the step of converting glucose 1-phosphate (G1P) to the G6P, where the step is catalyzed by phosphoglucomutase (PGM). Furthermore, tagatose production process also includes the step of converting a saccharide to the G1P that is catalyzed at least one enzyme.

Therefore, a process for preparing tagatose, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via fructose 6-phosphate epimerase (F6PE), and (v) converting T6P to tagatose via tagatose 6-phosphate phosphatase (T6PP).

Typically, the ratios of enzyme units used in the process are 1:1:1:1:1 (αGP:PGM:PGI:F6PE:T6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:3 can be used to further increase the reaction rate. Therefore, the enzyme ratios, including other optional enzymes discussed below, can be varied to increase the efficiency of tagatose production. For example, a particular enzyme may be present in an amount about 2×, 3×, 4×, 5×, etc. relative to the amount of other enzymes.

Tagatose can also be produced from fructose. For example, the process involves generating F6P from fructose and polyphosphate catalyzed by polyphosphate fructokinase (PPFK); converting F6P to T6P catalyzed by F6PE; and converting T6P to tagatose catalyzed by T6PP. The fructose can be produced, for example, by an enzymatic conversion of sucrose.

Tagatose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; and converting T6P to tagatose catalyzed by T6PP.

The phosphate ions generated when T6P is converted to tagatose can then be recycled in the step of converting sucrose to G1P. Additionally, PPFK and polyphosphate can be used to increase tagatose yields by producing F6P from fructose generated by the phosphorolytic cleavage of sucrose by SP.

A process for preparing tagatose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

Cellulose and its derived products can be converted to tagatose through a series of steps. The process involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; and converting T6P to tagatose catalyzed by T6PP. In this process, the phosphate ions can be recycled by the step of converting cellodextrin and cellobiose to G1P.

Tagatose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; and converting T6P to tagatose catalyzed by T6PP.

Psicose

Processes for making psicose include converting fructose 6-phosphate (F6P) to psicose 6-phosphate (P6P) catalyzed by an epimerase (e.g., psicose 6-phosphate 3-epimerase, P6PE) and converting the P6P produced to psicose catalyzed by a phosphatase (e.g., psicose 6-phosphate phosphatase, P6PP).

Examples of P6PEs include, but are not limited to the following proteins, identified by UNIPROT ID numbers: D9TQJ4, A0A0901XZ8, and P32719. Uniprot IDs A0A0901XZ8 and D9TQJ4 both catalyze the P6PE reaction and share 45% amino acid sequence identity. Therefore, examples of P6PEs also include any homologues having at least 45%, preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96, 97, 98, 99 or 100% to any of the aforementioned Uniprot IDs.

Examples of P6PPs include, but are not limited to the following proteins: Uniprot ID. A3DC21, Q5LGR4, and Q89ZR1. Uniprot IDs A3DC21 and Q89ZR1 both catalyze the P6PP reaction and share 45% amino acid sequence identity. Therefore, examples of P6PPs also include any homologues having at least 45%, preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96, 97, 98, 99 or 100% to any of the aforementioned Uniprot IDs.

A process for preparing psicose also includes the step of enzymatically converting glucose 6-phosphate (G6P) to the F6P, and this step is catalyzed by phosphoglucose isomerase (PGI). The process for preparing psicose additionally includes the step of converting glucose 1-phosphate (G1P) to the G6P, where the step is catalyzed by phosphoglucomutase (PGM). Furthermore, psicose production process also includes the step of converting a saccharide to the G1P that is catalyzed at least one enzyme.

Therefore, a process for preparing psicose, for example, include the following steps: (i) converting a saccharide to glucose 1-phosphate (G1P) using one or more enzymes; (ii)

converting G1P to G6P using phosphoglucomutase (PGM, EC 5.4.2.2); (iii) converting G6P to F6P using phosphoglucoisomerase (PGI, EC 5.3.1.9); (iv) converting F6P to P6P via psicose 6-phosphate epimerase (P6PE), and (v) converting P6P to psicose via psicose 6-phosphate phosphatase (P6PP).

Typically, the ratios of enzyme units used in the process are 1:1:1:1:1 (αGP:PGM:PGI:P6PE:P6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1, 4-glycosidic bonds. A ratio of enzymes, for example, 3:1:1:1:3 can be used to further increase the reaction rate. Therefore, the enzyme ratios, including other optional enzymes discussed below, can be varied to increase the efficiency of tagatose production. For example, a particular enzyme may be present in an amount about 2×, 3×, 4×, 5×, etc. relative to the amount of other enzymes.

Psicose can also be produced from fructose. For example, the process involves generating F6P from fructose and polyphosphate catalyzed by polyphosphate fructokinase (PPFK); converting F6P to P6P catalyzed by P6PE; and converting P6P to psicose catalyzed by P6PP. The fructose can be produced, for example, by an enzymatic conversion of sucrose.

Psicose can be produced from sucrose. The process includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to P6P catalyzed by P6PE; and converting P6P to psicose catalyzed by P6PP.

The phosphate ions generated when P6P is converted to psicose can then be recycled in the step of converting sucrose to G1P. Additionally, PPFK and polyphosphate can be used to increase psicose yields by producing F6P from fructose generated by the phosphorolytic cleavage of sucrose by SP.

A process for preparing psicose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

Cellulose and its derived products can be converted to psicose through a series of steps. The process involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to P6P catalyzed by P6PE; and converting P6P to psicose catalyzed by P6PP. In this process, the phosphate ions can be recycled by the step of converting cellodextrin and cellobiose to G1P.

Psicose can be generated from glucose. The process involves the steps of generating G6P from glucose and polyphosphate catalyzed by polyphosphate glucokinase (PPGK); converting G6P to F6P catalyzed by PGI; converting F6P to P6P catalyzed by P6PE; and converting P6P to psicose catalyzed by P6PP.

EXAMPLES

Materials and Methods

Chemicals

All chemicals, including corn starch, soluble starch, maltodextrins, glucose, filter paper were reagent grade or higher and purchased from Sigma-Aldrich (St. Louis, Mo., USA) or Fisher Scientific (Pittsburgh, Pa., USA), unless otherwise noted. Restriction enzymes, T4 ligase, and Phusion DNA polymerase were purchased from New England Biolabs (Ipswich, Mass., USA). Oligonucleotides were synthesized either by Integrated DNA Technologies (Coralville, Iowa, USA) or Eurofins MWG Operon (Huntsville, Ala., USA). Regenerated amorphous cellulose used in enzyme purification was prepared from Avicel PH105 (FMC BioPolymer, Philadelphia, Pa., USA) through its dissolution and regeneration, as described in: Ye et al., Fusion of a family 9 cellulose-binding module improves catalytic potential of *Clostridium thermocellum* cellodextrin phosphorylase on insoluble cellulose. Appl. Microbiol. Biotechnol. 2011; 92:551-560. *Escherichia coli* Sig10 (Sigma-Aldrich, St. Louis, Mo., USA) was used as a host cell for DNA manipulation and *E. coli* BL21 (DE3) (Sigma-Aldrich, St. Louis, Mo., USA) was used as a host cell for recombinant protein expression. ZYM-5052 media including either 100 mg $L^{-1}$ ampicillin or 50 mg $L^{-1}$ kanamycin was used for *E. coli* cell growth and recombinant protein expression. Cellulase from *Trichoderma reesei* (Catalog number: C2730) and pullulanase (Catalog number: P1067) were purchased from Sigma-Aldrich (St. Louis, Mo., USA) and produced by Novozymes (Franklinton, N.C., USA). Maltose phosphorylase (Catalog number: M8284) was purchased from Sigma-Aldrich.

Production and Purification of Recombinant Enzymes

The *E. coli* BL21 (DE3) strain harboring a protein expression plasmid was incubated in a 1-L Erlenmeyer flask with 100 mL of ZYM-5052 media containing either 100 mg $L^{-1}$ ampicillin or 50 mg $L^{-1}$ kanamycin. Cells were grown at 37° C. with rotary shaking at 220 rpm for 16-24 hours. The cells were harvested by centrifugation at 12° C. and washed once with either 20 mM phosphate buffered saline (pH 7.5) containing 50 mM NaCl and 5 mM $MgCl_2$ (heat precipitation and cellulose-binding module) or 20 mM phosphate buffered saline (pH 7.5) containing 300 mM NaCl and 5 mM imidazole (Ni purification). The cell pellets were re-suspended in the same buffer and lysed by ultra-sonication (Fisher Scientific Sonic Dismembrator Model 500; 5 s pulse on and 10 s off, total 21 min at 50% amplitude). After centrifugation, the target proteins in the supernatants were purified.

Three approaches were used to purify the various recombinant proteins. His-tagged proteins were purified by the Ni Sepharose 6 Fast Flow resin (GE Life Sciences, Marlborough, Mass., USA). Fusion proteins containing a cellulose-binding module (CBM) and self-cleavage intein were purified through high-affinity adsorption on a large surface-area regenerated amorphous cellulose. Heat precipitation at 70-95° C. for 5-30 min was used to purify hyperthermostable enzymes. The purity of the recombinant proteins was examined by sodium dodecyl sulfate polyacrylamide gel electrophoresis (SDS-PAGE).

Enzymes Used and their Activity Assays

Alpha-glucan phosphorylase (αGP) from *Thermotoga maritima* (Uniprot ID G4FEH8) was used. Activity was assayed in 50 mM sodium phosphate buffer (pH 7.2) containing 1 mM $MgCl_2$, and 30 mM maltodextrin at 50° C. The reaction was stopped via filtration of enzyme with a Vivaspin 2 concentrator (10,000 MWCO) (Vivaproducts, Inc., Littleton, Mass., USA). Glucose 1-phosphate (G1P) was measured using a glucose hexokinase/G6PDH assay kit (Sigma Aldrich, Catalog No. GAHK20-1KT) supplemented with 25 U/mL phosphoglucomutase. A unit (U) is described as µmol/min.

Phosphoglucomutase (PGM) from *Thermococcus kodakaraensis* (Uniprot ID Q68BJ6) was used. Activity was measured in 50 mM HEPES buffer (pH 7.2) containing 5 mM $MgCl_2$ and 5 mM G1P at 50° C. The reaction was stopped via filtration of enzyme with a Vivaspin 2 concentrator (10,000 MWCO). The product glucose 6-phosphate (G6P) was determined using a hexokinase/G6PDH assay kit (Sigma Aldrich, Catalog No. GAHK20-1KT).

Two different sources of phosphoglucoisomerase (PGI) were used from *Clostridium thermocellum* (Uniprot ID A3DBX9) and *Thermus thermophilus* (Uniprot ID Q5SLL6). Activity was measured in 50 mM HEPES buffer (pH 7.2) containing 5 mM $MgCl_2$ and 10 mM G6P at 50° C. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P. This 200 µL reaction contained 50 mM HEPES (pH 7.2), 5 mM $MgCl_2$, 10 mM G6P, 1.5 mM ATP, 1.5 mM phosphoenol pyruvate, 200 µM NADH, 0.1 U PGI, 5 U PK, and 5 U LD.

The recombinant cellodextrin phosphorylase and cellobiose phosphorylase from *C. thermocellum* are described in Ye et al. Spontaneous high-yield production of hydrogen from cellulosic materials and water catalyzed by enzyme cocktails. ChemSusChem 2009; 2:149-152. Their activities were assayed as described.

The recombinant polyphosphate glucokinase from *Thermobilida fusca* YX is described in Liao et al., One-step purification and immobilization of thermophilic polyphosphate glucokinase from *Thermobilida fusca* YX: glucose-6-phosphate generation without ATP. Appl. Microbiol. Biotechnol. 2012; 93:1109-1117. Its activities were assayed as described.

The recombinant isoamylase from *Sulfolobus tokodaii* is described in Cheng et al., Doubling power output of starch biobattery treated by the most thermostable isoamylase from an archaeon *Sulfolobus tokodaii*. Scientific Reports 2015; 5:13184. Its activities were assayed as described.

The recombinant 4-alpha-glucanoltransferase from *Thermococcus litoralis* is described in Jeon et al. 4-α-Glucanotransferase from the Hyperthermophilic Archaeon *Thermococcus Litoralis*. Eur. J. Biochem. 1997; 248:171-178. Its activity was measured as described.

Sucrose phosphorylase from *Thermoanaerobacterium thermosaccharolyticum* (Uniprot ID D9TT09) was used (Verhaeghe et al. The quest for a thermostable sucrose phosphorylase reveals sucrose 6'-phosphate phosphorylase as a novel specificity. Appl Microbiol Biotechnol. 2014 August; 98(16):7027-37). Its activity was measured in 50 mM HEPES buffer (pH 7.5) containing 10 mM sucrose and 12 mM organic phosphate. Glucose 1-phosphate (G1P) was measured using a glucose hexokinase/G6PDH assay kit supplemented with 25 U/mL phosphoglucomutase as with alpha-glucan phosphorylase.

Psicose 6-phosphate 3-epimerase (P6PE) from *Thermoanaerobacterium thermosaccharolyticum* (Uniprot ID D9TQJ4) was used. Activity was measured in 50 mM HEPES buffer (pH 7.2) containing 5 mM $MgCl_2$, 500 µM $CoCl_2$, 1 U/mL P6PP, and 10 mM F6P at 50° C. The reaction was stopped via filtration of enzyme with a Vivaspin 2 concentrator (10,000 MWCO). The product, psicose 6-phosphate (P6P), was determined using Psicose 6-phosphate phosphatase and detecting free phosphate release. To detect free phosphate release, 500 µL of a solution containing 0.1 M zinc acetate and 2 mM ammonium molybdate (pH 5) was added to 50 µL of reaction. This was mixed and followed by 125 µL of 5% ascorbic acid (pH 5). This solution was mixed then incubated at 30° C. for 20 min. The absorbance at 850 nm was read to determine free phosphate release. Psicose was then verified via HPLC using an Agilent Hi-Plex H-column (sample and control run with 5 mM $H_2SO_4$ at 0.6 mL/min and 65° C.)

Allose 6-phosphate isomerase (A6PI) from *Clostridium thermocellum* (Uniprot ID W4V2C8) with the amino acid sequence set forth in SEQ ID NO: 1 was used. Activity was measured in 50 mM HEPES buffer (pH 7.2) containing 5 mM $MgCl_2$, 500 µM $CoCl_2$, 1 U/mL P6PE, 1 U/mL A6PP, and 10 mM F6P at 50° C. The reaction was stopped via filtration of enzyme with a Vivaspin 2 concentrator (10,000 MWCO). The product, allose 6-phosphate (P6P), was determined using allose 6-phosphate phosphatase and detecting free phosphate release as described for P6PE. Allose verified via HPLC the same as psicose. Another A6PI, such as A6PI from *Symbiobacterium thermophilum* (Uniprot ID Q67LX4) with the amino acid sequence set forth in SEQ ID NO: 2, may be used.

Allose 6-phosphate phosphatase (A6PP) from *Rubellimicrobium thermophilum* (Uniprot ID S9SDA3) with the amino acid sequence set forth in SEQ ID NO: 3 was used. Activity was measured in 50 mM HEPES buffer (pH 7.2) containing 5 mM $MgCl_2$, 500 µM $CoCl_2$, 1 U/mL P6PE, 1 U/mL A6PI, and 10 mM F6P at 50° C. The reaction was stopped via filtration of enzyme with a Vivaspin 2 concentrator (10,000 MWCO). The product, allose, was determined by detecting free phosphate release as described for P6PE. Allose verified via HPLC the same as psicose. Other A6PPs, such as A6PP from *Thermotoga maritima* (Uniprot ID Q9X0Y1) with the amino acid sequence set forth in SEQ ID NO: 4, A6PP from *Thermoanaerobacterium saccharolyticum* (Uniprot ID I3VT81) with the amino acid sequence set forth in SEQ ID NO: 5, A6PP from *Streptomyces thermoautotrophicus* (Uniprot ID A0A132NF06) with the amino acid sequence set forth in SEQ ID NO: 6, and A6PP from *Sphaerobacter thermophilus* (Uniprot ID D1C7G9) with the amino acid sequence set forth in SEQ ID NO: 7, may be used.

Mannose 6-phosphate isomerase (M6PI) from *Pseudonocardia thermophila* (Uniprot ID A0A1M6TLY7) with the amino acid sequence set forth in SEQ ID NO: 8 was used. Activity was measured in 50 mM HEPES buffer (pH 7.2) containing 5 mM $MgCl_2$, 1 U/mL PGI, 1 U/mL M6PP, and 10 mM F6P at 50° C. The reaction was stopped via filtration of enzyme with a Vivaspin 2 concentrator (10,000 MWCO). The product, mannose 6-phosphate (M6P), was determined using mannose 6-phosphate phosphatase (M6PP) and detecting free phosphate release as described for P6PE. Mannose verified via HPLC the same as psicose. Other M6PIs such as M6PI from *Caldithrix abyssi* (Uniprot ID H1XQS6) with the amino acid sequence set forth in SEQ ID NO: 9, M6PI from *Myceliophthora thermophila* (Uniprot ID G2Q982) with the amino acid sequence set forth in SEQ ID NO: 10 and M6PI from *Treponema caldarium* (Uniprot ID F8F1Z8) with the amino acid sequence set forth in SEQ ID NO: 11 may be used.

Mannose 6-phosphate phosphatase (M6PP) from *Tepidimonas fonticaldi* (Uniprot ID A0A1A6DS13) with the amino acid sequence set forth in SEQ ID NO: 12 was used. Activity was measured in 50 mM HEPES buffer (pH 7.2) containing 5 mM $MgCl_2$, and 10 mM mannose 6-phosphate at 50° C. The reaction was stopped via filtration of enzyme with a Vivaspin 2 concentrator (10,000 MWCO). The product, mannose, was determined by detecting free phosphate release as described for P6PE. Mannose verified via HPLC the same as psicose. Other M6PP such as M6PP from *Thermomonas hydrothermalis* (Uniprot ID A0A1M4UN08) with the amino acid sequence set forth in SEQ ID NO: 13 and M6PP from *Sulfurivirga caldicuralii* (Uniprot ID A0A1N6FCW3) with the amino acid sequence set forth in SEQ ID NO: 14 may be used.

Bifunctional phosphoglucose/phosphomannose isomerase (PGPMI) from *Syntrophothermus lipocalidus* (Uniprot ID D7CPH7) with the amino acid sequence set forth in SEQ ID NO: 15 was used. Activity was measured in 50 mM HEPES buffer (pH 7.2) containing 5 mM $MgCl_2$, 1 U/mL M6PP, and 10 mM G6P at 50° C. The reaction was stopped via filtration of enzyme with a Vivaspin 2 concentrator (10,000 MWCO). The product, M6P, was determined using M6PP and detecting free phosphate release as described for P6PE. Mannose verified via HPLC the same as psicose. Other PGPMI such as PGPMI from *Schleiferia thermophila* (Uniprot ID A0A085L170) with the amino acid sequence set forth in SEQ ID NO: 16 and PGPMI from *Thermodesulfobium narugense* (Uniprot ID M1E6Z3) with the amino acid sequence set forth in SEQ ID NO: 17 may be used.

Galactose 6-phosphate isomerase (Gal6PI) from *Lactococcus lactis* (obligate dimer; Uniprot IDs P23494 and P23495 with the amino acid sequences set forth in SEQ ID NO: 18 and 19, respectively) is used (van Rooijen et al. *Molecular Cloning, Characterization, and Nucleotide Sequence of the Tagatose 6-Phosphate Pathway Gene Cluster of the Lactose Operon of Lactococcus Zactis.* J. Biol. Chem. 1991; 266:7176-7181). Activity is measured in 50 mM HEPES buffer (pH 7.2) containing 5 mM $MgCl_2$, 1 U/mL fructose 6-phosphate 4-epimerase (F6PE), 1 U/mL galactose 6-phosphate phosphatase (Gal6PP), and 10 mM fructose 6-phosphate at 37° C. The reaction is stopped via filtration of enzyme with a Vivaspin 2 concentrator (10,000 MWCO). The product, galactose 6-phosphate (gal6P), is determined using Gal6PP and detecting free phosphate release as described for P6PE. Galactose verified via HPLC the same as psicose.

Galactose 6-phosphate phosphatase (Gal6PP) from *Bacteroides thetaiotaomicron* (Uniprot ID Q8A2F3) with the amino acid sequence set forth in SEQ ID NO: 20 was used. Activity was measured in 50 mM HEPES buffer (pH 7.2) containing 5 mM $MgCl_2$, and 10 mM galactose 6-phosphate at 50° C. The reaction was stopped via filtration of enzyme with a Vivaspin 2 concentrator (10,000 MWCO). The product, galactose, was determined by detecting free phosphate release as described for P6PE. Galactose verified via HPLC the same as psicose.

Fructose 6-phosphate phosphatase (F6PP) from *Halothermothrix orenii* (Uniprot ID B8CWV3) with the amino acid sequence set forth in SEQ ID NO: 21 was used. Activity was measured in 50 mM HEPES buffer (pH 7.2) containing 5 mM $MgCl_2$, and 10 mM fructose 6-phosphate at 50° C. The reaction was stopped via filtration of enzyme with a Vivaspin 2 concentrator (10,000 MWCO). The product, fructose, was determined by detecting free phosphate release as described for P6PE. Fructose verified via HPLC the same as psicose.

Tagatose 6-phosphate phosphatase (TEPP) from *Archaeoglobus fugidis* (Uniprot ID A0A075WB87) was used. Activity was measured in 50 mM HEPES buffer (pH 7.2) containing 5 mM $MgCl_2$ and 10 mM T6P at 50° C. The reaction was stopped via filtration of enzyme with a Vivaspin 2 concentrator (10,000 MWCO). Tagatose production was determined by detecting free phosphate release as described for F6PE.

Psicose 6-phosphate phosphatase (P6PP) from *Clostridium thermocellum* (UNIPROT ID A3DC21), was used. Activity was measured in 50 mM HEPES buffer (pH 7.2) containing 5 mM MgCl2, 80 µM CoCl2, 1 U/mL P6PE, and 10 mM F6P at 50° C. The reaction was stopped via filtration of enzyme with a Vivaspin 2 concentrator (10,000 MWCO). The product, psicose, was determined through detecting free phosphate release as described for P6PE.

Enzyme units used in each Example below can be increased or decreased to adjust the reaction time as desired. For example, if one wanted to perform Example 9 in 8 h instead of 24 h, the units of the enzymes would be increased about 3-fold. Conversely, if one wanted perform example 9 in 48 h instead of 24 h the enzyme units could be decreased about 2-fold. These examples illustrate how the amount of enzyme units can be used to increase or decrease reaction time while maintaining constant productivity.

All Products

Example 1

To validate the technical feasibility of the enzymatic biosynthesis of fructose 6-phosphate from starch, three enzymes were recombinantly expressed: alpha-glucan phosphorylase from *T. maritima* (Uniprot ID G4FEH8), phosphoglucomutase from *Thermococcus kodakaraensis* (Uniprot ID Q68BJ6), and phosphoglucoisomerase from *Clostridium thermocellum* (Uniprot ID A3DBX9). The recombinant proteins were over-expressed in *E. coli* BL21 (DE3) and purified as described above.

A 0.20 mL reaction mixture containing 10 g/L soluble starch, 50 mM phosphate buffered saline pH 7.2, 5 mM $MgCl_2$, 0.5 mM $ZnCl_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 2

Same tests as in Example 1 (other than reaction temperatures) were carried out from 40 to 80° C. It was found that 10 g/L soluble starch produced 0.9 g/L F6P at 40° C. and 3.6 g/L F6P at 80° C. after 40 hour reactions. These results suggest that increasing reaction temperature for this set of enzymes increased F6P yields, but too high of temperature may impair some enzyme activity.

Example 3

It was found that, at 80° C., an enzyme ratio of αGP: PGM:PGI of approximately 1:1:1 resulted in fast F6P generation. It was noted that the enzyme ratio did not influence final F6P concentration greatly if the reaction time was long enough. However, the enzyme ratio affects reaction rates and the total cost of enzymes used in the system.

Example 4

A 0.20 mL reaction mixture containing 10 g/L maltodextrin, 50 mM phosphate buffered saline pH 7.2, 5 mM MgCl$_2$, 0.5 mM ZnCl$_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 5

To test for F6P production from Avicel, Sigma cellulase was used to hydrolyze cellulose at 50° C. To remove beta-glucosidase from commercial cellulase, 10 filter paper units/mL of cellulase was mixed to 10 g/L Avicel at an ice-water bath for 10 min. After centrifugation at 4° C., the supernatant containing beta-glucosidase was decanted. Avicel that was bound with cellulase containing endoglucanase and cellobiohydrolase was resuspended in a citrate buffer (pH 4.8) for hydrolysis at 50° C. for three days. The cellulose hydrolysate was mixed with 5 U/mL cellodextrin phosphorylase, 5 U/L cellobiose phosphorylase, 5 U/mL of αGP, 5 U/mL PGM, and 5 U/mL PGI in a 100 mM HEPES buffer (pH 7.2) containing 10 mM phosphate, 5 mM MgCl$_2$ and 0.5 mM ZnCl$_2$. The reaction was conducted at 60° C. for 72 hours and high concentrations of F6P were found (small amounts of glucose and no cellobiose). F6P was detected using the coupled enzyme assay described above. Glucose was detected using a hexokinase/G6PDH assay kit as described above.

Example 6

To increase F6P yields from Avicel, Avicel was pretreated with concentrated phosphoric acid to produce amorphous cellulose (RAC), as described in Zhang et al. A transition from cellulose swelling to cellulose dissolution by o-phosphoric acid: evidence from enzymatic hydrolysis and supramolecular structure. Biomacromolecules 2006; 7:644-648. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was resuspended in a citrate buffer (pH 4.8) for hydrolysis at 50° C. for 12 hours. The RAC hydrolysate was mixed with 5 U/mL cellodextrin phosphorylase, 5 U/mL cellobiose phosphorylase, 5 U/mL of αGP, 5 U/mL PGM, and 5 U/mL PGI in a 100 mM HEPES buffer (pH 7.2) containing 10 mM phosphate, 5 mM MgCl$_2$ and 0.5 mM ZnCl$_2$. The reaction was conducted at 60° C. for 72 hours. High concentrations of F6P and glucose were recovered because no enzymes were added to convert glucose to F6P. F6P was detected using the coupled enzyme assay described above. Glucose was detected using a hexokinase/G6PDH assay kit as described above.

Example 7

To further increase F6P yields from RAC, polyphosphate glucokinase and polyphosphate were added. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was re-suspended in a citrate buffer (pH 4.8) for hydrolysis at 50° C. was incubated in a citrate buffer (pH 4.8) for hydrolysis at 50° C. for 12 hours. The RAC hydrolysate was mixed with 5 U/mL polyphosphate glucokinase, 5 U/mL cellodextrin phosphorylase, 5 U/mL cellobiose phosphorylase, 5 U/mL of αGP, 5 U/mL PGM, and 5 U/mL PGI in a 100 mM HEPES buffer (pH 7.2) containing 50 mM polyphosphate, 10 mM phosphate, 5 mM MgCl$_2$ and 0.5 mM ZnCl$_2$. The reaction was conducted at 50° C. for 72 hours. F6P was found in high concentrations with only small amounts of glucose now present. F6P was detected using the coupled enzyme assay described above. Glucose was detected using a hexokinase/G6PDH assay kit as described above.

Example 8

To determine the concentration range of phosphate buffered saline (PBS), a 0.20 mL reaction mixture containing 50 g/L maltodextrin; 6.25 mM, 12.5 mM, 25 mM, 37.5 mM, or 50 mM phosphate buffered saline pH 7.2; 5 mM MgCl2; 0.1 U of αGP; 0.1 U PGM; and 0.1 U PGI was incubated at 50° C. for 6 hours. The short duration ensures completion was not reached, and therefore differences in efficiency can be clearly seen. Production of F6P was quantified using a fructose 6-phosphate kinase (F6PK)/pyruvate dehydrogenase (PK)/lactate dehydrogenase (LD) coupled enzyme assay where a decrease in absorbance at 340 nm indicates production of F6P. Respectively, a yield of 4.5 g/L, 5.1 g/L, 5.6 g/L, 4.8 g/L, or 4.9 g/L F6P was obtained for the reactions containing either 6.25 mM, 12.5 mM, 25 mM, 37.5 mM, or 50 mM phosphate buffered saline pH 7.2 (Table 1). These results indicate that a concentration of 25 mM PBS pH 7.2 was ideal for these particular reaction conditions. It is important to note that even the use of 6.25 mM PBS at pH 7.2 results in significant turnover due to phosphate recycling. This shows that the disclosed phosphate recycling methods are able to keep phosphate levels low even at industrial levels of volumetric productivity (e.g., 200-300 g/L maltodextrin).

TABLE 1

| Concentration of PBS pH 7.2 (mM) | g/L of F6P |
|---|---|
| 6.25 | 4.5 |
| 12.5 | 5.1 |
| 25 | 5.6 |
| 37.5 | 4.8 |
| 50 | 4.9 |

Example 9

To determine the pH range of the cascade reaction, a 0.20 mL reaction mixture containing 50 g/L maltodextrin; 50 mM phosphate buffered saline pH 6.0, 6.2, 6.4, 6.6, 6.8, 7.0 7.2, or 7.3; 5 mM MgCl2; 0.02 U of αGP; 0.02 U PGM; and 0.02 U PGI was incubated at 50° C. for 16 hours. The units are lowered to ensure completion was not reached, and therefore differences in efficiency can be clearly seen. Production of F6P was quantified as in example 12. Respectively, a yield of 4.0 g/L, 4.1 g/L 4.2 g/L, 4.1 g/L, 4.4 g/L, 4.1 g/L, 3.8 g/L or 4.0 g/L F6P was obtained for reactions containing 50 mM phosphate buffered saline at pH 6.0, 6.2, 6.4, 6.6, 6.8, 7.0, 7.2, or 7.3 (Table 2). These results indicate that a pH of 6.8 was ideal for these particular reaction conditions, although the system works through a wide pH range.

TABLE 2

| pH of PBS | g/L of F6P |
|---|---|
| 6.0 | 4.0 |
| 6.2 | 4.1 |
| 6.4 | 4.2 |
| 6.6 | 4.1 |
| 6.8 | 4.4 |
| 7.0 | 4.1 |
| 7.2 | 3.8 |
| 7.3 | 4.0 |

Allose

Example 10

To validate allose production from F6P, 10 g/L F6P was mixed with 1 U/mL P6PE, 1 U/mL A6PI and 1 U/mL A6PP in 50 mM HEPES buffer (pH 7.2) containing 5 mM $MgCl_2$ and 500 µM $CoCl_2$. The reaction was incubated for 3 hours at 50° C. Conversion of F6P to allose was seen via HPLC (Agilent 1100 series) using an Agilent Hi-Plex H-column and refractive index detector. The sample and control were run in 5 mM $H_2SO_4$ at 0.6 mL/min and 65° C.

Example 11

To validate production of allose from maltodextrin, a 0.20 mL reaction mixture containing 20 g/L maltodextrin, 50 mM phosphate buffered saline pH 7.2, 5 mM $MgCl_2$, 500 µM $CoCl_2$, 0.05 U of αGP, 0.05 U PGM, 0.05 U PGI, 0.05 U P6PE, 0.05 U A6PI and 0.05 U A6PP was incubated at 50° C. for 24 hours. The reaction was stopped via filtration of enzyme with a Vivaspin 2 concentrator (10,000 MWCO). Allose was verified via HPLC as described in Example 10.

Example 12

A reaction mixture containing 200 g/L maltodextrin, 10 mM acetate buffer (pH 5.5), 5 mM $MgCl_2$, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM $MgCl_2$, 500 µM $CoCl_2$, 0.05 U of αGP, 0.05 U PGM, 0.05 U PGI, 0.05 U P6PE, 0.05 U A6PI, and 0.05 U A6PP was incubated at 50° C. for 24 hours. Production of allose was verified as in Example 10.

Example 13

To further increase allose yields from maltodextrin, 0.05 U 4-glucan transferase (4GT) was added to the reaction described in Example 11.
A 0.2 mL reaction mixture containing 20 g/L isoamylase treated maltodextrin (see Example 12), 50 mM phosphate buffered saline pH 7.2, 5 mM $MgCl_2$, 500 µM $CoCl_2$, 0.05 U of αGP, 0.05 U PGM, 0.05 U PGI, 0.05 U P6PE, 0.05 U A6PI, 0.05 U A6PP, and 0.05 U 4GT was incubated at 50° C. for 24 hours. Production of allose was verified as in Example 10.

Example 14

To further increase allose yields from maltodextrin, 0.05 U maltose phosphorylase is added to the reaction described in Example 11.

Example 15

To further increase allose yields from maltodextrin, 0.05 U polyphosphate glucokinase and 75 mM polyphosphate is added to the reaction described in Example 11.

Example 16

To produce allose from fructose, a reaction mixture containing 10 g/L fructose, 50 mM Tris buffer pH 7.0, 75 mM polyphosphate, 5 mM $MgCl_2$, 500 µM $CoCl_2$, 0.05 U fructose polyphosphate kinase, 0.05 U P6PE, 0.05 A6PI, and 0.05 U A6PP is incubated at 50° C. for 24 hours. Production of allose is quantified as in Example 10.

Example 17

To produce allose from glucose, a reaction mixture containing 10 g/L glucose, 50 mM Tris buffer pH 7.0, 75 mM polyphosphate, 5 mM $MgCl_2$, 500 µM $CoCl_2$, 0.05 U glucose polyphosphate kinase, 0.05 U PGI, 0.05 U P6PE, 0.05 A6PI, and 0.05 U A6PP is incubated at 50° C. for 24 hours. Production of allose is quantified as in Example 10.

Example 18

To produce allose from sucrose, a reaction mixture containing 10 g/L sucrose, 50 mM phosphate buffered saline pH 7.0, 5 mM $MgCl_2$, 500 µM $CoCl_2$, 0.05 U sucrose phosphorylase, 0.05 PGM, 0.05 U PGI, 0.05 U P6PE, 0.05 A6PI, and 0.05 U A6PP is incubated at 50° C. for 24 hours. Production of allose is quantified as in Example 10.

Example 19

To further increase yields of allose from sucrose, 75 mM polyphosphate and 0.05 polyphosphate fructokinase is added to the reaction mixture in Example 18. Production of allose is quantified as in Example 10.

Mannose

Example 20

To validate mannose production from F6P, 10 g/L F6P was mixed with 1 U/mL M6PI/PGPMI, and 1 U/mL M6PP in 50 mM HEPES buffer (pH 7.2) containing 5 mM $MgCl_2$. The reaction was incubated for 3 hours at 50° C. Conversion of F6P to mannose was seen via HPLC (Agilent 1100 series) using an Agilent Hi-Plex H-column and refractive index detector. The sample and control were run in 5 mM $H_2SO_4$ at 0.6 mL/min and 65° C.

Example 21

To validate production of mannose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U M6PI/PGPMI (no PGI needed in PGPMI case), and 0.05 U M6PP was incubated at 50° C. for 24 hours. The reaction was stopped via filtration of enzyme with a Vivaspin 2 concentrator (10,000 MWCO). Mannose was verified via HPLC as described in Example 20.

Example 22

A reaction mixture containing 200 g/L maltodextrin, 10 mM acetate buffer (pH 5.5), 5 mM MgCl$_2$, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U M6PI/PGPMI (no PGI needed in PGPMI case), and 0.05 U M6PP was incubated at 50° C. for 24 hours. Production of mannose was verified as in Example 20.

Example 23

To further increase mannose yields from maltodextrin, 0.05 U 4-glucan transferase (4GT) was added to the reaction described in Example 21.
A 0.2 mL reaction mixture containing 20 g/L isoamylase treated maltodextrin (see Example 22), 50 mM phosphate buffered saline pH 7.2, 5 mM MgCl$_2$, 0.05 U of αGP, 0.05 U PGM, 0.05 U PGI, 0.05 U M6PI/PGPMI (no PGI needed in PGPMI case), 0.05 U M6PP, and 0.05 U 4GT was incubated at 50° C. for 24 hours. Production of mannose was verified as in Example 20.

Example 24

To further increase mannose yields from maltodextrin, 0.05 U maltose phosphorylase is added to the reaction described in Example 21.

Example 25

To further increase mannose yields from maltodextrin, 0.05 U polyphosphate glucokinase and 75 mM polyphosphate is added to the reaction described in Example 21.

Example 26

To produce mannose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U M6PI/PGPMI (no PGI needed in PGPMI case), and 0.05 U M6PP is incubated at 50° C. for 24 hours. Production of mannose is quantified as in Example 20.

Example 27

To produce mannose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U M6PI/PGPMI (no PGI needed in PGPMI case), and 0.05 U M6PP is incubated at 50° C. for 24 hours. Production of mannose is quantified as in Example 20.

Example 28

To produce mannose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U M6PI/PGPMI (no PGI needed in PGPMI case), and 0.05 U M6PP is incubated at 50° C. for 24 hours. Production of mannose is quantified as in Example 20.

Example 29

To further increase yields of mannose from sucrose, 75 mM polyphosphate and 0.05 polyphosphate fructokinase is added to the reaction mixture in Example 28. Production of mannose is quantified as in Example 20.

Galactose

Example 30

To validate galactose production from F6P, 10 g/L F6P is mixed with 1 U/mL Gal6PI, and 1 U/mL Gal6PP in 50 mM HEPES buffer (pH 7.2) containing 5 mM MgCl$_2$. The reaction is incubated for 3 hours at 37° C. Conversion of F6P to galactose is seen via HPLC (Agilent 1100 series) using an Agilent Hi-Plex H-column and refractive index detector. The sample and control are run in 5 mM H$_2$SO$_4$ at 0.6 mL/min and 65° C.

Example 31

To validate production of galactose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U Gal6PI, and 0.05 U Gal6PP is incubated at 37° C. for 24 hours. The reaction is stopped via filtration of enzyme with a Vivaspin 2 concentrator (10,000 MWCO). Galactose is verified via HPLC as described in Example 30.

Example 32

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U Gal6PI, and 0.05 U Gal6PP is incubated at 37° C. for 24 hours. Production of galactose is verified as in Example 30.

Example 33

To further increase galactose yields from maltodextrin, 0.05 U 4-glucan transferase (4GT) is added to the reaction described in Example 31.
A 0.2 mL reaction mixture containing 20 g/L isoamylase treated maltodextrin (see Example 12), 50 mM phosphate buffered saline pH 7.2, 5 mM MgCl$_2$, 0.05 U of αGP, 0.05 U PGM, 0.05 U PGI, 0.05 U Gal6PI, 0.05 U Gal6PP, and 0.05 U 4GT is incubated at 37° C. for 24 hours. Production of galactose is verified as in Example 30.

Example 34

To further increase galactose yields from maltodextrin, 0.05 U maltose phosphorylase is added to the reaction described in Example 31.

Example 35

To further increase galactose yields from maltodextrin, 0.05 U polyphosphate glucokinase and 75 mM polyphosphate is added to the reaction described in Example 31.

Example 36

To produce galactose from fructose, a reaction mixture containing 10 g/L fructose, 50 mM Tris buffer pH 7.0, 75 mM polyphosphate, 5 mM $MgCl_2$, 0.05 U fructose polyphosphate kinase, 0.05 U Gal6PI, and 0.05 U Gal6PP is incubated at 37° C. for 24 hours. Production of galactose is quantified as in Example 30.

Example 37

To produce galactose from glucose, a reaction mixture containing 10 g/L glucose, 50 mM Tris buffer pH 7.0, 75 mM polyphosphate, 5 mM $MgCl_2$, 0.05 U glucose polyphosphate kinase, 0.05 U PGI, 0.05 U Gal6PI, and 0.05 U Gal6PP is incubated at 37° C. for 24 hours. Production of galactose is quantified as in Example 30.

Example 38

To produce galactose from sucrose, a reaction mixture containing 10 g/L sucrose, 50 mM phosphate buffered saline pH 7.0, 5 mM $MgCl_2$, 0.05 U sucrose phosphorylase, 0.05 PGM, 0.05 U PGI, 0.05 U Gal6PI, and 0.05 U Gal6PP is incubated at 37° C. for 24 hours. Production of galactose is quantified as in Example 30.

Example 39

To further increase yields of galactose from sucrose, 75 mM polyphosphate and 0.05 polyphosphate fructokinase is added to the reaction mixture in Example 38. Production of galactose is quantified as in Example 30.

Example 40

To validate galactose production from Gal6P, 10 g/L Gal6P was mixed with 1 U/mL Gal6PP in 50 mM HEPES buffer (pH 7.2) containing 5 mM $MgCl_2$. The reaction was incubated for 1 hour at 50° C. Conversion of Gal6P to galactose is seen free phosphate detection. To detect free phosphate release, 500 µL of a solution containing 0.1 M zinc acetate and 2 mM ammonium molybdate (pH 5) was added to 50 µL of reaction. This was mixed by and followed by 125 µL of 5% ascorbic acid (pH 5). This solution was mixed then incubated at 30° C. for 20 min. The absorbance at 850 nm was read to determine free phosphate release.

Fructose

Example 41

To validate fructose production from F6P, 10 g/L F6P was mixed with 1 U/mL F6PP in 50 mM HEPES buffer (pH 7.2) containing 5 mM $MgCl_2$. The reaction was incubated for 3 hours at 50° C. Conversion of F6P to fructose was seen via HPLC (Agilent 1100 series) using an Agilent Hi-Plex H-column and refractive index detector. The sample and control were run in 5 mM $H_2SO_4$ at 0.6 mL/min and 65° C.

Example 42

To validate production of fructose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, and 0.05 U F6PP was incubated at 50° C. for 24 hours. The reaction was stopped via filtration of enzyme with a Vivaspin 2 concentrator (10,000 MWCO). Fructose was verified via HPLC as described in Example 41.

Example 43

A reaction mixture containing 200 g/L maltodextrin, 10 mM acetate buffer (pH 5.5), 5 mM $MgCl_2$, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM $MgCl_2$, 0.05 U of αGP, 0.05 U PGM, 0.05 U PGI, and 0.05 U F6PP was incubated at 50° C. for 24 hours. Production of fructose was verified as in Example 41.

Example 44

To further increase fructose yields from maltodextrin, 0.05 U 4-glucan transferase (4GT) was added to the reaction described in Example 42.

A 0.2 mL reaction mixture containing 20 g/L isoamylase treated maltodextrin (see Example 12), 50 mM phosphate buffered saline pH 7.2, 5 mM $MgCl_2$, 0.05 U of αGP, 0.05 U PGM, 0.05 U PGI, 0.05 U F6PP, and 0.05 U 4GT was incubated at 50° C. for 24 hours. Production of fructose was verified as in Example 41.

Example 45

To further increase fructose yields from maltodextrin, 0.05 U maltose phosphorylase is added to the reaction described in Example 42.

Example 46

To further increase fructose yields from maltodextrin, 0.05 U polyphosphate glucokinase and 75 mM polyphosphate is added to the reaction described in Example 42.

Example 47

To produce fructose from glucose, a reaction mixture containing 10 g/L glucose, 50 mM Tris buffer pH 7.0, 75 mM polyphosphate, 5 mM $MgCl_2$, 0.05 U glucose polyphosphate kinase, 0.05 U PGI, and 0.05 U F6PP is incubated at 50° C. for 24 hours. Production of fructose is quantified as in Example 41.

Example 48

To produce fructose from sucrose, a reaction mixture containing 10 g/L sucrose, 50 mM phosphate buffered saline pH 7.0, 5 mM $MgCl_2$, 0.05 U sucrose phosphorylase, 0.05 PGM, 0.05 U PGI, and 0.05 U F6PP was incubated at 50° C. for 24 hours. Production of fructose was quantified as in Example 41.

Altrose

Example 49

To validate altrose production from F6P, 10 g/L F6P is mixed with 1 U/mL P6PE, 1 U/mL altrose 6-phosphate isomerase (Alt6PI), and 1 U/mL altrose 6-phosphate phosphatase (Alt6PP) in 50 mM HEPES buffer (pH 7.2) containing 5 mM MgCl$_2$. The reaction is incubated for 3 hours at 50° C. Conversion of F6P to altrose is seen via HPLC (Agilent 1100 series) using an Agilent Hi-Plex H-column and refractive index detector. The sample and control are run in 5 mM H$_2$SO$_4$ at 0.6 mL/min and 65° C.

Example 50

To validate production of altrose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U P6PE, 0.05 U Alt6PI, and 0.05 U Alt6PP is incubated at 50° C. for 24 hours. The reaction is stopped via filtration of enzyme with a Vivaspin 2 concentrator (10,000 MWCO). Altrose is verified via HPLC as described in Example 49.

Example 51

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U P6PE, 0.05 U Alt6PI, and 0.05 U Alt6PP is incubated at 50° C. for 24 hours. Production of altrose is verified as in Example 49.

Example 52

To further increase altrose yields from maltodextrin, 0.05 U 4-glucan transferase (4GT) is added to the reaction described in Example 50.

A 0.2 mL reaction mixture containing 20 g/L isoamylase treated maltodextrin (see Example 50), 50 mM phosphate buffered saline pH 7.2, 5 mM MgCl$_2$, 0.05 U of αGP, 0.05 U PGM, 0.05 U PGI, 0.05 U P6PE, 0.05 U Alt6PI, 0.05 U Alt6PP, and 0.05 U 4GT is incubated at 50° C. for 24 hours. Production of altrose is verified as in Example 49.

Example 53

To further increase altrose yields from maltodextrin, 0.05 U maltose phosphorylase is added to the reaction described in Example 50.

Example 54

To further increase altrose yields from maltodextrin, 0.05 U polyphosphate glucokinase and 75 mM polyphosphate is added to the reaction described in Example 50.

Example 55

To produce altrose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U P6PE, 0.05 U Alt6PI, and 0.05 U Alt6PP is incubated at 50° C. for 24 hours. Production of altrose is quantified as in Example 49.

Example 56

To produce altrose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U P6PE, 0.05 U Alt6PI, and 0.05 U Alt6PP is incubated at 50° C. for 24 hours. Production of altrose is quantified as in Example 49.

Example 57

To produce altrose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U P6PE, 0.05 U Alt6PI, and 0.05 U Alt6PP is incubated at 50° C. for 24 hours. Production of altrose is quantified as in Example 49.

Example 58

To further increase yields of altrose from sucrose, 75 mM polyphosphate and 0.05 polyphosphate fructokinase is added to the reaction mixture in Example 56. Production of altrose is quantified as in Example 49.

Talose

Example 59

To validate talose production from F6P, 10 g/L F6P is mixed with 1 U/mL F6PE, 1 U/mL talose 6-phosphate isomerase (Tal6PI), and 1 U/mL talose 6-phosphate phosphatase (Tal6PP) in 50 mM HEPES buffer (pH 7.2) containing 5 mM MgCl$_2$. The reaction is incubated for 3 hours at 50° C. Conversion of F6P to talose is seen via HPLC (Agilent 1100 series) using an Agilent Hi-Plex H-column and refractive index detector. The sample and control are run in 5 mM H$_2$SO$_4$ at 0.6 mL/min and 65° C.

Example 60

To validate production of talose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U Tal6PI, and 0.05 U Tal6PP is incubated at 50° C. for 24 hours. The reaction is stopped via filtration of enzyme with a Vivaspin 2 concentrator (10,000 MWCO). Talose is verified via HPLC as described in Example 59.

Example 61

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U Tal6PI, and 0.05 U Tal6PP is incubated at 50° C. for 24 hours. Production of talose is verified as in Example 59.

Example 62

To further increase talose yields from maltodextrin, 0.05 U 4-glucan transferase (4GT) is added to the reaction described in Example 60.

A 0.2 mL reaction mixture containing 20 g/L isoamylase treated maltodextrin (see Example 60), 50 mM phosphate buffered saline pH 7.2, 5 mM MgCl$_2$, 0.05 U of αGP, 0.05 U PGM, 0.05 U PGI, 0.05 U F6PE, 0.05 U Tal6PI, 0.05 U Tal6PP, and 0.05 U 4GT is incubated at 50° C. for 24 hours. Production of talose is verified as in Example 59.

Example 63

To further increase talose yields from maltodextrin, 0.05 U maltose phosphorylase is added to the reaction described in Example 59.

Example 64

To further increase talose yields from maltodextrin, 0.05 U polyphosphate glucokinase and 75 mM polyphosphate is added to the reaction described in Example 60.

Example 65

To produce talose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U F6PE, 0.05 U Tal6PI, and 0.05 U Tal6PP is incubated at 50° C. for 24 hours. Production of talose is quantified as in Example 59.

Example 66

To produce talose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U F6PE, 0.05 U Tal6PI, and 0.05 U Tal6PP is incubated at 50° C. for 24 hours. Production of talose is quantified as in Example 59.

Example 67

To produce talose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U F6PE, 0.05 U Tal6PI, and 0.05 U Tal6PP is incubated at 50° C. for 24 hours. Production of talose is quantified as in Example 59.

Example 68

To further increase yields of talose from sucrose, 75 mM polyphosphate and 0.05 polyphosphate fructokinase is added to the reaction mixture in Example 66. Production of talose is quantified as in Example 59.

Sorbose

Example 69

To validate sorbose production from F6P, 10 g/L F6P is mixed with 1 U/mL F6PE, 1 U/mL sorbose 6-phosphate 3-epimerase (S6PE), and 1 U/mL sorbose 6-phosphate phosphatase (S6PP) in 50 mM HEPES buffer (pH 7.2) containing 5 mM MgCl$_2$. The reaction is incubated for 3 hours at 50° C. Conversion of F6P to sorbose is seen via HPLC (Agilent 1100 series) using an Agilent Hi-Plex H-column and refractive index detector. The sample and control are run in 5 mM H$_2$SO$_4$ at 0.6 mL/min and 65° C.

Example 70

To validate production of sorbose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, and 0.05 U S6PP is incubated at 50° C. for 24 hours. The reaction is stopped via filtration of enzyme with a Vivaspin 2 concentrator (10,000 MWCO). Sorbose is verified via HPLC as described in Example 68.

Example 71

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, and 0.05 U S6PP is incubated at 50° C. for 24 hours. Production of sorbose is verified as in Example 69.

Example 72

To further increase sorbose yields from maltodextrin, 0.05 U 4-glucan transferase (4GT) is added to the reaction described in Example 70.

A 0.2 mL reaction mixture containing 20 g/L isoamylase treated maltodextrin (see Example 70), 50 mM phosphate buffered saline pH 7.2, 5 mM MgCl$_2$, 0.05 U of αGP, 0.05 U PGM, 0.05 U PGI, 0.05 U F6PE, 0.05 U S6PE, 0.05 U S6PP, and 0.05 U 4GT is incubated at 50° C. for 24 hours. Production of sorbose is verified as in Example 69.

Example 73

To further increase sorbose yields from maltodextrin, 0.05 U maltose phosphorylase is added to the reaction described in Example 70.

Example 74

To further increase sorbose yields from maltodextrin, 0.05 U polyphosphate glucokinase and 75 mM polyphosphate is added to the reaction described in Example 69.

Example 75

To produce sorbose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U F6PE, 0.05 U S6PE, and 0.05 U S6PP is incubated at 50° C. for 24 hours. Production of sorbose is quantified as in Example 69.

Example 76

To produce sorbose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U F6PE, 0.05 U S6PE, and 0.05 U S6PP is incubated at 50° C. for 24 hours. Production of sorbose is quantified as in Example 69.

Example 77

To produce sorbose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U F6PE, 0.05 U S6PE, and 0.05 U S6PP is incubated at 50° C. for 24 hours. Production of sorbose is quantified as in Example 69.

Example 78

To further increase yields of sorbose from sucrose, 75 mM polyphosphate and 0.05 polyphosphate fructokinase is added to the reaction mixture in Example 76. Production of sorbose is quantified as in Example 69.

Gulose

Example 79

To validate gulose production from F6P, 10 g/L F6P is mixed with 1 U/mL F6PE, 1 U/mL S6PE, 1 U/mL gulose 6-phosphate isomerase (Gul6PI), and 1 U/mL gulose 6-phosphate phosphatase (Gul6PP) in 50 mM HEPES buffer (pH 7.2) containing 5 mM $MgCl_2$. The reaction is incubated for 3 hours at 50° C. Conversion of F6P to gulose is seen via HPLC (Agilent 1100 series) using an Agilent Hi-Plex H-column and refractive index detector. The sample and control are run in 5 mM $H_2SO_4$ at 0.6 mL/min and 65° C.

Example 80

To validate production of gulose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, 0.05 U F6PE, 0.05 U S6PE, 0.05 U Gul6PI, and 0.05 U Gul6PP is incubated at 50° C. for 24 hours. The reaction is stopped via filtration of enzyme with a Vivaspin 2 concentrator (10,000 MWCO). Gulose is verified via HPLC as described in Example 79.

Example 81

A reaction mixture containing 200 g/L maltodextrin, 10 mM acetate buffer (pH 5.5), 5 mM $MgCl_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM $MgCl_2$, 0.05 U of αGP, 0.05 U PGM, 0.05 U PGI, 0.05 U F6PE, 0.05 U S6PE, 0.05 U Gul6PI, and 0.05 U Gul6PP is incubated at 50° C. for 24 hours. Production of gulose is verified as in Example 79.

Example 82

To further increase gulose yields from maltodextrin, 0.05 U 4-glucan transferase (4GT) is added to the reaction described in Example 80.

A 0.2 mL reaction mixture containing 20 g/L isoamylase treated maltodextrin (see Example 80), 50 mM phosphate buffered saline pH 7.2, 5 mM $MgCl_2$, 0.05 U of αGP, 0.05 U PGM, 0.05 U PGI 0.05 U F6PE, 0.05 U S6PE, 0.05 U Gul6PI, 0.05 U Gul6PP, and 0.05 U 4GT is incubated at 50° C. for 24 hours. Production of gulose is verified as in Example 79.

Example 83

To further increase gulose yields from maltodextrin, 0.05 U maltose phosphorylase is added to the reaction described in Example 80.

Example 84

To further increase gulose yields from maltodextrin, 0.05 U polyphosphate glucokinase and 75 mM polyphosphate is added to the reaction described in Example 80.

Example 85

To produce gulose from fructose, a reaction mixture containing 10 g/L fructose, 50 mM Tris buffer pH 7.0, 75 mM polyphosphate, 5 mM $MgCl_2$, 0.05 U fructose polyphosphate kinase, 0.05 U F6PE, 0.05 U S6PE, 0.05 U Gul6PI, and 0.05 U Gul6PP is incubated at 50° C. for 24 hours. Production of gulose is quantified as in Example 79.

Example 86

To produce gulose from glucose, a reaction mixture containing 10 g/L glucose, 50 mM Tris buffer pH 7.0, 75 mM polyphosphate, 5 mM $MgCl_2$, 0.05 U glucose polyphosphate kinase, 0.05 U PGI, 0.05 U F6PE, 0.05 U S6PE, 0.05 U Gul6PI, and 0.05 U Gul6PP is incubated at 50° C. for 24 hours. Production of gulose is quantified as in Example 79.

Example 87

To produce gulose from sucrose, a reaction mixture containing 10 g/L sucrose, 50 mM phosphate buffered saline pH 7.0, 5 mM $MgCl_2$, 0.05 U sucrose phosphorylase, 0.05 PGM, 0.05 U PGI, 0.05 U F6PE, 0.05 U S6PE, 0.05 U Gul6PI, and 0.05 U Gul6PP is incubated at 50° C. for 24 hours. Production of gulose is quantified as in Example 79.

Example 88

To further increase yields of gulose from sucrose, 75 mM polyphosphate and 0.05 polyphosphate fructokinase is added to the reaction mixture in Example 86. Production of gulose is quantified as in Example 79.

Idose

Example 89

To validate idose production from F6P, 10 g/L F6P is mixed with 1 U/mL F6PE, 1 U/mL S6PE, 1 U/mL idose 6-phosphate isomerase (I6PI), and 1 U/mL idose 6-phosphate phosphatase (I6PP) in 50 mM HEPES buffer (pH 7.2) containing 5 mM $MgCl_2$. The reaction is incubated for 3 hours at 50° C. Conversion of F6P to idose is seen via HPLC (Agilent 1100 series) using an Agilent Hi-Plex H-column and refractive index detector. The sample and control are run in 5 mM $H_2SO_4$ at 0.6 mL/min and 65° C.

Example 90

To validate production of idose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, 0.05 U F6PE, 0.05 U S6PE, 0.05 U I6PI, and 0.05 U I6PP is incubated at 50° C. for 24 hours. The reaction is stopped via filtration of enzyme with a Vivaspin 2 concentrator (10,000 MWCO). Idose is verified via HPLC as described in Example 89.

Example 91

A reaction mixture containing 200 g/L maltodextrin, 10 mM acetate buffer (pH 5.5), 5 mM $MgCl_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, 0.05 U I6PI and 0.05 U I6PP is incubated at 50° C. for 24 hours. Production of idose is verified as in Example 89.

Example 92

To further increase idose yields from maltodextrin, 0.05 U 4-glucan transferase (4GT) is added to the reaction described in Example 90.

A 0.2 mL reaction mixture containing 20 g/L isoamylase treated maltodextrin (see Example 90), 50 mM phosphate buffered saline pH 7.2, 5 mM MgCl$_2$, 0.05 U of αGP, 0.05 U PGM, 0.05 U PGI 0.05 U F6PE, 0.05 U S6PE, 0.05 U I6PI, 0.05 U I6PP, and 0.05 U 4GT is incubated at 50° C. for 24 hours. Production of idose is verified as in Example 89.

Example 93

To further increase idose yields from maltodextrin, 0.05 U maltose phosphorylase is added to the reaction described in Example 90.

Example 94

To further increase idose yields from maltodextrin, 0.05 U polyphosphate glucokinase and 75 mM polyphosphate is added to the reaction described in Example 90.

Example 95

To produce idose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U F6PE, 0.05 U S6PE, 0.05 U I6PI, and 0.05 U I6PP is incubated at 50° C. for 24 hours. Production of idose is quantified as in Example 89.

Example 96

To produce idose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U F6PE, 0.05 U S6PE, 0.05 U I6PI, and 0.05 U I6PP is incubated at 50° C. for 24 hours. Production of idose is quantified as in Example 89.

Example 97

To produce idose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U F6PE, 0.05 U S6PE, 0.05 U I6PI, and 0.05 U I6PP is incubated at 50° C. for 24 hours. Production of idose is quantified as in Example 89.

Example 98

To further increase yields of idose from sucrose, 75 mM polyphosphate and 0.05 polyphosphate fructokinase is added to the reaction mixture in Example 96. Production of idose is quantified as in Example 89.

Tagatose

Example 99

To validate tagatose production from F6P, 2 g/L F6P was mixed with 1 U/ml fructose 6-phosphate epimerase (F6PE) and 1 U/ml tagatose 6-phosphate phosphatase (T6PP) in 50 mM HEPES buffer (pH 7.2) containing 5 mM MgCl2. The reaction was incubated for 16 hours at 50° C. 100% conversion of F6P to tagatose is seen via HPLC (Agilent 1100 series) using an Agilent Hi-Plex H-column and refractive index detector. The sample was run in 5 mM H2SO4 at 0.6 mL/min.

Example 100

To validate production of tagatose from maltodextrin, a 0.20 mL reaction mixture containing 20 g/L maltodextrin, 50 mM phosphate buffered saline pH 7.2, 5 mM MgCl2, 0.05 U of αGP, 0.05 U PGM, 0.05 U PGI, 0.05 U F6PE, and 0.05 U T6PP was incubated at 50° C. for 24 hours. The reaction was stopped via filtration of enzyme with a Vivaspin 2 concentrator (10,000 MWCO). Tagatose was detected and quantified using an Agilent 1100 series HPLC with refractive index detector and an Agilent Hi-Plex H-column. The mobile phase was 5 mM H2SO4, which ran at 0.6 mL/min. A yield of 9.2 g/L tagatose was obtained. This equates to 92% of the theoretical yield due to limits of maltodextrin degradation without enzymes such as isoamylase or 4-glucan transferase. Standards of various concentrations of tagatose were used to quantify our yield.

Example 101

A reaction mixture containing 200 g/L maltodextrin, 10 mM acetate buffer (pH 5.5), 5 mM MgCl2, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM MgCl2, 0.05 U of αGP, 0.05 U PGM, 0.05 U PGI, 0.05 U F6PE, and 0.05 U T6PP was incubated at 50° C. for 24 hours. Production of tagatose was quantified as in Example 99. The yield of tagatose was increased to 16 g/L with the pretreatment of maltodextrin by isoamylase. This equates to 80% of the theoretical yield.

Example 102

To further increase tagatose yields from maltodextrin, 0.05 U 4-glucan transferase (4GT) was added to the reaction described in Example 100.

A 0.2 mL reaction mixture containing 20 g/L isoamylase treated maltodextrin (see example 9), 50 mM phosphate buffered saline pH 7.2, 5 mM MgCl2, 0.05 U of αGP, 0.05 U PGM, 0.05 U PGI, 0.05 U F6PE, 0.05 U T6PP, and 0.05 U 4GT was incubated at 50° C. for 24 hours. Production of tagatose was quantified as in example 9. The yield of tagatose was increased to 17.7 g/L with the addition of 4GT to IA-treated maltodextrin. This equates to 88.5% of the theoretical yield.

Example 103

To investigate scale-up, a 20 mL reaction mixture containing 50 g/L isoamylase treated maltodextrin (see Example 99), 50 mM phosphate buffered saline pH 7.2, 5 mM MgCl2, 10 U of αGP, 10 U PGM, 10 U PGI, 10 U F6PE, and 10 U T6PP was incubated at 50° C. for 24 hours. Production of tagatose was quantified as in example 8. The yield of tagatose was 37.6 g/L at the 20 mL scale and 50 g/L maltodextrin. This equates to 75% of the theoretical yield. These results indicate that scale-up to larger reaction volumes will not result in significant loses of yield.

Example 104

To further increase tagatose yields from maltodextrin, 0.05 U maltose phosphorylase is added to the reaction described in Example 100.

Example 105

To further increase tagatose yields from maltodextrin, 0.05 U polyphosphate glucokinase and 75 mM polyphosphate is added to the reaction described in Example 99.

Example 106

To produce tagatose from fructose, a reaction mixture containing 10 g/L fructose, 50 mM Tris buffer pH 7.0, 75 mM polyphosphate, 5 mM MgCl2, 0.05 U fructose polyphosphate kinase, 0.05 U F6PE, and 0.05 U T6PP is incubated at 50° C. for 24 hours. Production of tagatose is quantified as in Example 100.

Example 107

To produce tagatose from glucose, a reaction mixture containing 10 g/L glucose, 50 mM Tris buffer pH 7.0, 75 mM polyphosphate, 5 mM MgCl2, 0.05 U glucose polyphosphate kinase, 0.05 U PGI, 0.05 U F6PE, and 0.05 U T6PP is incubated at 50° C. for 24 hours. Production of tagatose is quantified as in Example 100.

Example 108

To produce tagatose from sucrose, a reaction mixture containing 10 g/L sucrose, 50 mM phosphate buffered saline pH 7.0, 5 mM MgCl2, 0.05 U sucrose phosphorylase, 0.05 PGM, 0.05 U PGI, 0.05 U F6PE, and 0.05 U T6PP is incubated at 50° C. for 24 hours. Production of tagatose is quantified as in Example 100.

Example 109

To further increase yields of tagatose from sucrose, 75 mM polyphosphate and 0.05 polyphosphate fructokinase is added to the reaction mixture in example 15. Production of tagatose is quantified as in Example 100.

Psicose

Example 110

To validate psicose production from F6P, 2 g/L F6P was mixed with 1 U/ml P6PE and 1 U/ml P6PP in 50 mM HEPES buffer (pH 7.2) containing 5 mM MgCl$_2$ and 80 µM CoCl$_2$. The reaction was incubated for 6 hours at 50° C. 99% conversion of F6P to psicose was seen via HPLC (Agilent 1100 series) using an Agilent Hi-Plex H-column and refractive index detector. The sample was run in 5 mM H$_2$SO$_4$ at 0.6 mL/min.

Example 111

To validate production of psicose from maltodextrin, a 0.20 mL reaction mixture containing 20 g/L maltodextrin, 50 mM phosphate buffered saline pH 7.2, 5 mM MgCl$_2$, 80 µM CoCl$_2$, 0.05 U of αGP, 0.05 U PGM, 0.05 U PGI, 0.05 U P6PE and 0.05 U P6PP is incubated at 50° C. for 24 hours. The reaction is stopped via filtration of enzyme with a Vivaspin 2 concentrator (10,000 MWCO). Psicose is detected and quantified using an Agilent 1100 series HPLC with refractive index detector and an Agilent Hi-Plex H-column. The mobile phase is 5 mM H$_2$SO$_4$, which runs at 0.6 mL/min. Standards of various concentrations of psicose are used to quantify our yield.

Example 112

A reaction mixture containing 200 g/L maltodextrin, 10 mM acetate buffer (pH 5.5), 5 mM MgCl$_2$, 80 µM CoCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U P6PE, and 0.05 U P6PP is incubated at 50° C. for 24 hours. Production of psicose is quantified as in Example 111.

Example 113

A reaction mixture containing 200 g/L maltodextrin, 10 mM acetate buffer (pH 4.5), 5 mM MgCl$_2$, and 1:200 dilution of Novozymes D6 pullulanase is incubated at 50° C. for 4 hours. This is used to create another reaction mixture containing 20 g/L pullulanase treated maltodextrin, 50 mM phosphate buffered saline pH 7.2, 5 mM MgCl$_2$, 80 µM CoCl$_2$, 0.05 U of αGP, 0.05 U PGM, 0.05 U PGI, 0.05 U P6PE, and 0.05 U P6PP is incubated at 50° C. for 24 hours. Production of psicose is quantified as in Example 111.

Example 114

To further increase psicose yields from maltodextrin, 0.05 U 4-glucan transferase (4GT) is added to the reaction described in Example 111.

A 0.2 mL reaction mixture containing 20 g/L isoamylase treated maltodextrin (see example 9), 50 mM phosphate buffered saline pH 7.2, 5 mM MgCl$_2$, 80 µM CoCl$_2$, 0.05 U of αGP, 0.05 U PGM, 0.05 U PGI, 0.05 U P6PE, 0.05 U P6PP, and 0.05 U 4GT is incubated at 50° C. for 24 hours. Production of psicose is quantified as in Example 111.

Example 115

To investigate scale-up, a 20 mL reaction mixture containing 50 g/L isoamylase treated maltodextrin (see Example 10), 50 mM phosphate buffered saline pH 7.2, 5 mM MgCl$_2$, 80 µM CoCl$_2$, 10 U of αGP, 10 U PGM, 10 U PGI, 10 U P6PE, and 10 U P6PP is incubated at 50° C. for 24 hours. Production of psicose was quantified as in Example 111.

Example 116

To further increase psicose yields from maltodextrin, 0.05 U maltose phosphorylase is added to the reaction described in Example 110.

Example 117

To further increase psicose yields from maltodextrin, 0.05 U polyphosphate glucokinase and 75 mM polyphosphate is added to the reaction described in Example 111.

Example 118

To produce psicose from fructose, a reaction mixture containing 10 g/L fructose, 50 mM Tris buffer pH 7.0, 75 mM polyphosphate, 5 mM MgCl2, 80 µM CoCl2, 0.05 U fructose polyphosphate kinase, 0.05 U P6PE, and 0.05 U P6PP is incubated at 50° C. for 24 hours. Production of psicose is quantified as in Example 111.

Example 119

To produce psicose from glucose, a reaction mixture containing 10 g/L glucose, 50 mM Tris buffer pH 7.0, 75 mM polyphosphate, 5 mM $MgCl_2$, 80 µM $CoCl_2$, 0.05 U glucose polyphosphate kinase, 0.05 U PGI, 0.05 U P6PE, and 0.05 U P6PP is incubated at 50° C. for 24 hours. Production of psicose is quantified as in Example 111.

Example 120

To produce psicose from sucrose, a reaction mixture containing 10 g/L sucrose, 50 mM phosphate buffered saline pH 7.0, 5 mM MgCl2, 80 µM CoCl2, 0.05 U sucrose phosphorylase, 0.05 PGM, 0.05 U PGI, 0.05 U P6PE, and 0.05 U P6PP is incubated at 50° C. for 24 hours. Production of psicose is quantified as in Example 111.

Example 121

To further increase yields of psicose from sucrose, 75 mM polyphosphate and 0.05 polyphosphate fructokinase is added to the reaction mixture in example 20. Production of psicose is quantified as in Example 111.

The invention includes all embodiments and variations substantially as hereinbefore described and with reference to the examples and figures. Although various embodiments of the invention are disclosed herein, adaptations and modifications may be made within the scope of the invention in accordance with the common general knowledge of those skilled in this art.

---

The claimed invention is:

1. A process for preparing allose from a saccharide, the process comprising:
   - converting fructose 6-phosphate (F6P) to psicose 6-phosphate (P6P), catalyzed by a psicose 6-phosphate 3-epimerase (P6PE);
   - converting the P6P to allose 6-phosphate (A6P) catalyzed by an allose 6-phosphate isomerase (A6PI); and
   - converting the A6P to allose catalyzed by an allose 6-phosphate phosphatase (A6PP).

2. The process of claim 1, further comprising a step of converting glucose 6-phosphate (G6P) to the F6P, wherein the step is catalyzed by a phosphoglucoisomerase (PGI).

3. The process of claim 2, further comprising the step of converting glucose 1-phosphate (G1P) to the G6P, wherein the step is catalyzed by a phosphoglucomutase (PGM).

4. The process of claim 3, further comprising the step of converting a saccharide to the G1P, wherein the step is catalyzed by at least one enzyme, wherein the saccharide is starch, a starch derivative, or sucrose.

5. The process of claim 4, wherein the at least one enzyme in the step of converting a saccharide to the G1P is selected from the group consisting of an alpha-glucan phosphorylase (αGP), a sucrose phosphorylase, and mixtures thereof.

6. The process of claim 4, wherein the saccharide is starch or a derivative thereof selected from the group consisting of amylose, amylopectin, soluble starch, amylodextrin, maltodextrin, maltose, and glucose, and mixtures thereof.

7. The process of claim 6, further comprising the step of converting starch to a starch derivative wherein the starch derivative is prepared by enzymatic hydrolysis of starch or by acid hydrolysis of starch.

8. The process of claim 6, wherein 4-glucan transferase (4GT) is added to the process.

9. The process of claim 4, wherein the starch derivative is prepared by enzymatic hydrolysis of starch catalyzed by isoamylase, pullulanase, alpha-amylase, or a combination thereof.

10. The process of claim 1, wherein the process steps are conducted at a temperature ranging from about 37° C. to about 85° C., at a pH ranging from about 5.0 to about 9.0, and/or for about 0.5 hours to about 48 hours.

11. The process of claim 1, wherein the process steps are conducted in a single bioreactor.

12. The process of claim 1, wherein the process steps are conducted ATP-free, NAD(P)(H)-free, at a phosphate concentration from about 0.1 mM to about 150 mM, the phosphate is recycled, and/or the catalysis by the hexose-specific phosphatase involves an energetically favorable chemical reaction.

* * * * *